(12) United States Patent
Cottrell et al.

(10) Patent No.: US 8,426,359 B2
(45) Date of Patent: Apr. 23, 2013

(54) INHIBITORS OF SERINE PROTEASES, PARTICULARLY HCV NS3-NS4A PROTEASE

(75) Inventors: Kevin M. Cottrell, Cambridge, MA (US); Robert B. Perni, Marlborough, MA (US); Janos Pitlik, Westborough, MA (US); Wayne C. Schairer, Westborough, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 1112 days.

(21) Appl. No.: 12/265,125

(22) Filed: Nov. 5, 2008

(65) Prior Publication Data

US 2009/0291902 A1  Nov. 26, 2009

Related U.S. Application Data

(63) Continuation of application No. 10/943,265, filed on Sep. 17, 2004, now abandoned.

(60) Provisional application No. 60/504,405, filed on Sep. 18, 2003.

(51) Int. Cl.
*A61K 38/00* (2006.01)

(52) U.S. Cl.
USPC .......................................................... 514/3.7

(58) Field of Classification Search .................. None
See application file for complete search history.

(56) References Cited

U.S. PATENT DOCUMENTS

| | | |
|---|---|---|
| 6,265,380 B1 | 7/2001 | Tung et al. |
| 6,608,067 B1 | 8/2003 | Tung et al. |
| 6,617,309 B2 | 9/2003 | Tung et al. |
| 6,909,000 B2 | 6/2005 | Farmer et al. |
| 7,388,017 B2 | 6/2008 | Tung et al. |
| 2004/0077600 A1 | 4/2004 | Tung et al. |
| 2005/0119189 A1 | 6/2005 | Cottrell et al. |
| 2007/0179167 A1 | 8/2007 | Cottrell et al. |
| 2008/0045480 A1 | 2/2008 | Farmer et al. |

FOREIGN PATENT DOCUMENTS

| | | |
|---|---|---|
| WO | 01/74768 | 10/2001 |
| WO | 02/18369 | 3/2002 |
| WO | 03/006490 | 1/2003 |
| WO | 03/035060 | 5/2003 |
| WO | 03/087092 | 10/2003 |
| WO | 2004/092161 | 10/2004 |
| WO | 2004/092162 | 10/2004 |
| WO | 2005/007681 | 1/2005 |
| WO | 2005/035525 | 4/2005 |
| WO | 2005/037860 | 4/2005 |
| WO | 2005/077969 | 8/2005 |

OTHER PUBLICATIONS

Han et al., "α-Ketoamides, α-Ketoesters and α-Diketones as HCV NS3 Protease Inhibitors", Bioorganic & Medicinal Chemistry Letters, vol. 10, pp. 711-713, 2000.
U.S. Appl. No. 10/943,265, filed Sep. 17, 2004, Kevin M. Cottrell, et al, Office Action Date May 5, 2008.
U.S. Appl. No. 10/943,265, filed Sep. 17, 2004, Kevin M. Cottrell, et al, Office Action Date Sep. 12, 2007.
U.S. Appl. No. 10/943,265, filed Sep. 17, 2004, Kevin M. Cottrell, et al, Office Action Date May 2, 2006.

*Primary Examiner* — Thomas Heard
(74) *Attorney, Agent, or Firm* — Lisa A. Dixon; Susan C. Kelly

(57) ABSTRACT

The present invention relates to compounds of formula I:

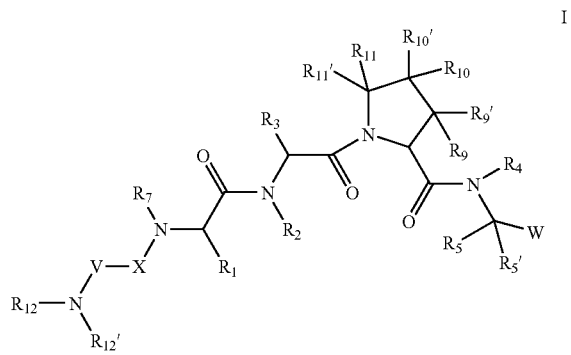

or a pharmaceutically acceptable salts thereof that inhibit serine protease activity, particularly the activity of hepatitis C virus NS3-NS4A protease. As such, they act by interfering with the life cycle of the hepatitis C virus and are useful as antiviral agents. The invention further relates to pharmaceutically acceptable compositions comprising said compounds either for ex vivo use or for administration to a patient suffering from HCV infection and to processes for preparing the compounds. The invention also relates to methods of treating an HCV infection in a patient by administering a pharmaceutical composition comprising a compound of this invention.

6 Claims, No Drawings

INHIBITORS OF SERINE PROTEASES, PARTICULARLY HCV NS3-NS4A PROTEASE

CROSS REFERENCE TO RELATED APPLICATIONS

The present application is a continuation application of U.S. Pat. No. 10/943,265, filed Sep. 17, 2004, now abandoned which claims the benefit, under 35 U.S.C. §119, of U.S. Provisional patent application No. 60/504,405, filed Sep. 18, 2003, entitled "Inhibitors of Serine Proteases, Particularly HCV NS3-NS4A Protease", the entire contents of each of which are hereby incorporated by reference.

TECHNICAL FIELD OF THE INVENTION

The present invention relates to compounds that inhibit serine protease activity, particularly the activity of hepatitis C virus NS3-NS4A protease. As such, they act by interfering with the life cycle of the hepatitis C virus and are also useful as antiviral agents. The invention further relates to pharmaceutical compositions comprising these compounds either for ex vivo use or for administration to a patient suffering from HCV infection. The invention also relates to processes for preparing the compounds and methods of treating an HCV infection in a patient by administering a pharmaceutical composition comprising a compound of this invention.

BACKGROUND OF THE INVENTION

Infection by hepatitis C virus ("HCV") is a compelling human medical problem. HCV is recognized as the causative agent for most cases of non-A, non-B hepatitis, with an estimated human sero-prevalence of 3% globally [A. Alberti et al., "Natural History of Hepatitis C," J. Hepatology, 31., (Suppl. 1), pp. 17-24 (1999)]. Nearly four million individuals may be infected in the United States alone [M. J. Alter et al., "The Epidemiology of Viral Hepatitis in the United States," Gastroenterol. Clin. North Am., 23, pp. 437-455 (1994); M. J. Alter "Hepatitis C Virus Infection in the United States," J. Hepatology, 31., (Suppl. 1), pp. 88-91 (1999)].

Upon first exposure to HCV only about 20% of infected individuals develop acute clinical hepatitis while others appear to resolve the infection spontaneously. In almost 70% of instances, however, the virus establishes a chronic infection that persists for decades [S. Iwarson, "The Natural Course of Chronic Hepatitis," FEMS Microbiology Reviews, 14, pp. 201-204 (1994); D. Lavanchy, "Global Surveillance and Control of Hepatitis C," J. Viral Hepatitis, 6, pp. 35-47 (1999)]. This usually results in recurrent and progressively worsening liver inflammation, which often leads to more severe disease states such as cirrhosis and hepatocellular carcinoma [M. C. Kew, "Hepatitis C and Hepatocellular Carcinoma", FEMS Microbiology Reviews, 14, pp. 211-220 (1994); I. Saito et. al., "Hepatitis C Virus Infection is Associated with the Development of Hepatocellular Carcinoma," Proc. Natl. Acad. Sci. USA, 87, pp. 6547-6549 (1990)]. Unfortunately, there are no broadly effective treatments for the debilitating progression of chronic HCV.

The HCV genome encodes a polyprotein of 3010-3033 amino acids [Q. L. Choo, et. al., "Genetic Organization and Diversity of the Hepatitis C Virus." Proc. Natl. Acad. Sci. USA, 88, pp. 2451-2455 (1991); N. Kato et al., "Molecular Cloning of the Human Hepatitis C Virus Genome From Japanese Patients with Non-A, Non-B Hepatitis," Proc. Natl. Acad. Sci. USA, 87, pp. 9524-9528 (1990); A. Takamizawa et. al., "Structure and Organization of the Hepatitis C Virus Genome Isolated From Human Carriers," J. Virol., 65, pp. 1105-1113 (1991)]. The HCV nonstructural (NS) proteins are presumed to provide the essential catalytic machinery for viral replication. The NS proteins are derived by proteolytic cleavage of the polyprotein [R. Bartenschlager et. al., "Nonstructural Protein 3 of the Hepatitis C Virus Encodes a Serine-Type Proteinase Required for Cleavage at the NS3/4 and NS4/5 Junctions," J. Virol., 67, pp. 3835-3844 (1993); A. Grakoui et. al., "Characterization of the Hepatitis C Virus-Encoded Serine Proteinase: Determination of Proteinase-Dependent Polyprotein Cleavage Sites," J. Virol., 67, pp. 2832-2843 (1993); A. Grakoui et. al., "Expression and Identification of Hepatitis C Virus Polyprotein Cleavage Products," J. Virol., 67, pp. 1385-1395 (1993); L. Tomei et. al., "NS3 is a serine protease required for processing of hepatitis C virus polyprotein", J. Virol., 67, pp. 4017-4026 (1993)].

The HCV NS protein 3 (NS3) contains a serine protease activity that helps process the majority of the viral enzymes, and is thus considered essential for viral replication and infectivity. It is known that mutations in the yellow fever virus NS3 protease decrease viral infectivity [Chambers, T. J. et. al., "Evidence that the N-terminal Domain of Nonstructural Protein NS3 From Yellow Fever Virus is a Serine Protease Responsible for Site-Specific Cleavages in the Viral Polyprotein", Proc. Natl. Acad. Sci. USA, 87, pp. 8898-8902 (1990)]. The first 181 amino acids of NS3 (residues 1027-1207 of the viral polyprotein) have been shown to contain the serine protease domain of NS3 that processes all four downstream sites of the HCV polyprotein [C. Lin et al., "Hepatitis C Virus NS3 Serine Proteinase: Trans-Cleavage Requirements and Processing Kinetics", J. Virol., 68, pp. 8147-8157 (1994)].

The HCV NS3 serine protease and its associated cofactor, NS4A, helps process all of the viral enzymes, and is thus considered essential for viral replication. This processing appears to be analogous to that carried out by the human immunodeficiency virus aspartyl protease, which is also involved in viral enzyme processing. HIV protease inhibitors, which inhibit viral protein processing, are potent antiviral agents in man, indicating that interrupting this stage of the viral life cycle results in therapeutically active agents. Consequently HCV NS3 serine protease is also an attractive target for drug discovery.

There are not currently any satisfactory anti-HCV agents or treatments. Until recently, the only established therapy for HCV disease was interferon treatment. However, interferons have significant side effects [M. A. Wlaker et al., "Hepatitis C Virus: An Overview of Current Approaches and Progress," DDT, 4, pp. 518-29 (1999); D. Moradpour et al., "Current and Evolving Therapies for Hepatitis C," Eur. J. Gastroenterol. Hepatol., 11, pp. 1199-1202 (1999); H. L. A. Janssen et al. "Suicide Associated with Alfa-Interferon Therapy for Chronic Viral Hepatitis," J. Hepatol., 21, pp. 241-243 (1994); P. F. Renault et al., "Side Effects of Alpha Interferon," Seminars in Liver Disease, 9, pp. 273-277. (1989)] and induce long term remission in only a fraction (~25%) of cases [O. Weiland, "Interferon Therapy in Chronic Hepatitis C Virus Infection", FEMS Microbiol. Rev., 14, pp. 279-288 (1994)]. Recent introductions of the pegylated forms of interferon (PEG-Intron® and Pegasys®) and the combination therapy of ribavirin and pegylated interferon (Rebetrol®) have resulted in only modest improvements in remission rates and only partial reductions in side effects. Moreover, the prospects for effective anti-HCV vaccines remain uncertain.

Thus, there is a need for more effective anti-HCV therapies. Such inhibitors would have therapeutic potential as protease inhibitors, particularly as serine protease inhibitors, and more particularly as HCV NS3 protease inhibitors. Specifically, such compounds may be useful as antiviral agents, particularly as anti-HCV agents.

SUMMARY OF THE INVENTION

The present invention addresses these needs by providing a compound of formula I:

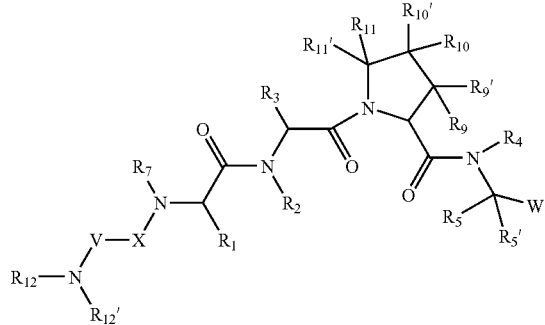

I or a pharmaceutically acceptable salt thereof, wherein the variables are as defined herein.

The invention also relates to compounds of formula I-1:

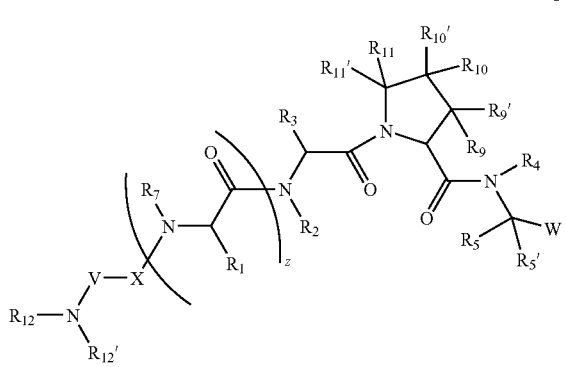

I-1 or pharmaceutically acceptable salts thereof, wherein the variables are as defined herein.

The invention also relates to compositions that comprise the above compounds and the use thereof. Such compositions may be used to pre-treat invasive devices to be inserted into a patient, to treat biological samples, such as blood, prior to administration to a patient, and for direct administration to a patient. In each case the composition will be used to inhibit HCV replication and to lessen the risk of or the severity of HCV infection.

The invention also relates to processes for preparing the compounds of formula I.

DETAILED DESCRIPTION OF THE INVENTION

The present invention provides a compound of formula I:

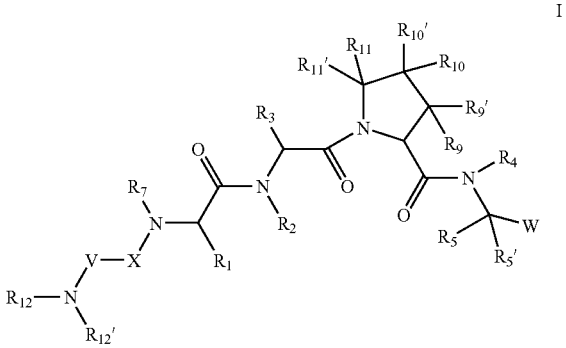

I or a pharmaceutically acceptable salt thereof, wherein:
$R_9$ and $R_{9'}$ are independently:
  hydrogen-,
  (C1-C12)-aliphatic-,
  (C3-C10)-cycloalkyl- or -cycloalkenyl-,
  [(C3-C10)-cycloalkyl or -cycloalkenyl]-(C1-C12)-aliphatic-,
  (C6-C10)-aryl-,
  (C6-C10)-aryl-(C1-C12)aliphatic-,
  (C3-C10)-heterocyclyl-,
  (C3-C10)-heterocyclyl-(C1-C12)aliphatic-,
  (C5-C10)-heteroaryl-, or
  (C5-C10)-heteroaryl-(C1-C12)-aliphatic-;
    wherein up to three aliphatic carbon atoms in each of $R_9$ and $R_{9'}$ may be replaced by O, N, NH, S, SO, or $SO_2$;
    wherein each of $R_9$ and $R_{9'}$ is independently and optionally substituted with up to 3 substituents independently selected from J;
  J is halogen, —OR', —$NO_2$, —CN, —$CF_3$, —$OCF_3$, —R', oxo, thioxo, =N(R'), =N(OR'), 1,2-methylenedioxy, 1,2-ethylenedioxy, —N(R')$_2$, —SR', —SOR', —$SO_2$R', —$SO_2$N(R')$_2$, —$SO_3$R', —C(O)R', —C(O)C(O)R', —C(O)C(O)OR', —C(O)C(O)N(R')$_2$, —C(O)CH$_2$C(O)R', —C(S)R', —C(S)OR', —C(O)OR', —OC(O)R', —C(O)N(R')$_2$, —OC(O)N(R')$_2$, —C(S)N(R')$_2$, —(CH$_2$)$_{0-2}$NHC(O)R', —N(R')N(R')COR', —N(R')N(R')C(O)OR', —N(R')N(R')CON(R')$_2$, —N(R')$SO_2$R', —N(R')$SO_2$N(R')$_2$, —N(R')C(O)OR', —N(R')C(O)R', —N(R') C(S)R', —N(R') C(O)N(R')$_2$, —N(R') C(S)N(R')$_2$, —N(COR')COR', —N(OR')R', —C(=NH)N(R')$_2$, —C(O)N(OR')R', —C(=NOR')R', —OP(O)(OR')$_2$, —P(O)(R')$_2$, —P(O)(OR')$_2$, or —P(O)(H)(OR');
wherein;
R' is independently selected from:
  hydrogen-,
  (C1-C12)-aliphatic-,
  (C3-C10)-cycloalkyl- or -cycloalkenyl-,
  [(C3-C10)-cycloalkyl or -cycloalkenyl]-(C1-C12)-aliphatic-,
  (C6-C10)-aryl-,
  (C6-C10)-aryl-(C1-C12)aliphatic-,
  (C3-C10)-heterocyclyl-,
  (C3-C10)-heterocyclyl-(C1-C12)aliphatic-,
  (C5-C10)-heteroaryl-, or
  (C5-C10)-heteroaryl-(C1-C12)-aliphatic-;

wherein up to 5 atoms in R' are optionally and independently substituted with J;
wherein two R' groups bound to the same atom optionally form a 3- to 10-membered aromatic or non-aromatic ring having up to 3 heteroatoms independently selected from N, NH, O, S, SO, and $SO_2$, wherein said ring is optionally fused to a (C6-C10)aryl, (C5-C10)heteroaryl, (C3-C10)cycloalkyl, or a (C3-C10)heterocyclyl, wherein any ring has up to 3 substituents selected independently from J;

$R_{10}$, $R_{10'}$, $R_{11}$, and $R_{11'}$ are each independently:
hydrogen-,
(C1-C12)-aliphatic-,
(C3-C10)-cycloalkyl- or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C3-C10)-heterocyclyl-(C1-C12)aliphatic-,
(C5-C10)-heteroaryl-, or
(C5-C10)-heteroaryl-(C1-C12)-aliphatic-;
wherein any ring is optionally fused to a (C6-C10)aryl, (C5-C10)heteroaryl, (C3-C10)cycloalkyl, or (C3-C10)heterocyclyl;
wherein up to 3 aliphatic carbon atoms in each of $R_{10}$, $R_{10'}$, $R_{11}$, and $R_{11'}$ may be replaced by a heteroatom selected from O, NH, S, SO, or $SO_2$ in a chemically stable arrangement;
wherein each of $R_{10}$, $R_{10'}$, $R_{11}$, and $R_{11'}$ is independently and optionally substituted with up to 3 substituents independently selected from J; or $R_{10}$ is —OR' and $R_{10'}$ is H; or
$R_{10}$ and $R_{10'}$ are both —OR' or —SR'; or
$R_{10}$ and $R_{10'}$ are both fluorine; or
$R_{10}$ and $R_{10'}$ are taken together with the carbon atom to which they are bound to form a 5- to 7-membered saturated or partially unsaturated ring;
wherein the $R_{10}$ and $R_{10'}$ atoms bound to the carbon atom are independently C(H), N, NH, O, S, SO, or $SO_2$;
wherein said ring may contain up to 4 heteroatoms independently selected from N, NH, O, S, SO, and $SO_2$;
wherein any atom is optionally singly or multiply substituted with up to 2 substituents selected independently from J; and
wherein said ring is optionally fused to a second ring selected from (C6-C10)aryl, (C5-C10)heteroaryl, (C3-C10)cycloalkyl, and a (C3-C10)heterocyclyl, wherein said second ring has up to 3 substituents selected independently from J; or $R_9$ and $R_{10}$ are taken together with the ring atoms to which they are bound to form a 3- to 6-membered aromatic or non-aromatic ring having up to 3 heteroatoms independently selected from N, NH, O, S, SO, or $SO_2$;
wherein said ring is optionally substituted with up to 3 substituents selected independently from J; or $R_{10}$ and $R_{11}$ are taken together with the ring atoms to which they are bound to form a 3- to 6-membered aromatic or non-aromatic ring having up to 3 heteroatoms independently selected from N, NH, O, S, SO, or $SO_2$; wherein said ring is optionally substituted with up to 3 substituents selected independently from J; or $R_9$ and $R_{11}$ are taken together with the ring atoms to which they are bound to form a bridged bicyclic saturated or partially unsaturated carbocyclic or heterocyclic ring system containing up to 10 atoms; wherein said ring system is optionally substituted with up to 3 substituents selected independently from J; wherein each heteroatom in the heterocyclic ring system is selected from the group consisting of N, NH, O, S, SO, or $SO_2$;

$R_1$ and $R_3$ are independently:
(C1-C12)-aliphatic-,
(C3-C10)-cycloalkyl- or -cycloalkenyl-,
[(C3-C10)-cycloalkyl- or -cycloalkenyl]-(C1-C12)-aliphatic-,
(C6-C10)-aryl-(C1-C12)aliphatic-, or
(C5-C10)-heteroaryl-(C1-C12)-aliphatic-;
wherein up to 3 aliphatic carbon atoms in each of $R_1$ and $R_3$ may be replaced by a heteroatom selected from O, N, NH, S, SO, or $SO_2$ in a chemically stable arrangement;
wherein each of $R_1$ and $R_3$ is independently and optionally substituted with up to 3 substituents independently selected from J;

$R_2$, $R_4$, and $R_7$ are each independently:
hydrogen-,
(C1-C12)-aliphatic-,
(C3-C10)-cycloalkyl-(C1-C12)-aliphatic-, or
(C6-C10)-aryl-(C1-C12)-aliphatic-;
wherein up to two aliphatic carbon atoms in each of $R_2$, $R_4$, and $R_7$ may be replaced by a heteroatom selected from O, N, NH, S, SO, and $SO_2$ in a chemically stable arrangement;
wherein each of $R_2$, $R_4$, and $R_7$ is optionally substituted with up to 3 substituents independently selected from J;

$R_5$ and $R_{5'}$ are independently hydrogen or (C1-C12)-aliphatic, wherein any hydrogen is optionally replaced with halogen; wherein any terminal carbon atom of $R_5$ is optionally substituted with sulfhydryl or hydroxy; or $R_5$ is Ph or —$CH_2$Ph and $R_{5'}$ is H, wherein said Ph or —$CH_2$Ph group is optionally substituted with up to 3 substituents independently selected from J; or $R_5$ and $R_{5'}$ together with the atom to which they are bound optionally form a 3- to 6-membered saturated or partially unsaturated ring having up to 2 heteroatoms selected from N, NH, O, SO, and $SO_2$; wherein said ring is optionally substituted with up to 2 substituents selected independently from J;

W is:

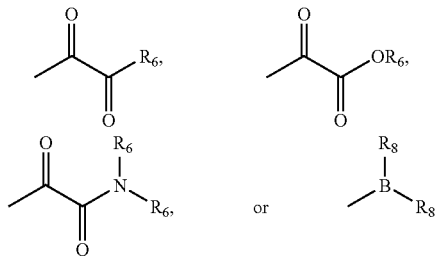

wherein each $R_6$ is independently:
hydrogen-,
(C1-C12)-aliphatic-,
(C6-C10)-aryl-,
(C6-C10)-aryl-(C1-C12)aliphatic-,
(C3-C10)-cycloalkyl- or cycloalkenyl-,
[(C3-C10)-cycloalkyl- or cycloalkenyl]-(C1-C12)-aliphatic-,
(C3-C10)-heterocyclyl-,
(C3-C10)-heterocyclyl-(C1-C12)-aliphatic-, (C5-C10)-heteroaryl-, or (C5-C10)-heteroaryl-(C1-C12)-aliphatic-, wherein $R_6$ is optionally substituted with up to 3 J substituents; or two $R_6$ groups, together with the nitrogen atom to which they are bound, optionally form a 3- to 10-membered aromatic or non-aromatic ring having up to 3 heteroatoms independently selected from N, NH, O, S, SO, and $SO_2$, wherein said ring is optionally fused to a (C6-C10) aryl, (C5-C10)heteroaryl, (C3-C10)cycloalkyl, or a (C3-C10)heterocyclyl, wherein any ring has up to 3 substituents selected independently from J;

wherein each $R_8$ is independently —OR'; or the $R_8$ groups together with the boron atom, optionally form a (C3-C10)-membered heterocyclic ring having in addition to the boron up to 3 additional heteroatoms selected from N, NR', O, SO, and $SO_2$;

X is —C(O)—, —S(O)—, or —S(O)$_2$—,

V is —C(O)—, —S(O)—, —S(O)$_2$—, or —N($R_{13}$)—;

wherein $R_{13}$ is:

hydrogen-, (C1-C12)-aliphatic-, (C3-C10)-cycloalkyl- or -cycloalkenyl-,

[(C3-C10)-cycloalkyl or -cycloalkenyl]-(C1-C12)-aliphatic-, (C6-C10)-aryl-, (C6-C10)-aryl-(C1-C12)aliphatic-, (C3-C10)-heterocyclyl-, (C3-C10)-heterocyclyl-(C1-C12)aliphatic-, (C5-C10)-heteroaryl-, or (C5-C10)-heteroaryl-(C1-C12)-aliphatic-;

wherein up to two aliphatic carbon atoms in $R_{13}$ may be replaced by a heteroatom selected from O, N, NH, S, SO, and $SO_2$ in a chemically stable arrangement;

wherein $R_{13}$ is independently and optionally substituted with up to 3 substituents independently selected from J;

$R_{12}$ and $R_{12'}$ are independently:

hydrogen;

(C1-C12)-aliphatic-;

(C6-C10)-aryl-, (C6-C10)-aryl-(C1-C12)aliphatic-, (C3-C10)-cycloalkyl or -cycloalkenyl-,

[(C3-C10)-cycloalkyl or -cycloalkenyl]-(C1-C12)-aliphatic-, (C3-C10)-heterocyclyl-, (C3-C10)-heterocyclyl-(C1-C12)-aliphatic-, (C5-C10)-heteroaryl-, or (C5-C10)-heteroaryl-(C1-C12)-aliphatic-;

wherein up to 3 aliphatic carbon atoms in each of $R_{12}$ or $R_{12'}$ may be replaced by a heteroatom selected from O, N, NH, S, SO, or $SO_2$ in a chemically stable arrangement;

wherein each of $R_{12}$ or $R_{12'}$ is optionally substituted with up to 3 substituents independently selected from J; or $R_{12}$ and $R_{12'}$ together with the nitrogen atom to which they are bound, form a (C3-C10)-heterocyclic ring;

wherein said (C3-C10)-heterocyclic ring is optionally substituted with up to 3 substituents independently selected from J.

The present invention also provides a compound of formula I-1:

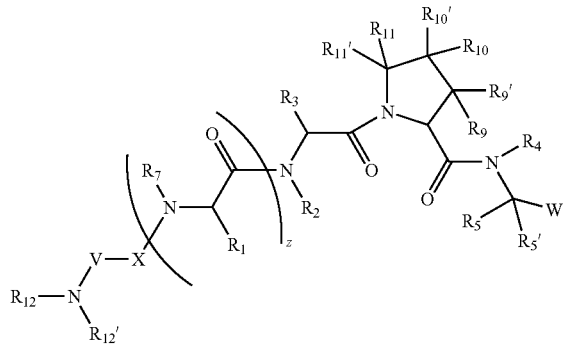

I-1 or a pharmaceutically acceptable salt thereof, wherein:

z is 0 or 1;

$R_9$ and $R_{9'}$ are independently:

hydrogen-, (C1-C12)-aliphatic-, (C3-C10)-cycloalkyl- or -cycloalkenyl-,

[(C3-C10)-cycloalkyl or -cycloalkenyl]-(C1-C12)-aliphatic-, (C6-C10)-aryl-, (C6-C10)-aryl-(C1-C12)aliphatic-, (C3-C10)-heterocyclyl-, (C3-C10)-heterocyclyl-(C1-C12)aliphatic-, (C5-C10)-heteroaryl-, or (C5-C10)-heteroaryl-(C1-C12)-aliphatic-;

wherein up to three aliphatic carbon atoms in each of $R_9$ and $R_{9'}$ may be replaced by O, N, NH, S, SO, or $SO_2$;

wherein each of $R_9$ and $R_{9'}$ is independently and optionally substituted with up to 3 substituents independently selected from J;

J is halogen, —OR', —NO$_2$, —CN, —CF$_3$, —OCF$_3$, —R', oxo, thioxo, =N(R'), =N(OR'), 1,2-methylenedioxy, 1,2-ethylenedioxy, —N(R')$_2$, —SR', —SOR', —SO$_2$R', —SO$_2$N(R')$_2$, —SO$_3$R', —C(O)R', —C(O)C(O)R', —C(O)C(O)OR', —C(O)C(O)N(R')$_2$, —C(O)CH$_2$C(O)R', —C(S)R', —C(S)OR', —C(O)OR', —OC(O)R', —C(O)N(R')$_2$, —OC(O)N(R')$_2$, —C(S)N(R')$_2$, —(CH$_2$)$_{0-2}$NHC(O)R', —N(R')N(R')COR', —N(R') N(R') C(O)OR', —N(R') N(R') CON(R')$_2$, —N(R') SO$_2$R', —N(R')SO$_2$N(R')$_2$, —N(R')C(O)OR', —N(R')C(O)R', —N(R') C(S)R', —N(R') C(O)N(R')$_2$, —N(R') C(S)N(R')$_2$, —N(COR')COR', —N(OR')R', —C(=NH)N(R')$_2$, —C(O)N(OR')R', —C(=NOR')R', —OP(O) (OR')$_2$, —P(O)(R')$_2$, —P(O)(OR')$_2$, or —P(O)(H)(OR');

wherein;

R' is independently selected from:

hydrogen-, (C1-C12)-aliphatic-, (C3-C10)-cycloalkyl- or -cycloalkenyl-,

[(C3-C10)-cycloalkyl or -cycloalkenyl]-(C1-C12)-aliphatic-, (C6-C10)-aryl-, (C6-C10)-aryl-(C1-C12)aliphatic-, (C3-C10)-heterocyclyl-, (C3-C10)-heterocyclyl-(C1-C12)aliphatic-, (C5-C10)-heteroaryl-, or (C5-C10)-heteroaryl-(C1-C12)-aliphatic-;

wherein up to 5 atoms in R' are optionally and independently substituted with J;

wherein two R' groups bound to the same atom optionally form a 3- to 10-membered aromatic or non-aromatic ring having up to 3 heteroatoms independently selected from N, NH, O, S, SO, and $SO_2$, wherein said ring is optionally fused to a (C6-C10) aryl, (C5-C10)heteroaryl, (C3-C10)cycloalkyl, or a (C3-C10)heterocyclyl, wherein any ring has up to 3 substituents selected independently from J;

$R_{10}$, $R_{10'}$, $R_{11}$, and $R_{11'}$ are each independently:
  hydrogen-,
  (C1-C12)-aliphatic-,
  (C3-C10)-cycloalkyl- or -cycloalkenyl-,
  [(C3-C10)-cycloalkyl or -cycloalkenyl]-(C1-C12)-aliphatic-,
  (C6-C10)-aryl-,
  (C6-C10)-aryl-(C1-C12)aliphatic-,
  (C3-C10)-heterocyclyl-,
  (C3-C10)-heterocyclyl-(C1-C12)aliphatic-,
  (C5-C10)-heteroaryl-, or
  (C5-C10)-heteroaryl-(C1-C12)-aliphatic-;
    wherein any ring is optionally fused to a (C6-C10)aryl, (C5-C10)heteroaryl, (C3-C10)cycloalkyl, or (C3-C10)heterocyclyl;
    wherein up to 3 aliphatic carbon atoms in each of $R_{10}$, $R_{10'}$, $R_{11}$, and $R_{11'}$ may be replaced by a heteroatom selected from O, NH, S, SO, or $SO_2$ in a chemically stable arrangement;
    wherein each of $R_{10}$, $R_{10'}$, $R_{11}$, and $R_{11'}$ is independently and optionally substituted with up to 3 substituents independently selected from J; or $R_{10}$ is —OR' and $R_{10'}$ is H; or
$R_{10}$ and $R_{10'}$ are both —OR' or —SR'; or
$R_{10}$ and $R_{10'}$ are both fluorine; or
$R_{10}$ and $R_{10'}$ are taken together with the carbon atom to which they are bound to form a 5- to 7-membered saturated or partially unsaturated ring;
  wherein the $R_{10}$ and $R_{10'}$ atoms bound to the carbon atom are independently C(H), N, NH, O, S, SO, or $SO_2$;
  wherein said ring may contain up to 4 heteroatoms independently selected from N, NH, O, S, SO, and $SO_2$;
  wherein any atom is optionally singly or multiply substituted with up to 2 substituents selected independently from J; and
  wherein said ring is optionally fused to a second ring selected from (C6-C10)aryl, (C5-C10)heteroaryl, (C3-C10)cycloalkyl, and a (C3-C10)heterocyclyl, wherein said second ring has up to 3 substituents selected independently from J; or $R_9$ and $R_{10}$ are taken together with the ring atoms to which they are bound to form a 3- to 6-membered aromatic or non-aromatic ring having up to 3 heteroatoms independently selected from N, NH, O, S, SO, or $SO_2$;
  wherein said ring is optionally substituted with up to 3 substituents selected independently from J; or $R_{10}$ and $R_{11}$ are taken together with the ring atoms to which they are bound to form a 3- to 6-membered aromatic or non-aromatic ring having up to 3 heteroatoms independently selected from N, NH, O, S, SO, or $SO_2$;
  wherein said ring is optionally substituted with up to 3 substituents selected independently from J; or $R_9$ and $R_{11}$ are taken together with the ring atoms to which they are bound to form a bridged bicyclic saturated or partially unsaturated carbocyclic or heterocyclic ring system containing up to 10 atoms; wherein said ring system is optionally substituted with up to 3 substituents selected independently from J; wherein each heteroatom in the heterocyclic ring system is selected from the group consisting of N, NH, O, S, SO, or $SO_2$;

$R_1$ (if present) and $R_3$ are independently:
  (C1-C12)-aliphatic-,
  (C3-C10)-cycloalkyl- or -cycloalkenyl-,
  [(C3-C10)-cycloalkyl- or -cycloalkenyl]-(C1-C12)-aliphatic-,
  (C6-C10)-aryl-(C1-C12)aliphatic-, or
  (C5-C10)-heteroaryl-(C1-C12)-aliphatic-;
    wherein up to 3 aliphatic carbon atoms in each of $R_1$ (if present) and $R_3$ may be replaced by a heteroatom selected from O, N, NH, S, SO, or $SO_2$ in a chemically stable arrangement;
    wherein each of $R_1$ (if present) and $R_3$ is independently and optionally substituted with up to 3 substituents independently selected from J;

$R_2$, $R_4$, and $R_7$ (if present) are each independently:
  hydrogen-,
  (C1-C12)-aliphatic-,
  (C3-C10)-cycloalkyl-(C1-C12)-aliphatic-, or
  (C6-C10)-aryl-(C1-C12)-aliphatic-;
    wherein up to two aliphatic carbon atoms in each of $R_2$, $R_4$, and $R_7$ (if present) may be replaced by a heteroatom selected from O, N, NH, S, SO, and $SO_2$ in a chemically stable arrangement;
    wherein each of $R_2$, $R_4$, and $R_7$ (if present) is optionally substituted with up to 3 substituents independently selected from J;

$R_5$ and $R_{5'}$ are independently hydrogen or (C1-C12)-aliphatic, wherein any hydrogen is optionally replaced with halogen; wherein any terminal carbon atom of $R_5$ is optionally substituted with sulfhydryl or hydroxy; or $R_5$ is Ph or —$CH_2$Ph and $R_{5'}$ is H, wherein said Ph or —$CH_2$Ph group is optionally substituted with up to 3 substituents independently selected from J; or $R_5$ and $R_{5'}$ together with the atom to which they are bound optionally form a 3- to 6-membered saturated or partially unsaturated ring having up to 2 heteroatoms selected from N, NH, O, SO, and $SO_2$; wherein said ring is optionally substituted with up to 2 substituents selected independently from J;

W is:

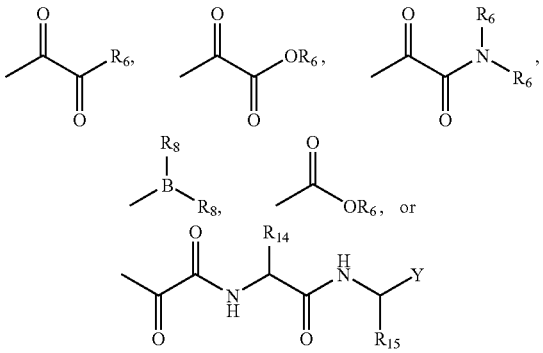

wherein
Y is —$CO_2H$, a derivative of —$CO_2H$, or a bioisostere of —$CO_2H$;
each $R_6$ is independently:
  hydrogen-,
  (C1-C12)-aliphatic-,
  (C6-C10)-aryl-, (C6-C10)-aryl-(C1-C12)aliphatic-,
(C3-C10)-cycloalkyl- or cycloalkenyl-,
[(C3-C10)-cycloalkyl- or cycloalkenyl]-(C1-C12)-aliphatic-,
(C3-C10)-heterocyclyl-,
(C3-C10)-heterocyclyl-(C1-C12)-aliphatic-,
(C5-C10)-heteroaryl-, or
(C5-C10)-heteroaryl-(C1-C12)-aliphatic-,
wherein $R_6$ is optionally substituted with up to 3 J substituents; or
two $R_6$ groups, together with the nitrogen atom to which they are bound, optionally form a 3- to 10-membered aromatic or non-aromatic ring having up to 3 heteroatoms independently selected from N, NH, O, S, SO, and $SO_2$, wherein said ring is optionally fused to a (C6-C10) aryl, (C5-C10)heteroaryl, (C3-C10)cycloalkyl, or a (C3-C10)heterocyclyl, wherein any ring has up to 3 substituents selected independently from J;
wherein each $R_8$ is independently —OR'; or the $R_8$ groups together with the boron atom, optionally form a (C3-C10)-membered heterocyclic ring having in addition to the boron up to 3 additional heteroatoms selected from N, NR', O, SO, and $SO_2$;
X is —C(O)—, —S(O)—, or —S(O)$_2$—,
V is —C(O)—, —S(O)—, —S(O)$_2$—, or —N($R_{13}$)—;
wherein $R_{13}$ is:
hydrogen-,
(C1-C12)-aliphatic-,
(C3-C10)-cycloalkyl- or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C3-C10)-heterocyclyl-(C1-C12)aliphatic-,
(C5-C10)-heteroaryl-, or
(C5-C10)-heteroaryl-(C1-C12)-aliphatic-;
wherein up to two aliphatic carbon atoms in $R_{13}$ may be replaced by a heteroatom selected from O, N, NH, S, SO, and $SO_2$ in a chemically stable arrangement;
wherein $R_{13}$ is independently and optionally substituted with up to 3 substituents independently selected from J;
$R_{12}$ and $R_{12'}$ are independently:
hydrogen;
(C1-C12)-aliphatic-;
(C6-C10)-aryl-,
(C6-C10)-aryl-(C1-C12)aliphatic-,
(C3-C10)-cycloalkyl or -cycloalkenyl-,
[(C3-C10)-cycloalkyl or -cycloalkenyl]-(C1-C12)-aliphatic-,
(C3-C10)-heterocyclyl-,
(C3-C10)-heterocyclyl-(C1-C12)-aliphatic-,
(C5-C10)-heteroaryl-, or
(C5-C10)-heteroaryl-(C1-C12)-aliphatic-;
wherein up to 3 aliphatic carbon atoms in each of $R_{12}$ or $R_{12'}$ may be replaced by a heteroatom selected from O, N, NH, S, SO, or $SO_2$ in a chemically stable arrangement;
wherein each of $R_{12}$ or $R_{12'}$ is optionally substituted with up to 3 substituents independently selected from J; or
$R_{12}$ and $R_{12'}$ together with the nitrogen atom to which they are bound, form a (C3-C10)-heterocyclic ring;

wherein said (C3-C10)-heterocyclic ring is optionally substituted with up to 3 substituents independently selected from J; and
$R_{14}$ and $R_{15}$ are independently:
(C1-C12)-aliphatic-,
(C3-C10)-cycloalkyl- or -cycloalkenyl-,
[(C3-C10)-cycloalkyl- or -cycloalkenyl]-(C1-C12)-aliphatic-,
(C6-C10)-aryl-(C1-C12)aliphatic-,
(C5-C10)-heteroaryl-(C1-C12)aliphatic-,
wherein up to 3 aliphatic carbon atoms in $R_{14}$ and $R_{15}$ may be replaced by a heteroatom selected from O, N, NH, S, SO, or $SO_2$ in a chemically stable arrangement;
wherein each of $R_{14}$ and $R_{15}$ is independently and optionally substituted at each substitutable position with up to 3 substituents independently selected from J.

Definitions

The term "aryl" as used herein means a monocyclic or bicyclic carbocyclic aromatic ring system. Phenyl is an example of a monocyclic aromatic ring system. Bicyclic aromatic ring systems include systems wherein both rings are aromatic, e.g., naphthyl, and systems wherein only one of the two rings is aromatic, e.g., tetralin. It is understood that as used herein, the term "(C6-C10)-aryl-" includes any one of a C6, C7, C8, C9, and C10 monocyclic or bicyclic carbocyclic aromatic ring system.

The term "bioisostere" —$CO_2H$ as used in herein refers to a chemical moiety which may substitute for a carboxylic acid group in a biologically active molecule. Examples of such groups are disclosed in Christopher A. Lipinski, "Bioisosteres in Drug Design" Annual Reports in Medicinal Chemistry, 21, pp. 286-88 (1986), and in C. W. Thornber, "Isosterism and Molecular Modification in Drug Design" Chemical Society Reviews, pp. 563-580 (1979). Examples of such groups include, but are not limited to, —COCH$_2$OH, —CONHOH, SO$_2$NHR', —SO$_3$H, —PO(OH)NH$_2$, —CONHCN, —OSO$_3$H, —CONHSO$_2$R', —PO(OH)$_2$, —PO(OH)(OR'), —PO(OH)(R'), —OPO(OH)$_2$, —OPO(OH)(OR'), —OPO(OH)(R'), HNPO(OH)$_2$, —NHPO(OH)(OR'), —NHPO(OH)(R')

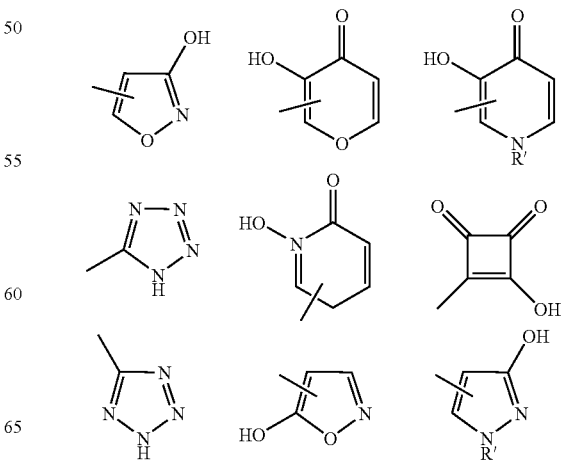

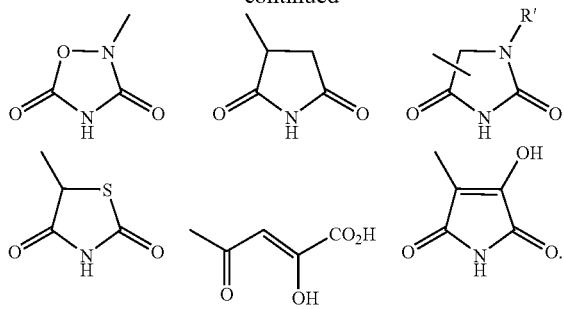

The term "heterocyclyl" as used herein means a monocyclic or bicyclic non-aromatic ring system having 1 to 3 heteroatom or heteroatom groups in each ring selected from O, N, NH, S, SO, and $SO_2$ in a chemically stable arrangement. In a bicyclic non-aromatic ring system embodiment of "heterocyclyl" one or both rings may contain said heteroatom or heteroatom groups. It is understood that as used herein, the term "(C5-C10)-heterocyclyl-" includes any one of a 5, 6, 7, 8, 9, and 10 atom monocyclic or bicyclic non-aromatic ring system having 1 to 3 heteroatoms or heteroatom groups in each ring selected from O, N, NH, and S in a chemically stable arrangement.

Examples of heterocyclic rings include 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

The term "heteroaryl" as used herein means a monocyclic or bicyclic aromatic ring system having 1 to 3 heteroatoms or heteroatom groups in each ring selected from O, N, NH, and S in a chemically stable arrangement. In such a bicyclic aromatic ring system embodiment of "heteroaryl":
one or both rings may be aromatic; and
one or both rings may contain said heteroatom or heteroatom groups. It is understood that as used herein, the term "(C5-C10)-heteroaryl-" includes any one of a 5, 6, 7, 8, 9, and 10 atom monocyclic or bicyclic aromatic ring system having 1 to 3 heteroatoms or heteroatom groups in each ring selected from O, N, NH, and S in a chemically stable arrangement.

Examples of heteroaryl rings include 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "aliphatic" as used herein means a straight chained or branched alkyl, alkenyl or alkynyl. It is understood that as used herein, the term "(C1-C12)-aliphatic-" includes any one of a C1, C2, C3, C4, C5, C6, C7, C8, C9, C10, C11, and C12 straight or branched alkyl chain of carbon atoms. It is also understood that alkenyl or alkynyl embodiments need at least two carbon atoms in the aliphatic chain. The term "cycloalkyl or cycloalkenyl" refers to a monocyclic or fused or bridged bicyclic carbocyclic ring system that is not aromatic. Cycloalkenyl rings have one or more units of unsaturation. It is also understood that as used herein, the term "(C3-C10)-cycloalkyl- or -cycloalkenyl-" includes any one of a C3, C4, C5, C6, C7, C8, C9, and C10 monocyclic or fused or bridged bicyclic carbocyclic ring. Preferred cycloalkyl groups include cyclopropyl, cyclobutyl, cyclopentyl, cyclohexyl, cyclohexenyl, cycloheptyl, cycloheptenyl, nornbornyl, adamantyl and decalin-yl.

As used herein, the carbon atom designations may have the indicated integer and any intervening integer. For example, the number of carbon atoms in a (C1-C4)-alkyl group is 1, 2, 3, or 4. It should be understood that these designation refer to the total number of atoms in the appropriate group. For example, in a (C3-C10)-heterocyclyl the total number of carbon atoms and heteroatoms is 3 (as in aziridine), 4, 5, 6 (as in morpholine), 7, 8, 9, or 10.

The phrase "chemically stable arrangement" as used herein refers to a compound structure that renders the compound sufficiently stable to allow manufacture and administration to a mammal by methods known in the art. Typically, such compounds are stable at a temperature of 40° C. or less, in the absence of moisture or other chemically reactive condition, for at least a week.

Embodiments

According to one embodiment for compounds of formula I or formula I-1, the

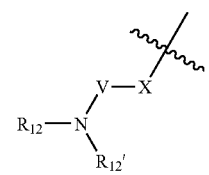

radical is:

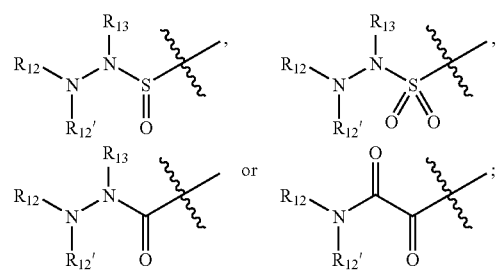

wherein:
$R_{12}$, $R_{12'}$, and $R_{13}$ are as defined in any of the embodiments herein.

According to another embodiment for compounds of formula I or formula I-1, the

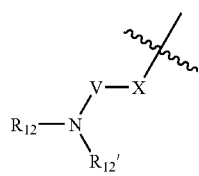

radical is:

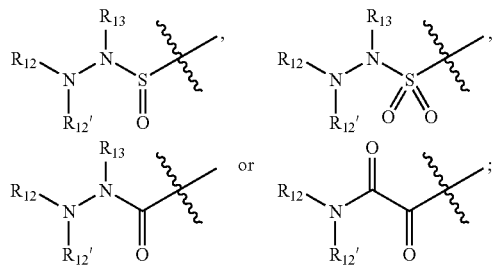

wherein:
R$_{12'}$ is hydrogen;
R$_{12}$ is:
(C1-C12)-aliphatic-;
(C6-C10)-aryl-,
(C6-C10)-aryl-(C1-C12)aliphatic-,
(C3-C10)-cycloalkyl or -cycloalkenyl-,
[(C3-C10)-cycloalkyl or -cycloalkenyl]-(C1-C12)-aliphatic-,
(C3-C10)-heterocyclyl-,
(C3-C10)-heterocyclyl-(C1-C12)-aliphatic-,
(C5-C10)-heteroaryl-, or
(C5-C10)-heteroaryl-(C1-C12)-aliphatic-;
 wherein up to 3 aliphatic carbon atoms in R$_{12}$ may be replaced by a heteroatom selected from O, N, NH, S, SO, or SO$_2$ in a chemically stable arrangement;
 wherein R$_{12}$ is optionally substituted with up to 3 substituents independently selected from J; and
R$_{13}$ is as defined in any of the embodiments herein.

According to another embodiment for compounds of formula I or formula I-1, the

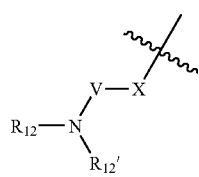

radical is:

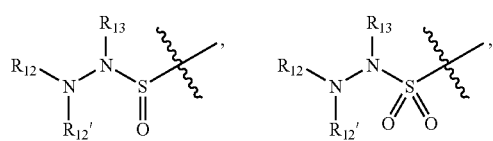

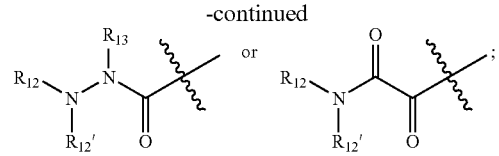

wherein:
R$_{12'}$ is hydrogen;
R$_{12}$ is:
(C1-C12)-aliphatic-;
(C6-C10)-aryl-(C1-C12)aliphatic-, or
(C3-C10)-cycloalkyl or -cycloalkenyl-;
 wherein up to 3 aliphatic carbon atoms in R$_{12}$ may be replaced by a heteroatom selected from O, N, NH, S, SO, or SO$_2$ in a chemically stable arrangement;
 wherein R$_{12}$ is optionally substituted with up to 3 substituents independently selected from J; and
R$_{13}$ is as defined in any of the embodiments herein.

According to another embodiment for compounds of formula I or formula I-1, the

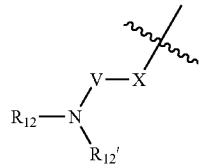

radical is:

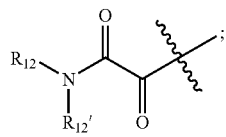

wherein:
R$_{12'}$ is hydrogen; and
R$_{12}$ is:
(C1-C12)-aliphatic-;
(C6-C10)-aryl-(C1-C12)aliphatic-, or
(C3-C10)-cycloalkyl or -cycloalkenyl-;
 wherein up to 3 aliphatic carbon atoms in R$_{12}$ may be replaced by a heteroatom selected from O, N, NH, S, SO, or SO$_2$ in a chemically stable arrangement; and
 wherein R$_{12}$ is optionally substituted with up to 3 substituents independently selected from J.

According to another embodiment for compounds of formula I and formula I-1, the

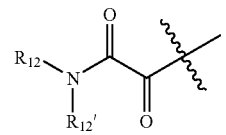

radical is;

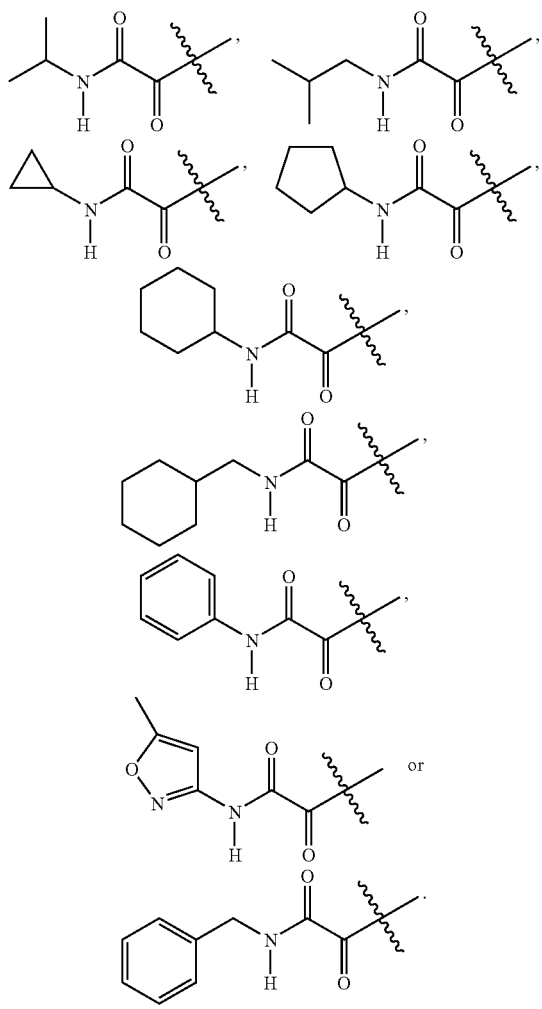

In another embodiment for compounds of formula I or formula I-1, the

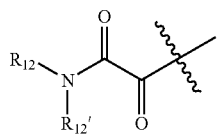

radical is;

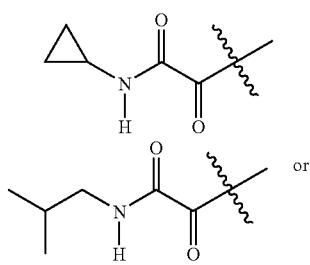

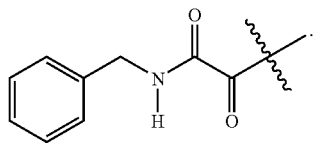

According to another embodiment, the present invention provides a compound of formula IA:

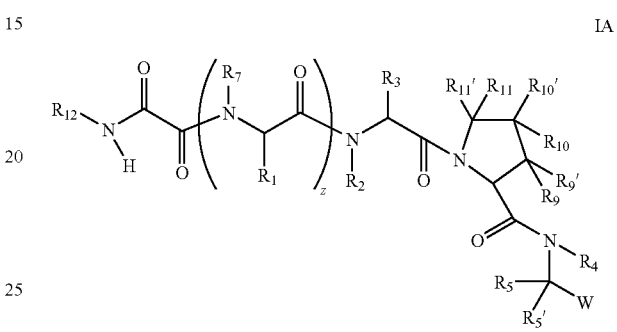

IA wherein:

$R_1, R_2, R_3, R_4, R_5, R_{5'}, R_7, R_9, R_{9'}, R_{10}, R_{10'}, R_{11}, R_{11'}, R_{12}$, z, and W are as defined in any of the embodiments herein.

According to one embodiment for compounds of formula IA, z is one, W is selected from:

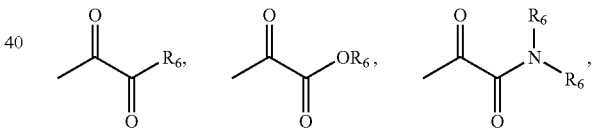

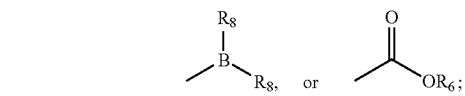

and $R_6$ and $R_8$ are as defined in any of the embodiments herein.

According to another embodiment for compounds of formula IA, z is 0, W is selected from:

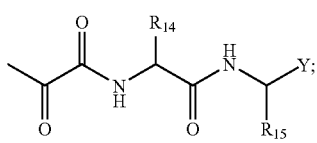

and $R_{14}$ and $R_{15}$ are as defined in any of the embodiments herein.

According to another embodiment for compounds of formula I or formula I-1, the

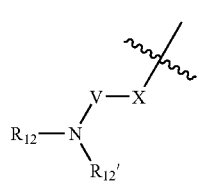

radical is:

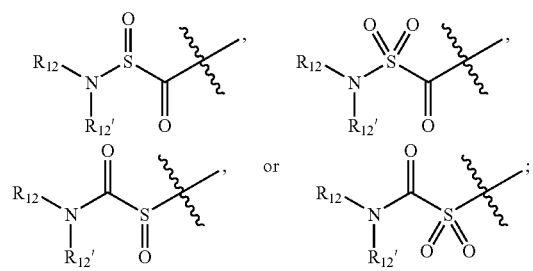

wherein:
R$_{12}$, and R$_{12'}$ are as defined in any of the embodiments herein.

According to another embodiment for compounds of formula I or formula I-1, the

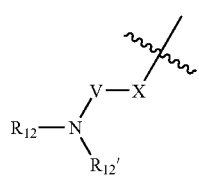

radical is:

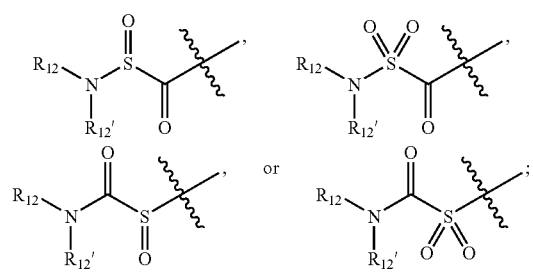

wherein:
R$_{12'}$ is hydrogen; and
R$_{12}$ is:
(C1-C12)-aliphatic-;
(C6-C10)-aryl-(C1-C12)aliphatic-, or
(C3-C10)-cycloalkyl or -cycloalkenyl-;
  wherein up to 3 aliphatic carbon atoms in R$_{12}$ may be replaced by a heteroatom selected from O, N, NH, S, SO, or SO$_2$ in a chemically stable arrangement; and
  wherein R$_{12}$ is optionally substituted with up to 3 substituents independently selected from J.

In certain embodiments of formula I, wherein z is 1 and the

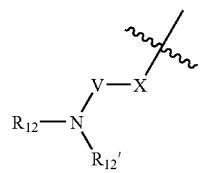

radical is attached to N(R$_7$), R$_7$ is hydrogen.

In certain embodiments of formula I-1, wherein z is 1 and the

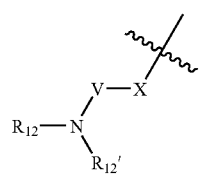

radical is attached to N(R$_7$), R$_7$ is hydrogen.

In certain other embodiments for compounds of formula I-1, wherein z is 0 and the

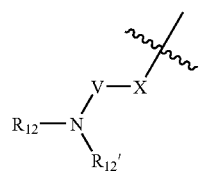

radical is attached to N(R$_2$), R$_2$ is hydrogen.

According to another embodiment for compounds of formula I or formula I-1, the

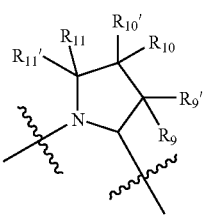

radical is:

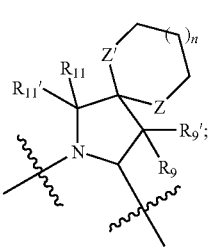

wherein:
n is 0, 1, or 2;
Z and Z' are independently C(H), N, NH, O, or S;

$R_9$, $R_{9'}$, $R_{11}$, and $R_{11'}$ are as defined in any of the embodiments herein; and the spirocyclic ring containing Z and Z' is optionally substituted with up to 3 J substituents, wherein J is as defined in any of the embodiments herein.

According to another embodiment for compounds of formula I or I-1, the

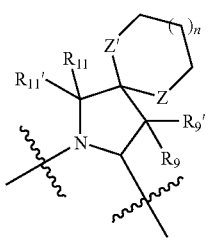

radical is:

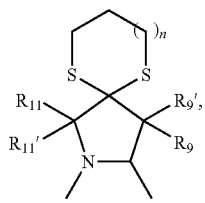 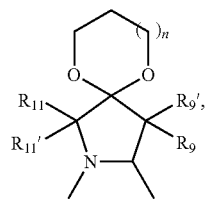

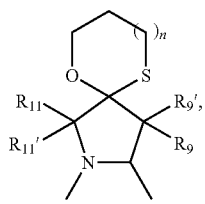 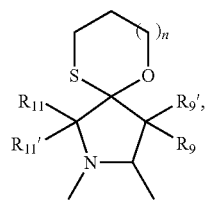

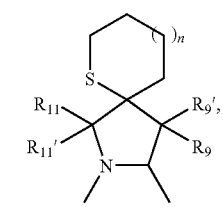 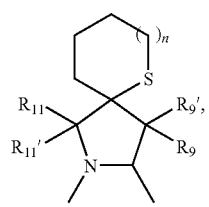

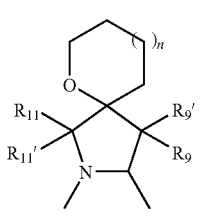 or 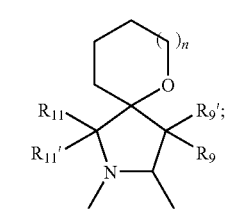

wherein:

$R_{11}$ and $R_{11'}$ are both H;

n is 0, 1, or 2;

$R_9$ and $R_{9'}$ are as defined in any of the embodiments herein; and the spirocyclic ring containing Z and Z' is optionally substituted with up to 3 J substituents, wherein J is as defined in any of the embodiments herein.

According to another embodiment for compounds of formula I or I-1, the

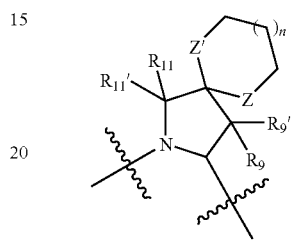

radical is:

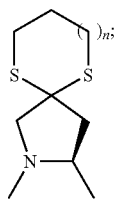

wherein:

n is 0 or 1.

According to another embodiment, the present invention provides a compound of formula IB:

IB

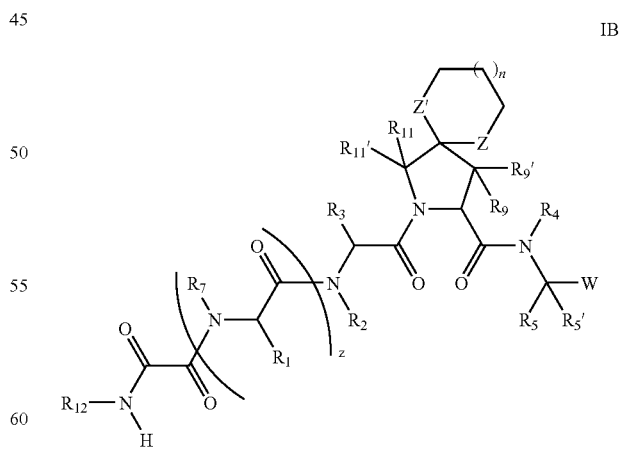

wherein:

$R_1$, $R_2$, $R_3$, $R_4$, $R_5$, $R_{5'}$, $R_7$, $R_9$, $R_{9'}$, $R_{11}$, $R_{11'}$, $R_{12}$, z, Z, Z', n, and W are as defined in any of the embodiments herein.

According to another embodiment, the present invention provides a compound of formula IB-1:

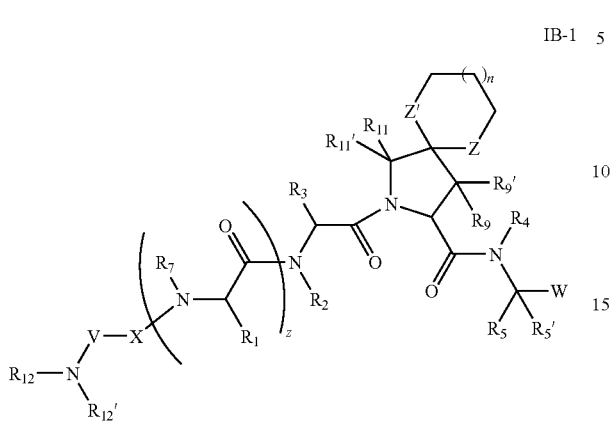

IB-1 wherein:
$R_1$, $R_2$, $R_3$, $R_4$, $R_5$, $R_{5'}$, $R_7$, $R_9$, $R_{9'}$, $R_{11}$, $R_{11'}$, $R_{12}$, $R_{12'}$, X, V, n, z, Z, Z', and W are as defined in any of the embodiments herein.

According to one embodiment for compounds of formula IB or formula IB-1, z is one, W is selected from:

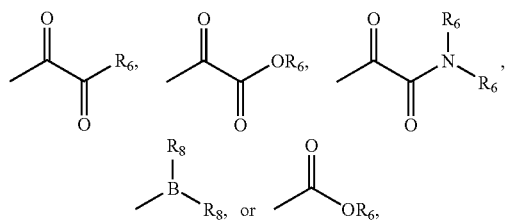

and $R_6$ and $R_8$ are as defined in any of the embodiments herein.

According to another embodiment for compounds of formula IB or formula IB-1, z is 0, W is selected from:

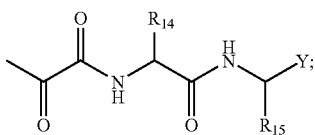

and $R_{14}$ and $R_{15}$ are as defined in any of the embodiments herein.

According to another embodiment for compounds of formula I or formula I-1, the radical is:

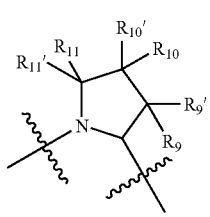

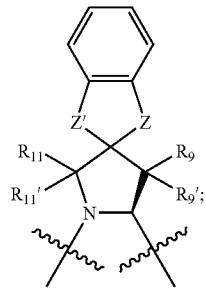

wherein:
Z and Z' are independently C(H), N, NH, O, or S;
$R_9$, $R_{9'}$, $R_{11}$, and $R_{11'}$ are as defined in any of the embodiments herein; and
the fused benzo ring is optionally substituted with up to 3 J substituents, wherein J is as defined in any of the embodiments herein.

According to another embodiment, the present invention provides a compound of formula IC:

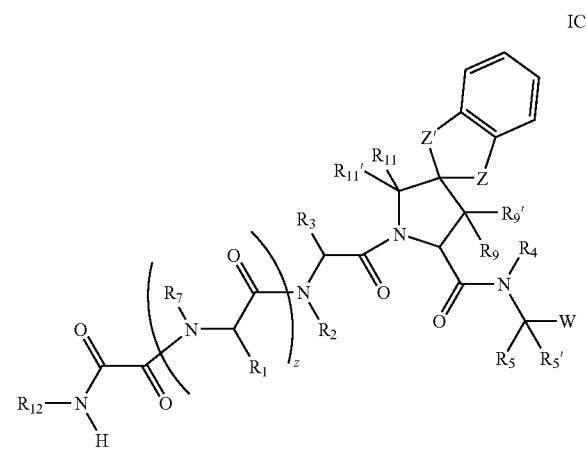

IC wherein:
$R_1$, $R_2$, $R_3$, $R_4$, $R_5$, $R_{5'}$, $R_7$, $R_9$, $R_{9'}$, $R_{11}$, $R_{11'}$, $R_{12}$, Z Z, Z', and W are as defined in any of the embodiments herein; and
the fused benzo ring is optionally substituted with up to 3 J substituents, wherein J is as defined in any of the embodiments herein.

According to another embodiment for compounds of formula IC, z is 1, Z and Z' are S, $R_9$, $R_{9'}$, $R_{11}$, and $R_{11'}$, are H, $R_1$, $R_2$, $R_3$, $R_4$, $R_5$, $R_{5'}$, $R_7$, $R_{12}$, and W are as defined in any of the embodiments herein and the fused benzo ring is optionally substituted with up to 3 J substituents, wherein J is as defined in any of the embodiments herein.

In another embodiment for compounds of formula IC, z is 0, Z and Z' are S, $R_9$, $R_{9'}$, $R_{11}$, and $R_{11'}$ are H, $R_1$, $R_2$, $R_3$, $R_4$, $R_5$, $R_{5'}$, $R_7$, $R_{12}$, and W are as defined in any of the embodiments herein and the fused benzo ring is optionally substituted with up to 3 J substituents, wherein J is as defined in any of the embodiments herein.

According to another embodiment, the present invention provides a compound of formula IC-1:

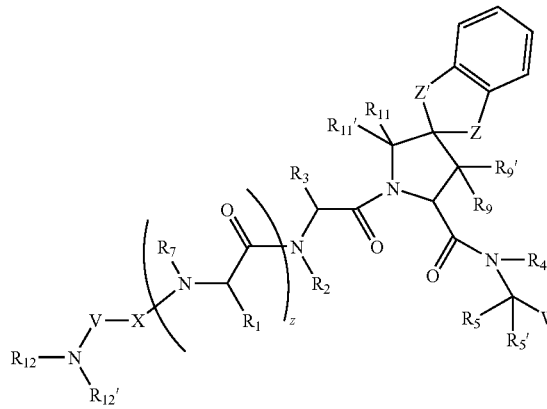

wherein:
R$_1$, R$_2$, R$_3$, R$_4$, R$_5$, R$_{5'}$, R$_7$, R$_9$, R$_{9'}$, R$_{11}$, R$_{11'}$, R$_{12}$, R$_{12'}$, X, V, z, Z, Z' and W are as defined in any of the embodiments herein; and the fused benzo ring is optionally substituted with up to 3 J substituents, wherein J is as defined in any of the embodiments herein.

According to another embodiment for compounds of formula IC-1, z is 1, Z and Z' are S, R$_9$, R$_{9'}$, R$_{11}$, and R$_{11'}$ are H, R$_1$, R$_2$, R$_3$, R$_4$, R$_5$, R$_{5'}$, R$_7$, R$_{12}$, R$_{12'}$, X, V, and W are as defined in any of the embodiments herein and the fused benzo ring is optionally substituted with up to 3 J substituents, wherein J is as defined in any of the embodiments herein.

In another embodiment for compounds of formula IC-1, z is 0, Z and Z' are S, R$_9$, R$_{9'}$, R$_{11}$, and R$_{11'}$ are H, R$_1$, R$_2$, R$_3$, R$_4$, R$_5$, R$_{5'}$, R$_7$, R$_{12}$, R$_{12'}$, X, V, and W are as defined in any of the embodiments herein and the fused benzo ring is optionally substituted with up to 3 J substituents, wherein J is as defined in any of the embodiments herein.

According to yet another embodiment for compounds of formula IC or formula IC-1, z is one, W is selected from:

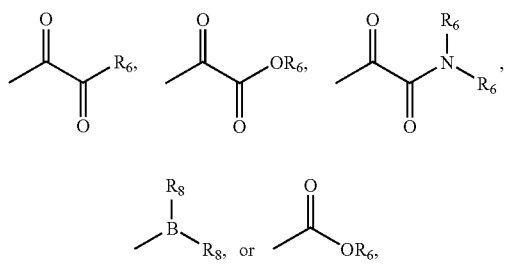

and R$_6$ and R$_8$ are as defined in any of the embodiments herein.

According to still another embodiment for compounds of formula IC or formula IC-1, z is 0, W is selected from:

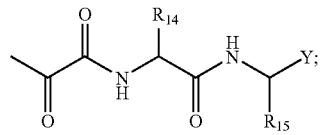

and R$_{14}$ and R$_{15}$ are as defined in any of the embodiments herein.

According to another embodiment for compounds of formula I or formula I-1, the

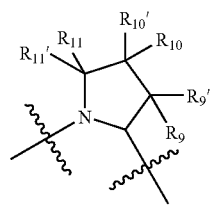

radical is:

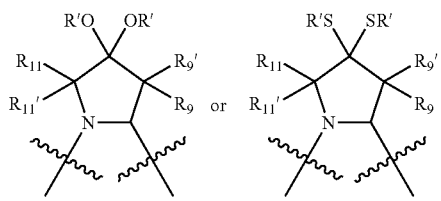

wherein:
R$_9$, R$_{9'}$, R$_{11}$, and R$_{11'}$ are H; and
R' is selected from:
hydrogen-,
(C1-C12)-aliphatic-,
(C3-C10)-cycloalkyl- or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C3-C10)-heterocyclyl-(C1-C12)aliphatic-,
(C5-C10)-heteroaryl-, or (C5-C10)-heteroaryl-(C1-C12)-aliphatic-;
wherein up to 5 atoms in R' are optionally and independently substituted with J;

According to another embodiment for compounds of formula I or formula I-1, the

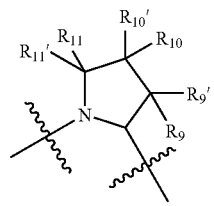

radical is:

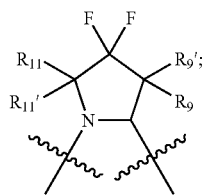

wherein:

$R_9$, $R_{9'}$, $R_{11}$, and $R_{11'}$ are H.

In yet another embodiment for compounds of formula I or formula I-1, the

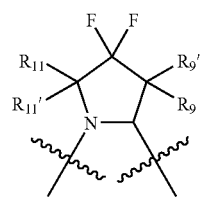

radical is:

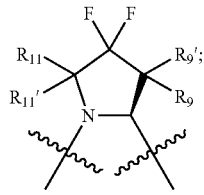

wherein:

$R_9$, $R_{9'}$, $R_{11}$, and $R_{11'}$ are H.

According to another embodiment, the present invention provides a compound of formula ID:

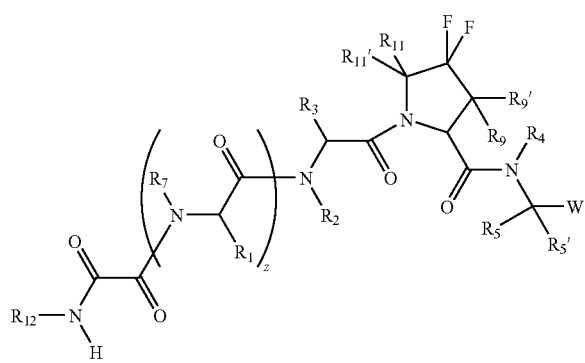

wherein:

$R_1$, $R_2$, $R_3$, $R_4$, $R_5$, $R_{5'}$, $R_7$, $R_9$, $R_{9'}$, $R_{11}$, $R_{11'}$, $R_{12}$, Z and W are as defined in any of the embodiments herein.

According to another embodiment, the present invention provides a compound of formula ID-1:

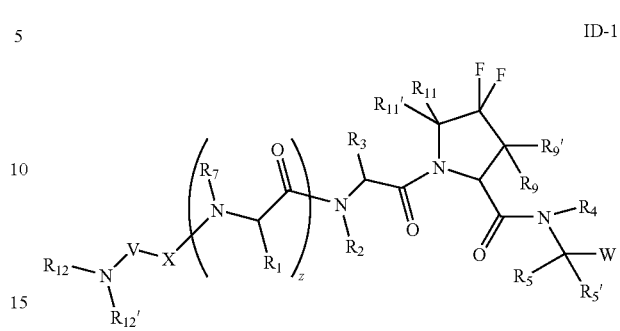

wherein:

$R_1$, $R_2$, $R_3$, $R_4$, $R_5$, $R_{5'}$, $R_7$, $R_9$, $R_{9'}$, $R_{11}$, $R_{11'}$, $R_{12}$, $R_{12'}$, X, V, z, and W are as defined in any of the embodiments herein.

According to one embodiment for compounds of formula ID or formula ID-1, z is 1.

According to another embodiment for compounds of formula ID or formula ID-1, z is 0.

According to yet another embodiment for compounds of formula ID or formula ID-1, z is one, W is selected from:

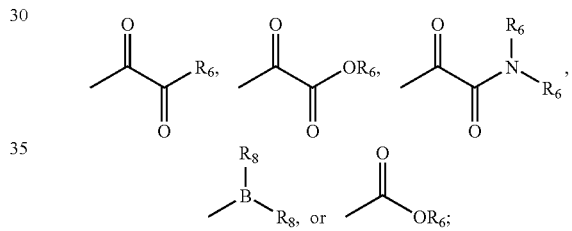

and $R_6$ and $R_8$ are as defined in any of the embodiments herein.

According to another embodiment for compounds of formula ID or formula ID-1, z is 0, W is selected from:

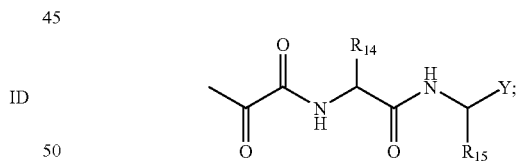

and $R_{14}$ and $R_{15}$ are as defined in any of the embodiments herein.

According to another embodiment for compounds of formula I or formula I-1, in the

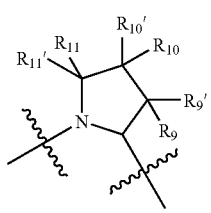

radical, $R_9$, $R_{10}$, $R_{10'}$, $R_{11}$, and $R_{11'}$ are H; and $R_{9'}$ is:
(C1-C12)-aliphatic-,
(C3-C10)-cycloalkyl- or -cycloalkenyl-,
(C6-C10)-aryl-,
(C3-C10)-heterocyclyl-, or
(C5-C10)-heteroaryl-;
wherein up to three aliphatic carbon atoms in $R_{9'}$ may be replaced by O, N, NH, S, SO, or $SO_2$;
wherein $R_{9'}$ is independently and optionally substituted with up to 3 substituents independently selected from J.

According to another embodiment for compounds of formula I or formula I-1, the

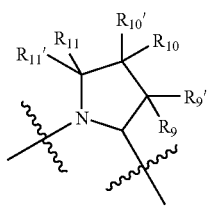

radical is:

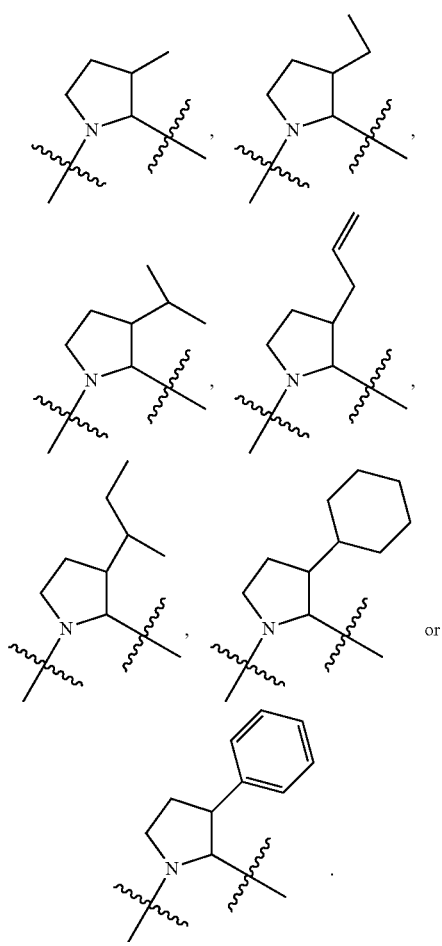

According to another embodiment for compounds of formula I or formula I-1, in the

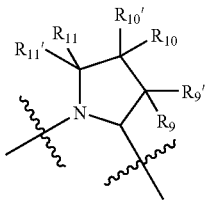

radical $R_9$, $R_{9'}$, $R_{10}$, $R_{11}$, and $R_{11'}$ are H; and $R_{10'}$ is:
(C1-C12)-aliphatic-,
(C3-C10)-cycloalkyl- or -cycloalkenyl-,
(C6-C10)-aryl-,
wherein any ring is optionally fused to a (C6-C10)aryl, (C5-C10)heteroaryl, (C3-C10)cycloalkyl, or (C3-C10) heterocyclyl;
wherein up to 3 aliphatic carbon atoms in $R_{10'}$ may be replaced by a heteroatom selected from O, NH, S, SO, or $SO_2$ in a chemically stable arrangement;
wherein $R_{10'}$ is independently and optionally substituted with up to 3 substituents independently selected from J.

According to another embodiment for compounds of formula I or formula I-1, the

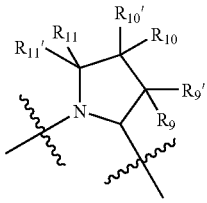

radical is:

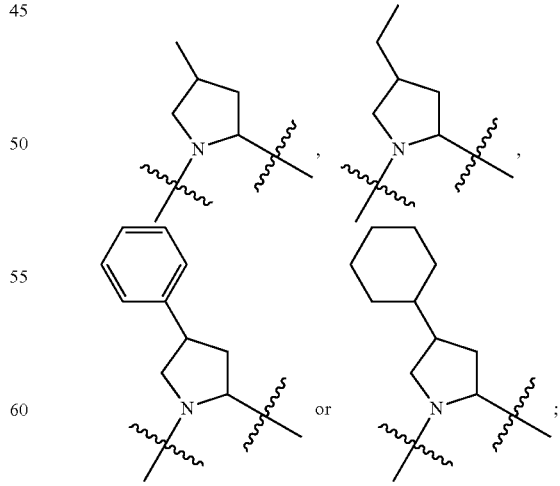

wherein the $R_{10'}$ group, is independently and optionally substituted with up to 3 substituents independently selected from J.

According to yet another embodiment for compounds of formula I or formula I-1, in the

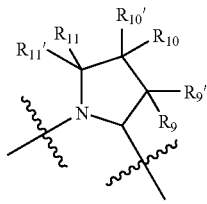

radical

R$_9$, R$_{9'}$, R$_{10}$, R$_{10'}$ and R$_{11}$ are H; and

R$_{11'}$ is:

(C1-C12)-aliphatic-, (C3-C10)-cycloalkyl- or -cycloalkenyl-, (C6-C10)-aryl-, wherein any ring is optionally fused to a (C6-C10)aryl, (C5-C10)heteroaryl, (C3-C10)cycloalkyl, or (C3-C10) heterocyclyl;

wherein up to 3 aliphatic carbon atoms in R$_{11'}$ may be replaced by a heteroatom selected from O, NH, S, SO, or SO$_2$ in a chemically stable arrangement;

wherein R$_{11'}$ is independently and optionally substituted with up to 3 substituents independently selected from J.

According to another embodiment for compounds of formula I or formula I-1, the

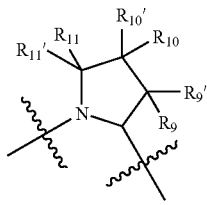

radical is:

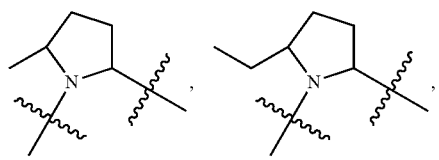

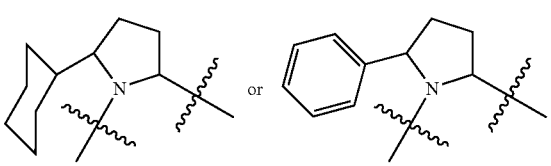

According to another embodiment for compounds of formula I or formula I-1, in the

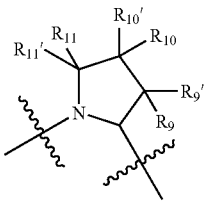

radical

R$_9$, R$_{10}$, R$_{11}$, and R$_{11'}$ are H; and

R$_{9'}$ and R$_{10'}$ are:

(C1-C12)-aliphatic-, (C3-C10)-cycloalkyl- or -cycloalkenyl-, wherein up to 3 aliphatic carbon atoms in R$_{9'}$ and R$_{10'}$ may be replaced by a heteroatom selected from O, NH, S, SO, or SO$_2$ in a chemically stable arrangement;

wherein R$_{9'}$ and R$_{10'}$ are independently and optionally substituted with up to 3 substituents independently selected from J.

According to another embodiment for compounds of formula I or formula I-1, the

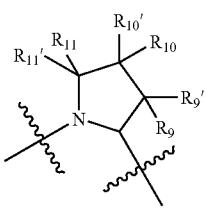

radical is:

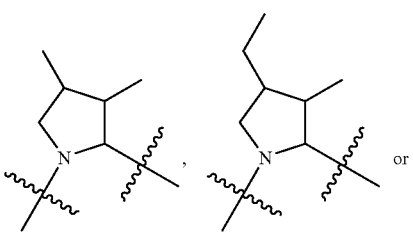

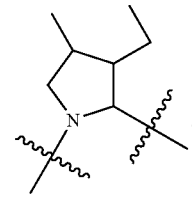

.

According to another embodiment for compounds of formula I or formula I-1, in the

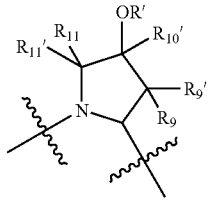

radical
R$_9$, R$_{9'}$, R$_{10'}$, R$_{11}$, and R$_{11'}$ are H; and
R' is selected from:
(C6-C10)-aryl-,
(C6-C10)-aryl-(C1-C12)aliphatic-,
(C3-C10)-heterocyclyl-,
(C3-C10)-heterocyclyl-(C1-C12)aliphatic-,
(C5-C10)-heteroaryl-, and
(C5-C10)-heteroaryl-(C1-C12)-aliphatic-;
wherein up to 5 atoms in R' are optionally and independently substituted with J.

According to another embodiment for compounds of formula I or formula I-1, the

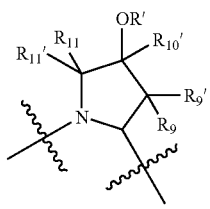

radical is:

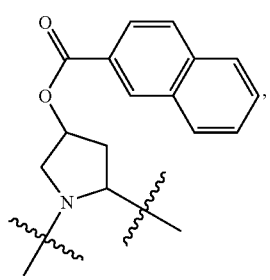

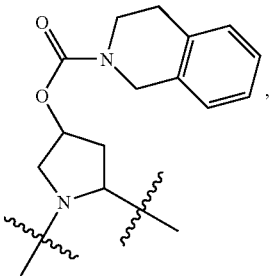

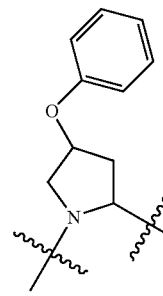

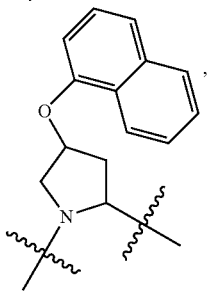

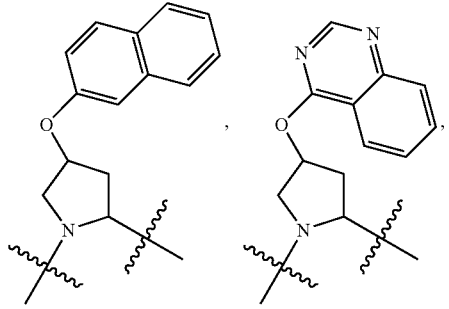

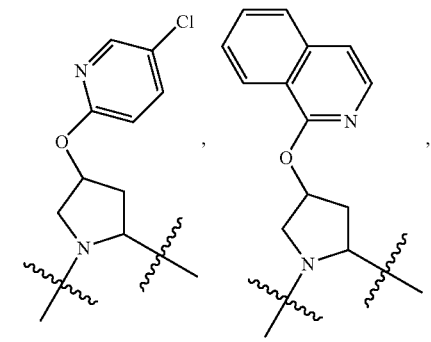

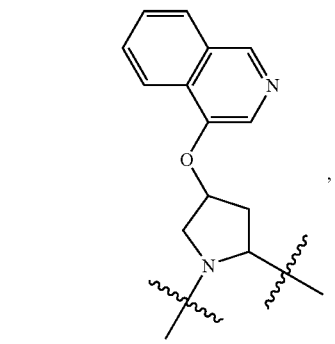

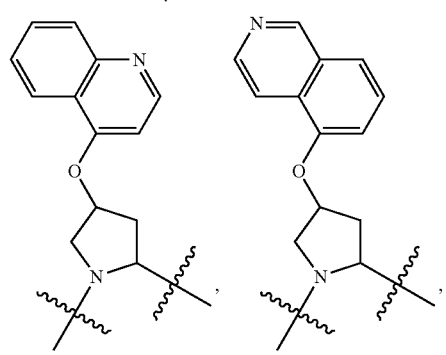

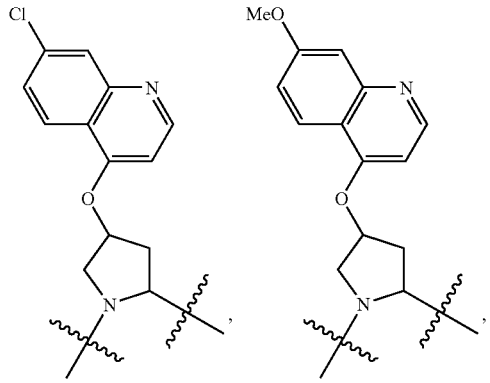

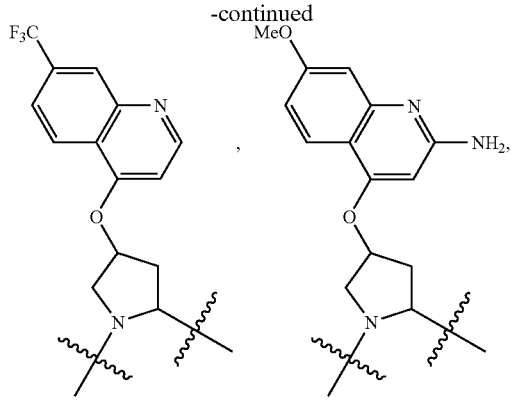 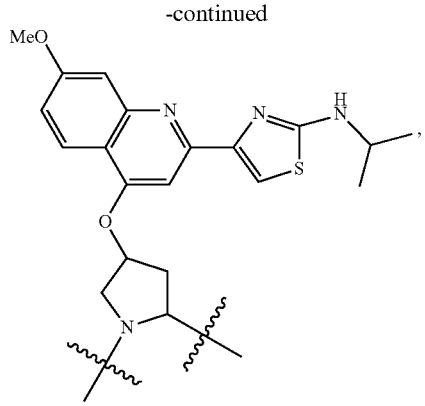
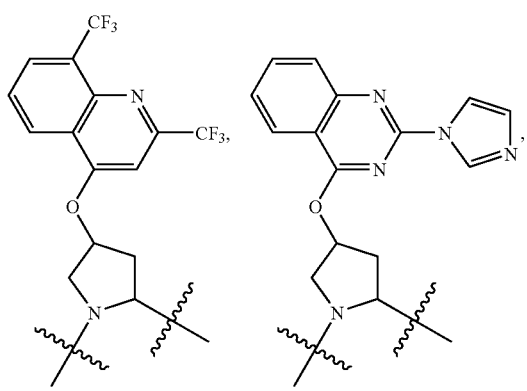 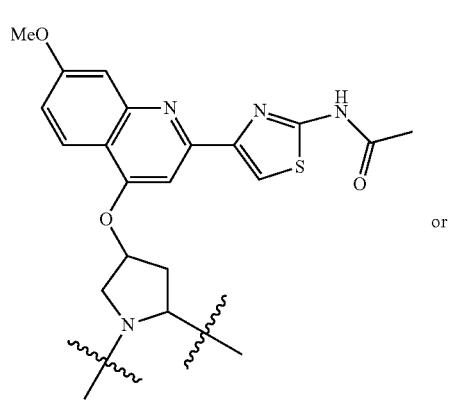
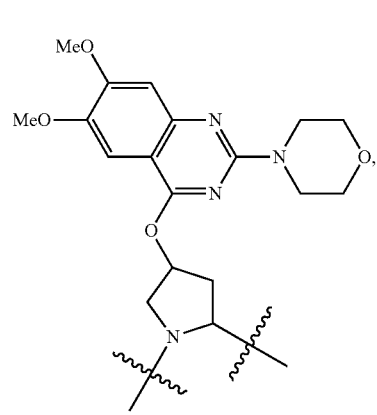 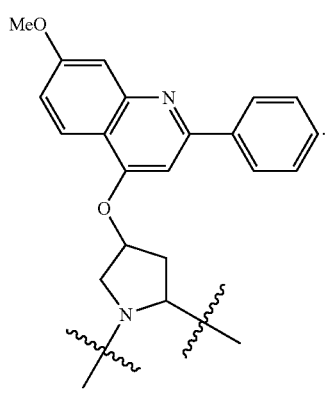 [SMILES: *C1CC(Oc2cc(-c3ccccc3)nc3cc(OC)ccc23)CN1*]
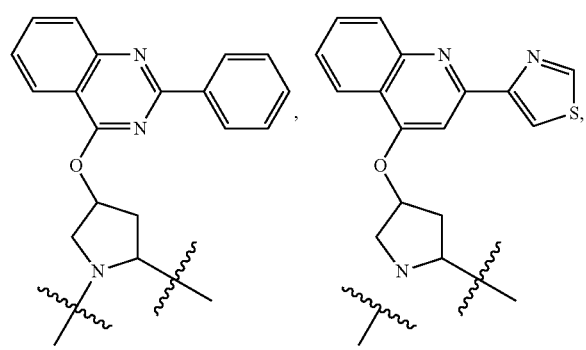
wherein up to 5 atoms in R' are optionally and independently substituted with J.
According to another embodiment for compounds of formula I or formula I-1, the
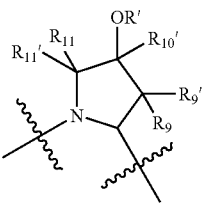

radical is:

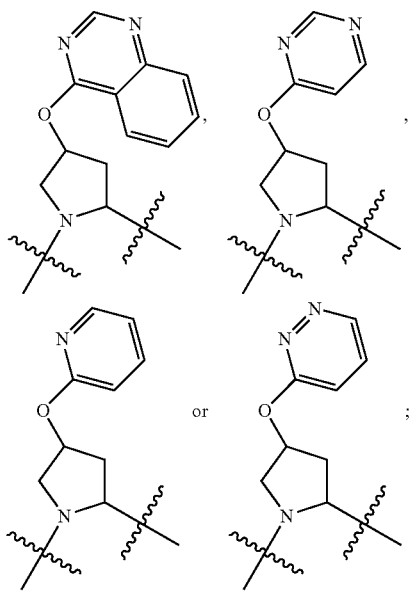

wherein up to 5 atoms in R' are optionally and independently substituted with J.

According to another embodiment for compounds of formula I or formula I-1, the radical is:

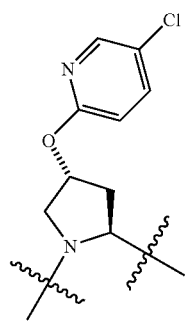

According to yet another embodiment for compounds of formula I or formula I-1, in the

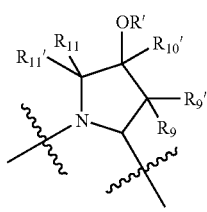

radical
$R_9$, $R_{9'}$, $R_{10'}$, $R_{11}$, and $R_{11'}$ are H; and
R' is selected from:
(C6-C10)-aryl-(C1-C12)aliphatic-,
(C3-C10)-heterocyclyl-(C1-C12)aliphatic-, and
(C5-C10)-heteroaryl-(C1-C12)-aliphatic-;
wherein up to 5 atoms in R' are optionally and independently substituted with J.

According to another embodiment for compounds of formula I or formula I-1, the

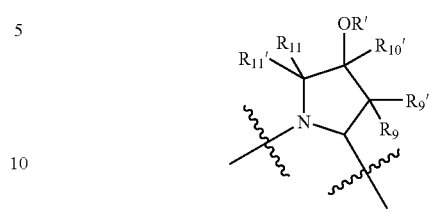

radical is:

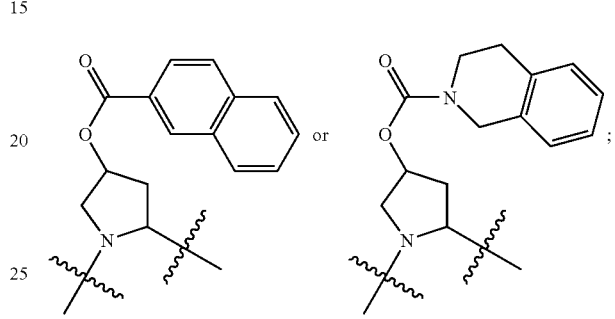

wherein up to 5 atoms in R' are optionally and independently substituted with J.

According to another embodiment, the present invention provides a compound of formula IE:

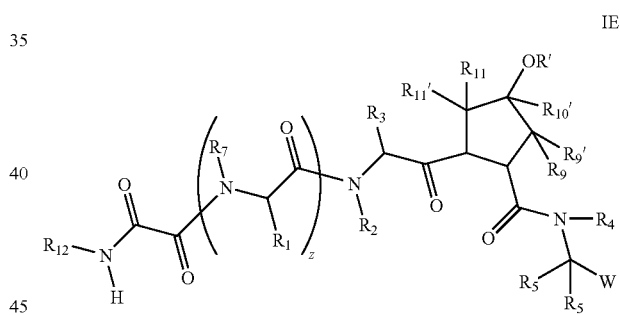

IE wherein:
$R_1$, $R_2$, $R_3$, $R_4$, $R_5$, $R_{5'}$, $R_7$, $R_9$, $R_{9'}$, $R_{10'}$, R', $R_{11}$, $R_{11'}$, $R_{12}$, z, and W are as defined in any of the embodiments herein.

According to another embodiment, the present invention provides a compound of formula IE-1:

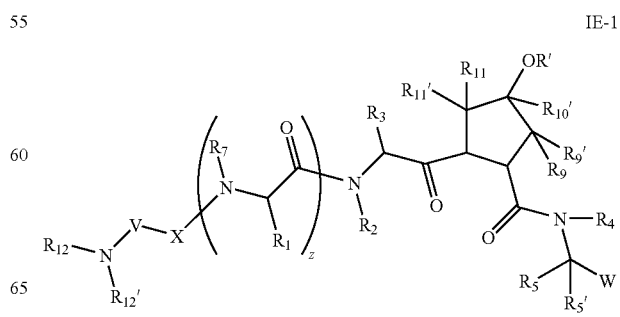

IE-1 wherein:
R$_1$, R$_2$, R$_3$, R$_4$, R$_5$, R$_{5'}$, R$_7$, R$_9$, R$_{9'}$, R$_{10'}$, R', R$_{11}$, R$_{11'}$, R$_{12}$, R$_{12'}$, z, X, V, and W are as defined in any of the embodiments herein.

According to one embodiment for compounds of formula IE or formula IE-1, z is 1.

According to another embodiment for compounds of formula IE or formula IE-1, z is 0.

According to yet another embodiment for compounds of formula IE or formula IE-1, z is one, W is selected from:

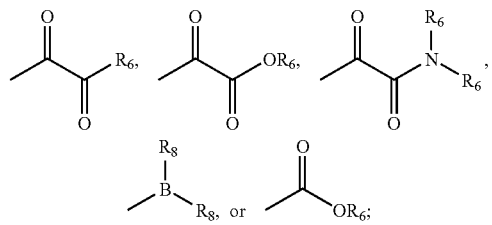

and R$_6$ and R$_8$ are as defined in any of the embodiments herein.

According to another embodiment for compounds of formula IE or formula IE-1, z is 0, W is selected from:

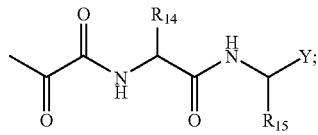

and R$_{14}$ and R$_{15}$ are as defined in any of the embodiments herein.

According to another embodiment for compounds of formula I or formula I-1, the

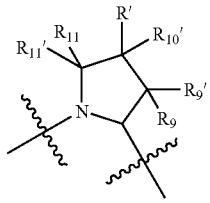

radical is:

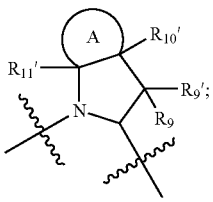

wherein;
ring A is a 5- to 6-membered aromatic or 3- to 6-membered non-aromatic ring having up to 3 heteroatoms independently selected from N, NH, O, SO, or SO$_2$;
wherein said ring A is optionally fused to a (C6-C10)aryl, (C5-C10)heteroaryl, (C3-C10)cycloalkyl, or (C3-C10) heterocyclyl;

wherein any ring has up to 3 substituents selected independently from J; and

R$_9$, R$_{9'}$, R$_{10'}$, and R$_{11'}$ are as defined in any of the embodiments herein.

According to another embodiment for compounds of formula I or formula I-1, the

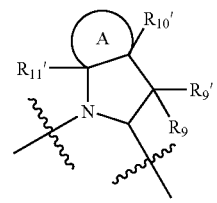

radical is:

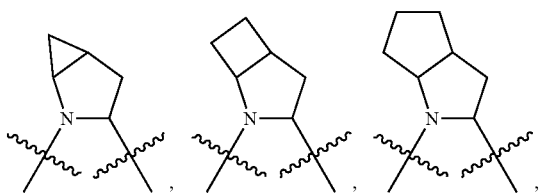

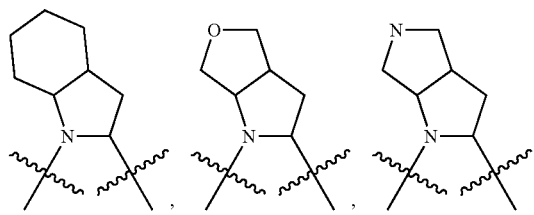

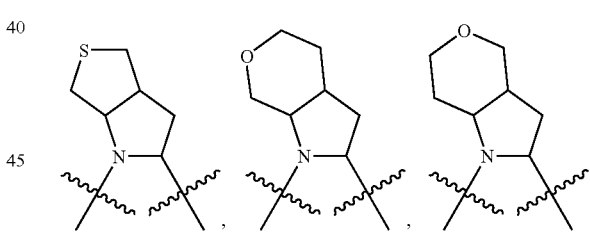

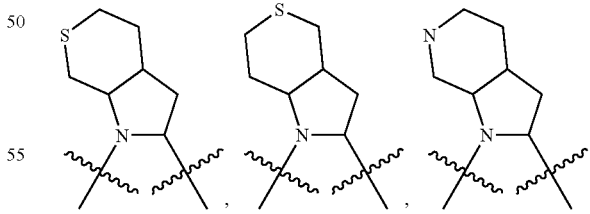

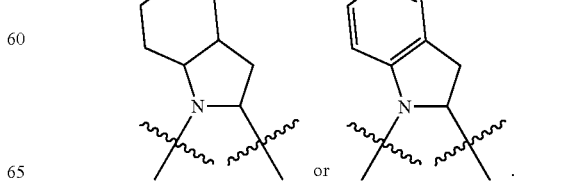

According to another embodiment for compounds of formula I or formula I-1, the

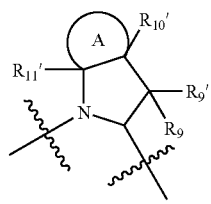

radical is:

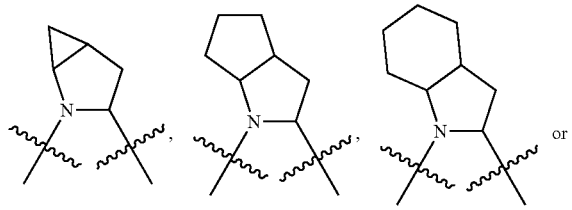

According to another embodiment for compounds of formula I or formula I-1, the

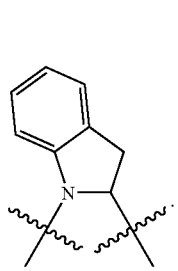

radical is:

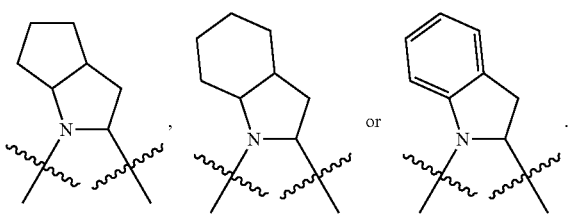 [SMILES: *C1CC2CCCC2N1* ; *C1CC2CCCCC2N1* ; *C1Cc2ccccc2N1*]

According to yet another embodiment for compounds of formula I or formula I-1, the

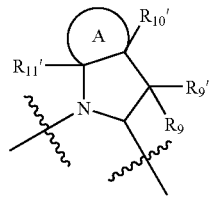

radical is:

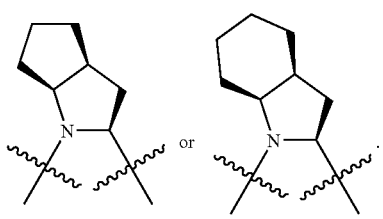 [SMILES: *[C@@H]1C[C@@H]2CCC[C@@H]2N1* ; *[C@@H]1C[C@@H]2CCCC[C@@H]2N1*]

According to another embodiment, the present invention provides a compound of formula IF:

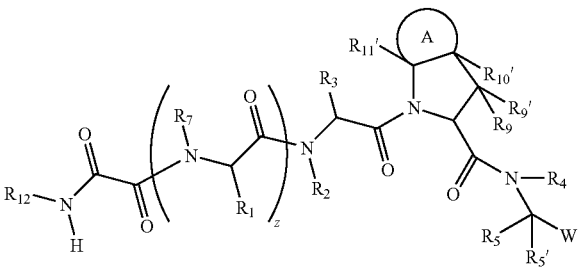

IF wherein:
R$_1$, R$_2$, R$_3$, R$_4$, R$_5$, R$_5'$, R$_7$, R$_9$, R$_9'$, R$_{10'}$, R$_{11'}$, R$_{12}$, z, W and ring A are as defined in any of the embodiments herein.

According to another embodiment, the present invention provides a compound of formula IF-1:

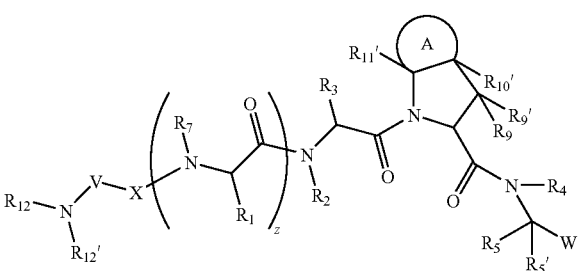

IF-1 wherein:
R$_1$, R$_2$, R$_3$, R$_4$, R$_5$, R$_5'$, R$_7$, R$_9$, R$_9'$, R$_{10'}$, R$_{11'}$, R$_{12}$, R$_{12'}$, z, X, V, W, and ring A are as defined in any of the embodiments herein.

According to another embodiment, the present invention provides a compound of formula IF-2:

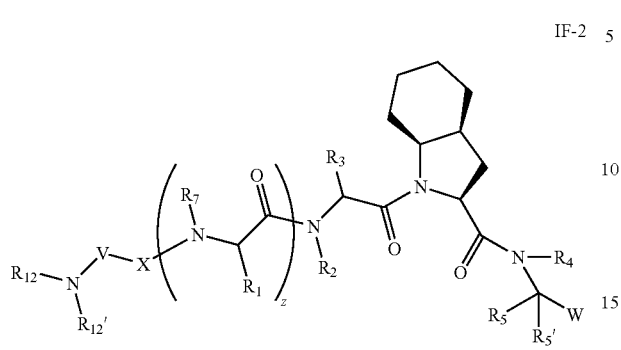

IF-2 wherein:
$R_1$, $R_2$, $R_3$, $R_4$, $R_5$, $R_{5'}$, $R_7$, z, X, V, and W, are as defined in any of the embodiments herein.

According to one embodiment of compounds of formula IF, formula IF-1, or formula IF-2, z is 1.

According to another embodiment of compounds of formula IF, formula IF-1, or formula IF-2, z is 0.

According to one embodiment for compounds of formula IF, formula IF-1, or formula IF-2, z is 1, W is selected from:

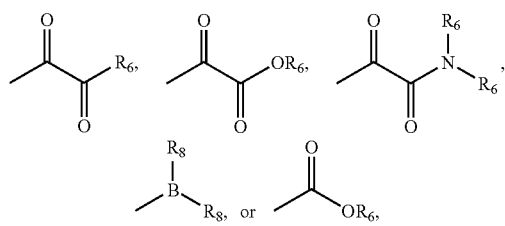

and $R_6$ and $R_8$ are as defined in any of the embodiments herein.

According to another embodiment for compounds of formula IF, formula IF-1, or formula IF-2, z is 0, W is selected from:

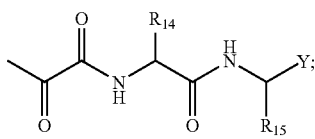

and $R_{14}$ and $R_{15}$ are as defined in any of the embodiments herein.

According to another embodiment for compounds of formula I or formula I-1, the

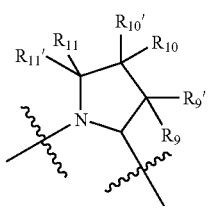

radical is:

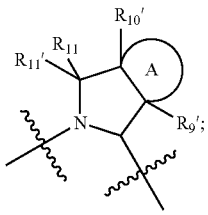

wherein;
ring A is a 5- to 6-membered aromatic or 3- to 6-membered non-aromatic ring having up to 3 heteroatoms independently selected from N, NH, O, SO, or $SO_2$;
wherein said ring A is optionally fused to a (C6-C10)aryl, (C5-C10)heteroaryl, (C3-C10)cycloalkyl, or (C3-C10) heterocyclyl;
wherein any ring has up to 3 substituents selected independently from J; and
$R_9$, $R_{10'}$, $R_{11}$, and $R_{11'}$ are as defined in any of the embodiments herein.

According to another embodiment for compounds of formula I or formula I-1, the

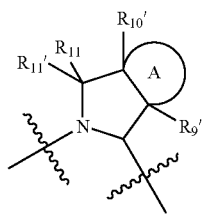

radical is:

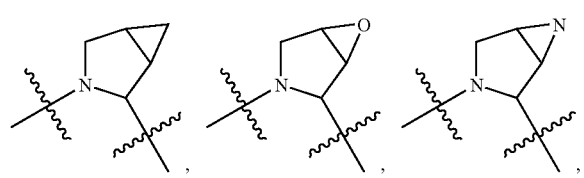

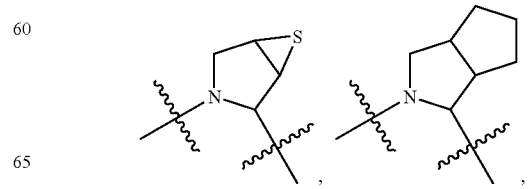

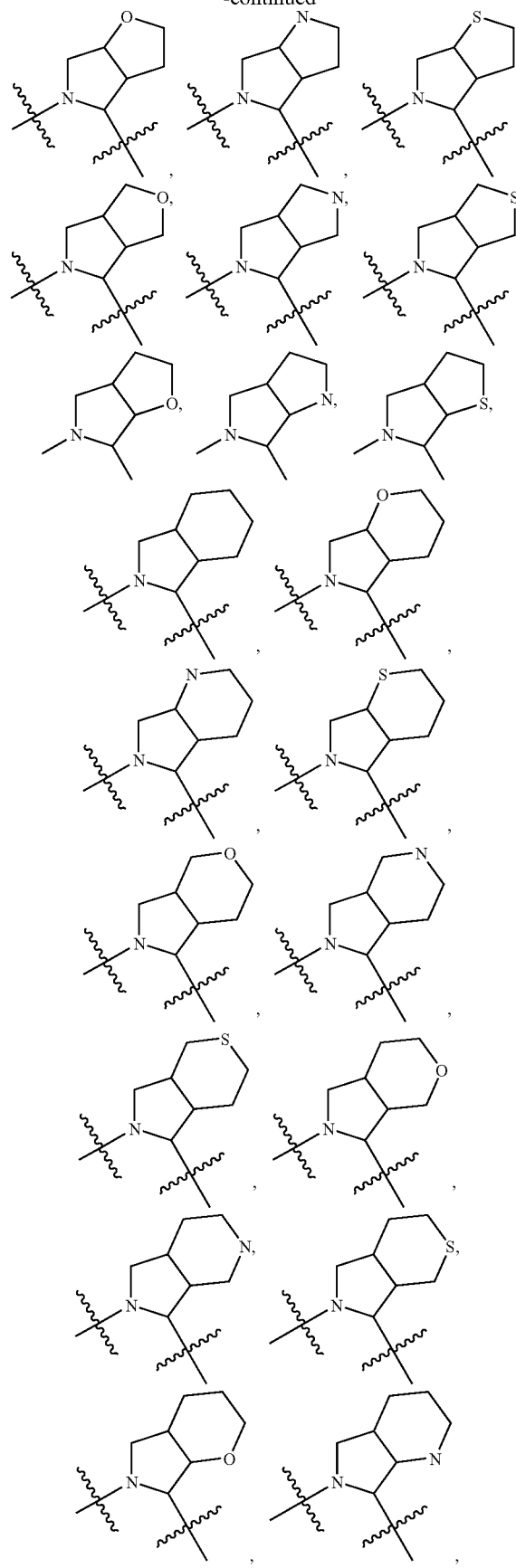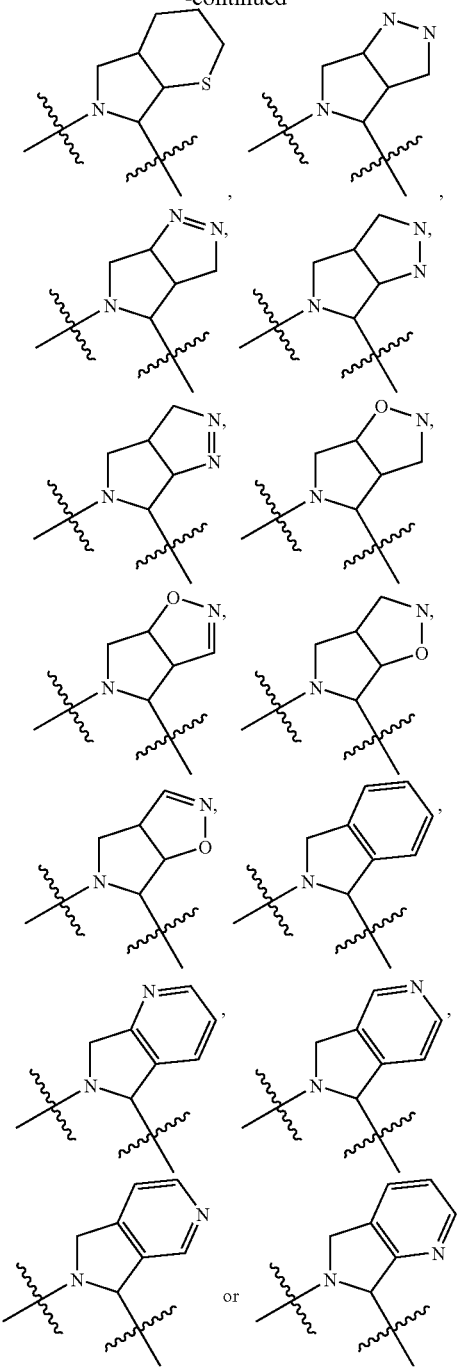
According to yet another embodiment for compounds of formula I or formula I-1, the
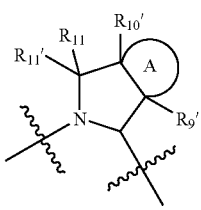

radical is:

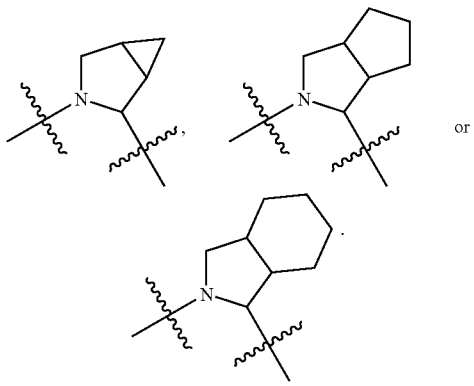

According to another embodiment, the present invention provides a compound of formula IG:

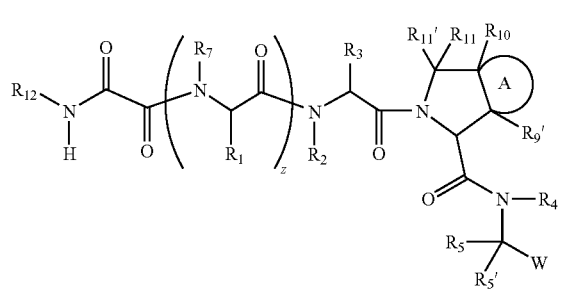

IG wherein:

$R_1$, $R_2$, $R_3$, $R_4$, $R_5$, $R_{5'}$, $R_7$, $R_{9'}$, $R_{10'}$, $R_{11'}$, $R_{12}$, z, W, and ring A are as defined in any of the embodiments herein.

According to another embodiment, the present invention provides a compound of formula IG-1:

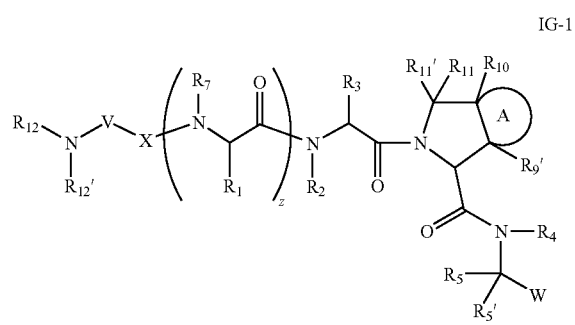

IG-1 wherein:

$R_1$, $R_2$, $R_3$, $R_4$, $R_5$, $R_{5'}$, $R_7$, $R_{9'}$, $R_{10'}$, $R_{11'}$, $R_{12}$, $R_{12'}$, z, W, X, V, and ring A are as defined in any of the embodiments herein.

According to one embodiment for compounds of formula IG or formula IG-1, z is 1.

According to another embodiment of compounds of formula IG or formula IG-1, z is 0.

According to yet another embodiment for compounds of formula IG or formula IG-1, z is one, W is selected from:

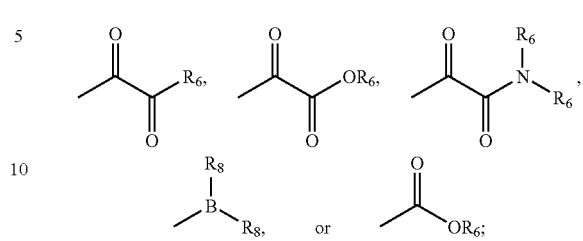

and $R_6$ and $R_8$ are as defined in any of the embodiments herein.

According to still another embodiment for compounds of formula IG or formula IG-1, z is 0, W is selected from:

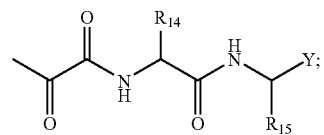

and $R_{14}$ and $R_{15}$ are as defined in any of the embodiments herein.

According to another embodiment for compounds of formula I or formula I-1, the

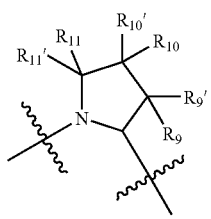

radical is:

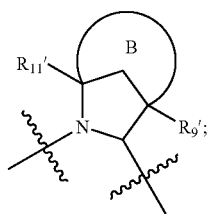

wherein:

ring B forms a 3- to a 20-membered carbocyclic or heterocyclic ring system;

wherein each ring B is either aromatic or nonaromatic;

wherein each heteroatom in the heterocyclic ring system is N, NH, O, SO, or $SO_2$;

wherein ring B is optionally fused to a (C6-C10)aryl, (C5-C10)heteroaryl, (C3-C10)cycloalkyl, or (C3-C10)heterocyclyl;

wherein each ring has up to 3 substituents selected independently from J; and $R_9$, and $R_{11'}$ are as defined in any of the embodiments herein.

According to another embodiment for compounds of formula I or formula I-1, the

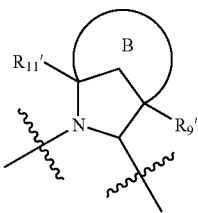

radical is:

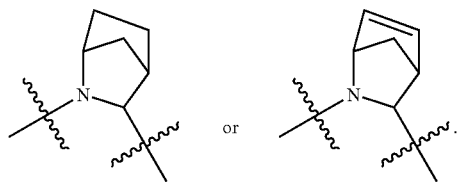 [SMILES: *C1C2CCC(C2)N1* ; "or" ; *C1C2C=CC(C2)N1* ; "."]

According to yet another embodiment, the present invention provides a compound of formula IH:

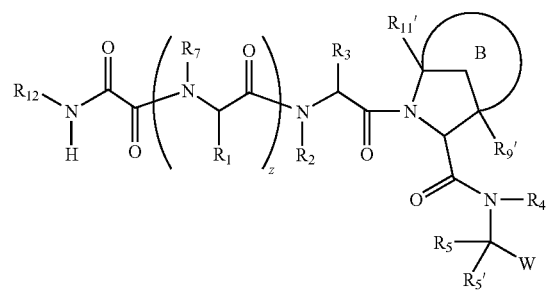

IH wherein:
R$_1$, R$_2$, R$_3$, R$_4$, R$_5$, R$_5'$, R$_7$, R$_9'$, R$_{11'}$, R$_{12}$, z, W, and ring B are as defined in any of the embodiments herein.

According to yet another embodiment, the present invention provides a compound of formula IH-1:

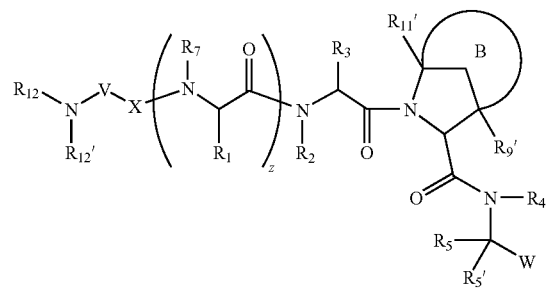

IH-1 wherein:
R$_1$, R$_2$, R$_3$, R$_4$, R$_5$, R$_5'$, R$_7$, R$_9'$, R$_{11'}$, R$_{12}$, R$_{12'}$, z, X, V, W, and ring B are as defined in any of the embodiments herein.

According to one embodiment for compounds of formula IH and formula IH-1, z is 1.

According to another embodiment for compounds of formula IH and formula IH-1, z is 0.

According to yet another embodiment for compounds of formula IH or formula IH-1, z is one, W is selected from:

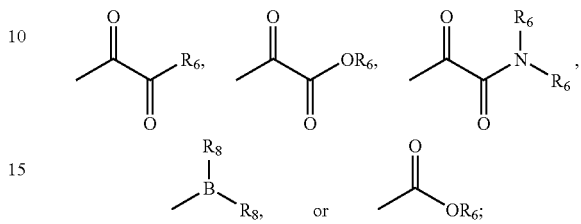

and R$_6$ and R$_8$ are as defined in any of the embodiments herein.

According to another embodiment for compounds of formula IH or formula IH-1, z is 0, W is selected from:

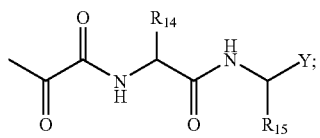

and R$_{14}$ and R$_{15}$ are as defined in any of the embodiments herein.

According to another embodiment, W in compounds of formula I or formula I-1 is:

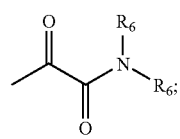

wherein in the W, the NR$_6$R$_6$ is selected from —NH—(C1-C6 aliphatic), —NH—(C3-C6 cycloalkyl), —NH—CH(CH$_3$)-aryl, or —NH—CH(CH$_3$)-heteroaryl, wherein said aryl or said heteroaryl is optionally substituted with up to 3 halogens.

According to another embodiment for compounds of formula I or formula I-1, the NR$_6$R$_6$ in the W radical is:

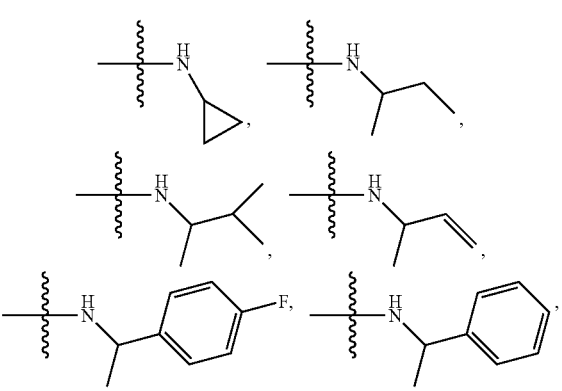

-continued

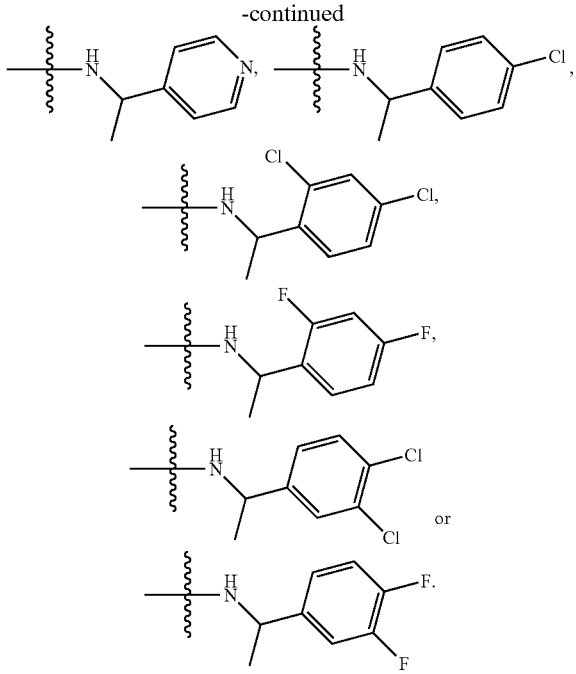

According to another embodiment for compounds of formula I or formula I-1, the $NR_6R_6$ in the W radical is:

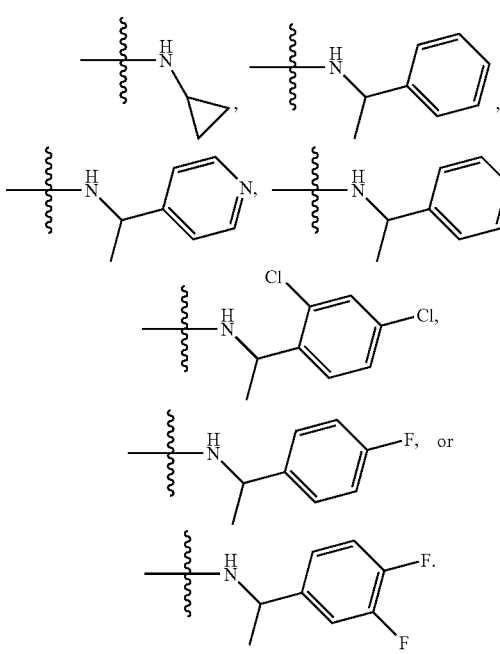

In another embodiment of compounds of formula I or formula I-1, in the W, the $NR_6R_6$ is:

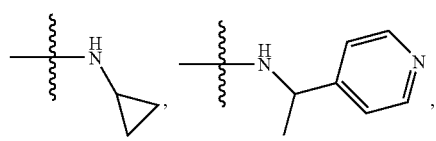

-continued

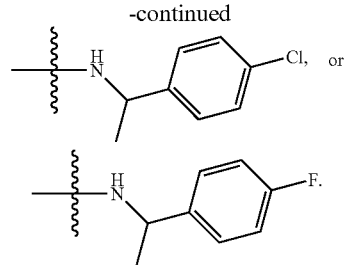

In yet another embodiment for compounds of formula I or formula I-1, in the W, the $NR_6R_6$ is:

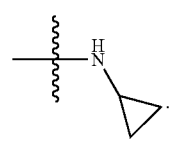

According to another embodiment for compounds of formula I or formula I-1, the $NR_6R_6$ in the W radical is:

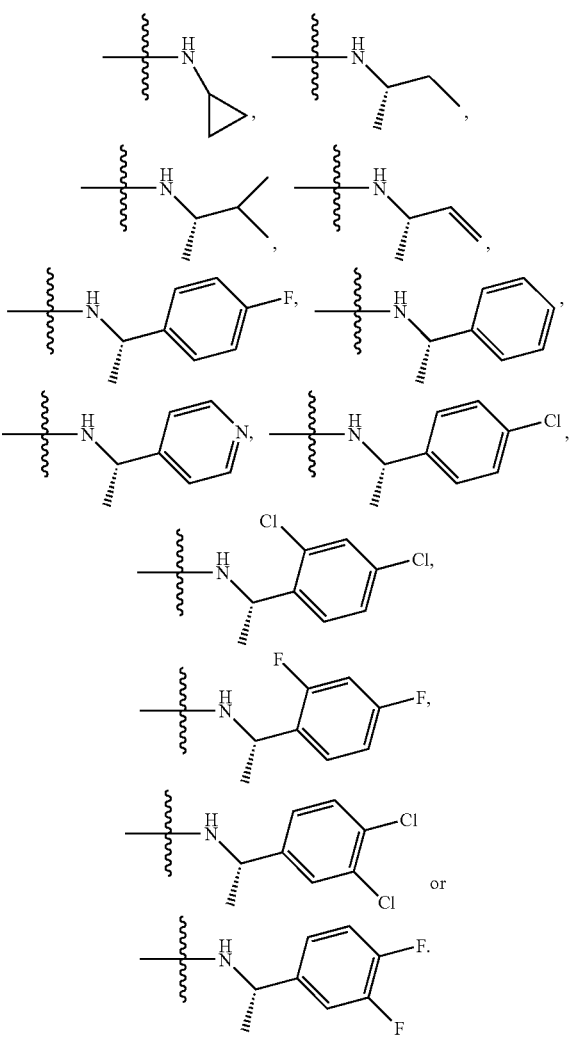

According to another embodiment in compounds of formula I or formula I-1, the $NR_6R_6$ in the W radical is:

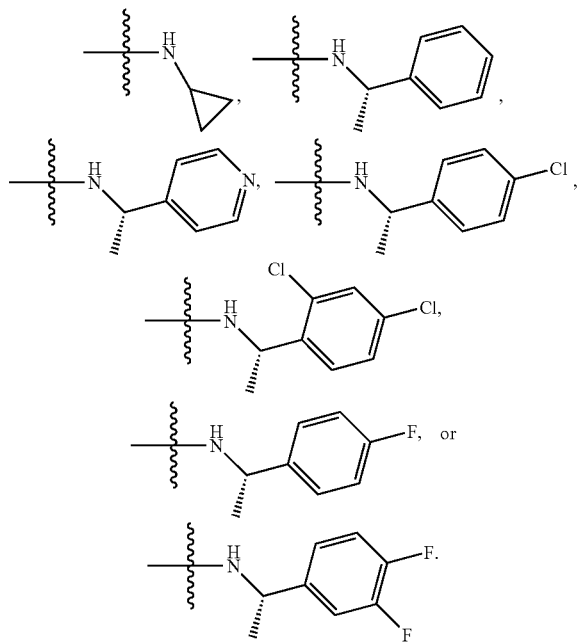

In yet another embodiment for compounds of formula I or formula I-1, in the W, the $NR_6R_6$ is:

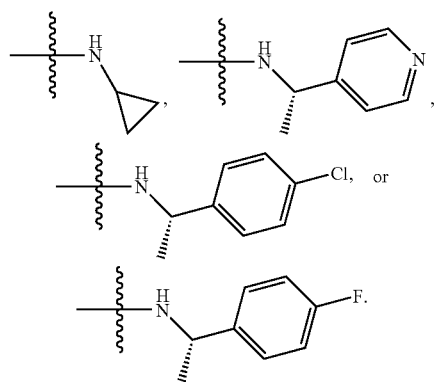

According to another embodiment, the present invention provides a compound of formula IJ:

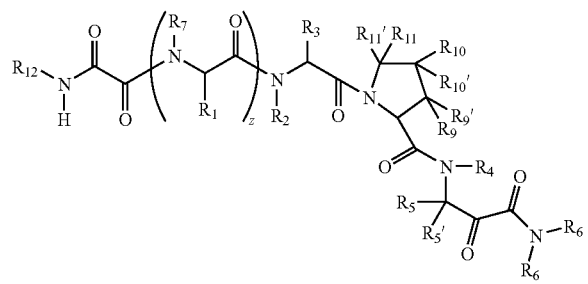

IJ wherein:

z, $R_1$, $R_2$, $R_3$, $R_4$, $R_5$, $R_{5'}$, $R_6$, $R_7$, $R_9$, $R_{9'}$, $R_{10}$, $R_{10'}$, $R_{11}$, $R_{11'}$, and $R_{12}$, are as defined in any of the embodiments herein.

According to another embodiment, the present invention provides a compound of formula IJ-1:

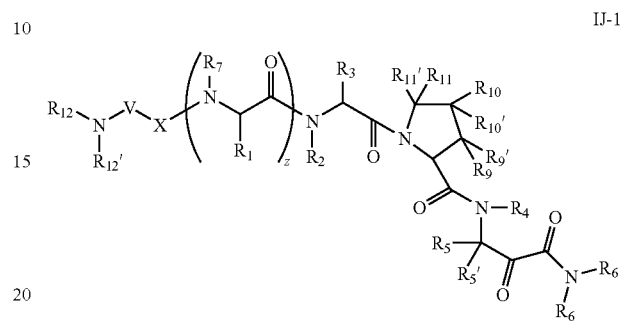

IJ-1 wherein:

$R_1$, $R_2$, $R_3$, $R_4$, $R_5$, $R_{5'}$, $R_6$, $R_7$, $R_9$, $R_{9'}$, $R_{10}$, $R_{10'}$, $R_{11}$, $R_{11'}$, $R_{12}$, z, X, and V are as defined in any of the embodiments herein.

According to one embodiment for compounds of formula IJ and formula IJ-1, z is 1.

According to another embodiment, W in compounds of formula I or formula I-1 is:

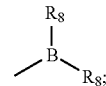

wherein $R_8$ is as defined above.

According to another embodiment for W in compounds of formula I or formula I-1, each $R_8$ together with the boron atom, is a (C5-C10)-membered heterocyclic ring having no additional heteroatoms other than the boron and the two oxygen atoms. In one embodiment, the heterocyclic ring is:

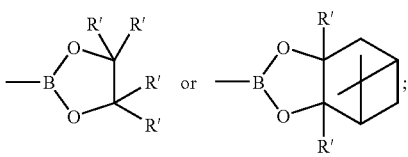

wherein R' is (C1-C6)-aliphatic. In another embodiment, R' is methyl.

According to another embodiment, when W in compounds of formula I or formula I-1 is:

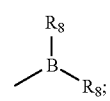

wherein $R_8$ is as defined above, then z is 1.

According to another embodiment, W in compounds of formula I or formula I-1 is:

[structure: CH3-C(=O)-C(=O)-R6]

wherein R$_6$ is as defined in any of the embodiments herein.

According to another embodiment, when W in compounds of formula I or formula I-1 is:

[structure: CH3-C(=O)-C(=O)-R6]

wherein R$_6$ is as defined in any of the embodiments herein, then z is 1.

According to yet another embodiment, W in compounds of formula I or formula I-1 is:

[structure: CH3-C(=O)-C(=O)-OR6]

wherein R$_6$ is as defined in any of the embodiments herein.

According to another embodiment, when W in compounds of formula I or formula I-1 is:

[structure: CH3-C(=O)-C(=O)-OR6]

wherein R$_6$ is as defined in any of the embodiments herein, then z is 1.

According to another embodiment, W in compounds of formula I or formula I-1 is:

[structure: CH3-C(=O)-OR6]

wherein R$_6$ is as defined in any of the embodiments herein.

According to another embodiment, when W in compounds of formula I or formula I-1 is:

[structure: CH3-C(=O)-OR6]

wherein R$_6$ is hydrogen, then z is 1.

According to another embodiment, the present invention provides a compound of formula Ij:

Ij

[structure of formula Ij]

wherein:
R$_1$, R$_2$, R$_3$, R$_4$, R$_5$, R$_5'$, R$_6$, R$_7$, R$_9$, R$_9'$, R$_{10}$, R$_{10'}$, R$_{11}$, R$_{11'}$, R$_{12'}$, R$_{12}$, and z are as defined in any of the embodiments herein.

According to one embodiment for compounds of formula Ij, z is 1.

According to another embodiment for compounds of formula Ij, R$_5$, and R$_5'$ are:

[seven structures shown]

According to another embodiment for compounds of formula Ij, R$_5$, and R$_5$, are:

[four structures shown]

According to another embodiment for compounds of formula I or formula I-1, R$_{5'}$ is hydrogen and R$_5$ is:

[eight structures shown with F, SH, CF3 substituents]

-continued

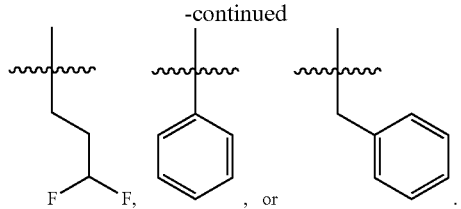

, or .

According to another embodiment for compounds of formula I or formula I-1, $R_{5'}$ is hydrogen and $R_5$ is:

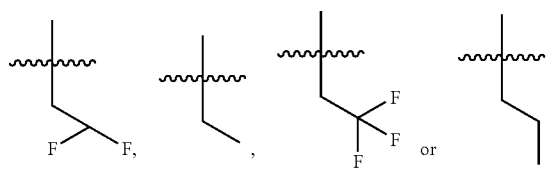

According to another embodiment, the present invention provides a compound of formula IK:

IK

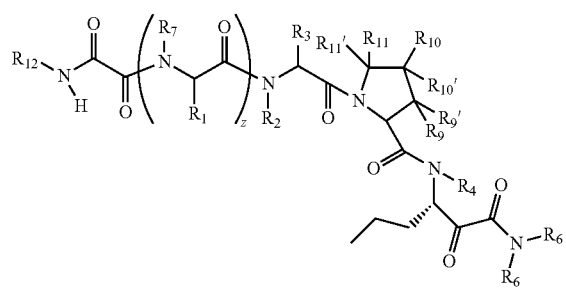

wherein:
z, $R_1$, $R_2$, $R_3$, $R_4$, $R_6$, $R_7$, $R_9$, $R_{9'}$, $R_{10}$, $R_{10'}$, $R_{11}$, $R_{11'}$, and $R_{12}$, are as defined in any of the embodiments herein.

According to another embodiment, the present invention provides a compound of formula IK-1:

IK-1

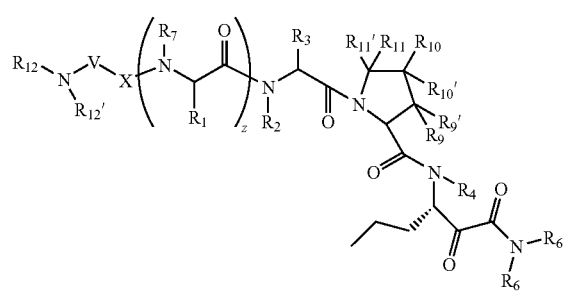

wherein:
$R_1$, $R_2$, $R_3$, $R_4$, $R_6$, $R_7$, $R_9$, $R_{9'}$, $R_{10}$, $R_{10'}$, $R_{11}$, $R_{11'}$, $R_{12'}$, $R_{12}$, z, X, and V are as defined in any of the embodiments herein.

According to another embodiment for compounds of formula IK or formula IK-1, $R_1$, $R_2$, $R_3$, $R_4$, $R_6$, $R_7$, $R_9$, $R_{9'}$, $R_{10}$, $R_{10'}$, $R_{11}$, $R_{11'}$, $R_{12'}$, $R_{12}$, X, and V are as defined in any of the embodiments herein, z is 1, and $NR_6R_6$ is:

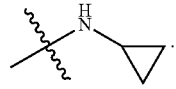

According to another embodiment for compounds of formula IK or formula IK-1, $R_1$, $R_2$, $R_3$, $R_4$, $R_6$, $R_7$, $R_9$, $R_{9'}$, $R_{10}$, $R_{10'}$, $R_{11}$, $R_{11'}$, $R_{12'}$, $R_{12}$, X, and V are as defined in any of the embodiments herein and z is 1.

According to another embodiment, the present invention provides a compound of formula IK-2:

IK-2

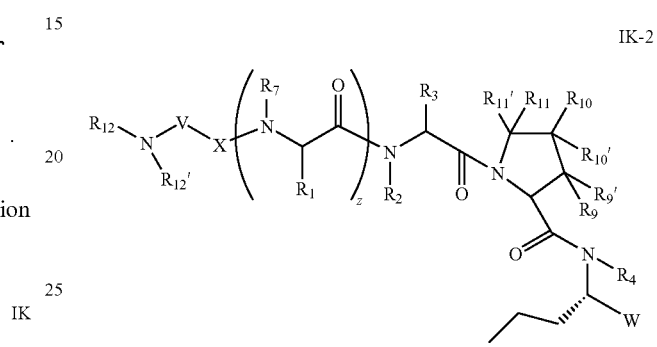

wherein:
$R_1$, $R_2$, $R_3$, $R_4$, $R_7$, $R_9$, $R_{9'}$, $R_{10}$, $R_{10'}$, $R_{11}$, $R_{11'}$, $R_{12'}$, $R_{12}$, z, X, V, and W are as defined in any of the embodiments herein.

According to another embodiment for compounds of formula IK-2, z is 1, W is selected from:

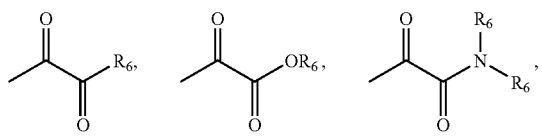

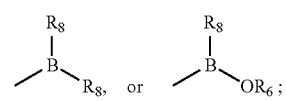

and $R_6$ and $R_8$ are as defined in any of the embodiments herein.

According to another embodiment for compounds of formula IK-2, z is 0, W is selected from:

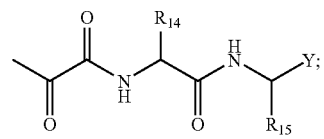

and $R_{14}$ and $R_{15}$ are as defined in any of the embodiments herein.

According to another embodiment for compounds of formula I or formula I-1, $R_{5'}$ and $R_5$ are:

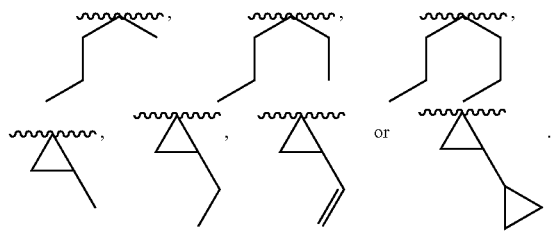

According to another embodiment for compounds of formula I or formula I-1, $R_7$ if present, and $R_2$, $R_4$, and $R_{12'}$ are each independently H, methyl, ethyl, or propyl.

According to another embodiment for compounds of formula I or formula I-1, $R_7$ if present, and $R_2$ and $R_4$ are each H.

According to another embodiment, the present invention provides a compound of formula IL:

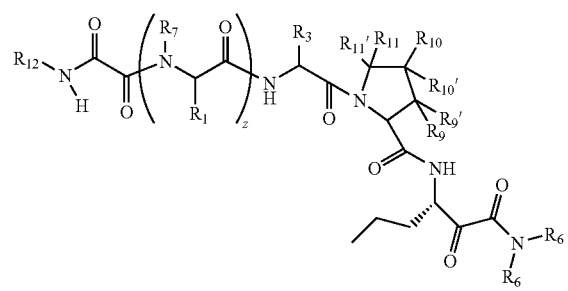

wherein:

z, $R_1$, $R_3$, $R_6$, $R_9$, $R_{9'}$, $R_{10}$, $R_{10'}$, $R_{11}$, $R_{11'}$, and $R_{12}$ are as defined in any of the embodiments herein.

According to another embodiment, the present invention provides a compound of formula IL-1:

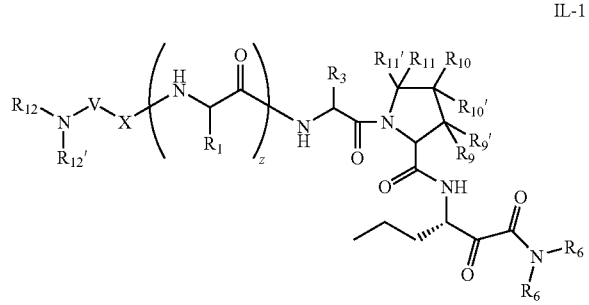

wherein:

$R_1$, $R_3$, $R_6$, $R_9$, $R_{9'}$, $R_{10}$, $R_{10'}$, $R_{11}$, $R_{11'}$, $R_{12'}$, $R_{12}$, z, X, and V are as defined in any of the embodiments herein.

According to one embodiment for compounds of formula IL or formula IL-1, $R_1$, $R_3$, $R_6$, $R_9$, $R_{9'}$, $R_{10}$, $R_{10'}$, $R_{11}$, $R_{11'}$, $R_{12'}$, $R_{12}$, z, X, and V are as defined in any of the embodiments herein, and $NR_6R_6$ is:

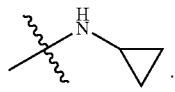

According to another embodiment for compounds of formula IL or formula IL-1, z is one, $R_1$, $R_3$, $R_6$, $R_9$, $R_{9'}$, $R_{10}$, $R_{10'}$, $R_{11}$, $R_{11'}$, $R_{12'}$, $R_{12}$, X, and V are as defined in any of the embodiments herein, and $NR_6R_6$ is:

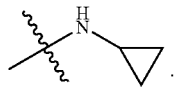

According to another embodiment, the present invention provides a compound of formula IL-2:

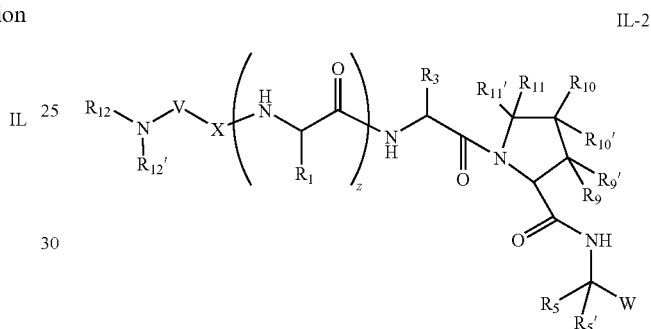

wherein:

$R_1$, $R_3$, $R_5$, $R_{5'}$, $R_6$, $R_9$, $R_{9'}$, $R_{10}$, $R_{10'}$, $R_{11}$, $R_{11'}$, $R_{12'}$, $R_{12}$, z, X, V, and W are as defined in any of the embodiments herein.

According to another embodiment for compounds of formula IL-2, z is one, W is selected from:

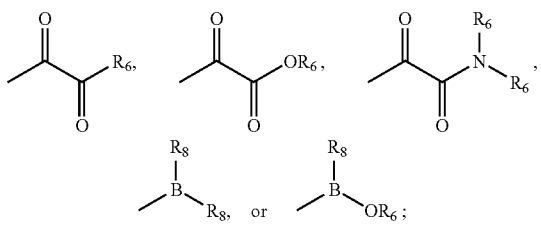

and $R_6$ and $R_8$ are as defined in any of the embodiments herein.

According to another embodiment for compounds of formula IL-2, z is 0, W is selected from:

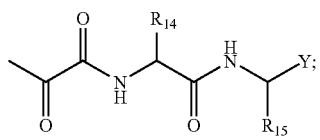

and $R_{14}$ and $R_{15}$ are as defined in any of the embodiments herein.

According to another embodiment for compounds of formula I or formula I-1, $R_3$ is:

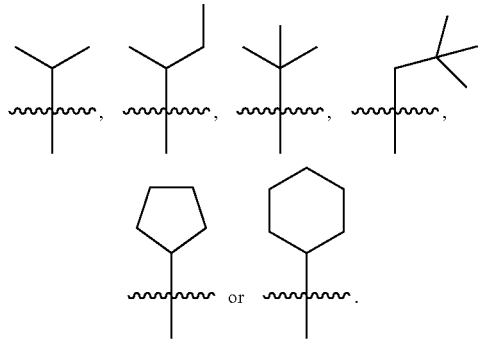

According to another embodiment for compounds of formula I or formula I-1, $R_3$ is:

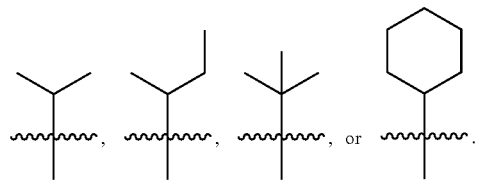

According to yet another embodiment for compounds of formula I or formula I-1, $R_3$ is:

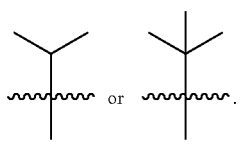

According to another embodiment, the present invention provides a compound of formula IM:

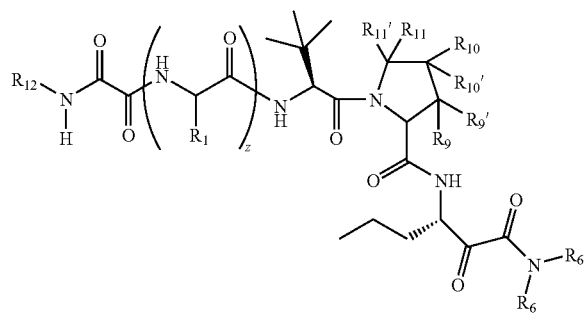

IM wherein:
z is 1, and $R_1$, $R_6$, $R_9$, $R_{9'}$, $R_{10}$, $R_{10'}$, $R_{11}$, $R_{11'}$, and $R_{12}$ are as defined in any of the embodiments herein.

According to another embodiment, the present invention provides a compound of formula IM-1:

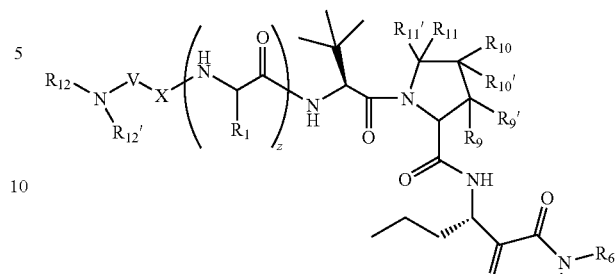

IM-1 wherein:
z is 1, and $R_1$, $R_6$, $R_9$, $R_{9'}$, $R_{10}$, $R_{10'}$, $R_{11}$, $R_{11'}$, $R_{12}$, $R_{12'}$, X, and V are as defined in any of the embodiments herein.

According to another embodiment, the present invention provides a compound of formula IM-2:

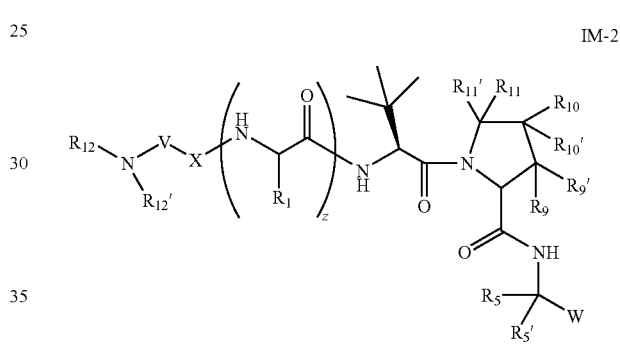

IM-2 wherein:
$R_1$, $R_5$, $R_{5'}$, $R_6$, $R_9$, $R_{9'}$, $R_{10}$, $R_{10'}$, $R_{11}$, $R_{11'}$, $R_{12}$, $R_{12'}$, z, X, V, and W are as defined in any of the embodiments herein.

According to another embodiment, the present invention provides a compound of formula IM-3:

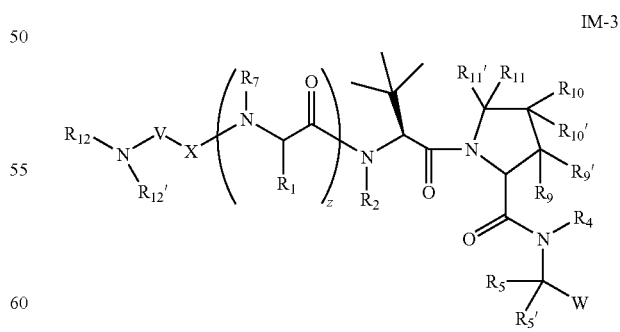

IM-3 wherein:
$R_1$, $R_2$, $R_4$, $R_5$, $R_{5'}$, $R_6$, $R_7$, $R_9$, $R_{9'}$, $R_{10}$, $R_{10'}$, $R_{11}$, $R_{11'}$, $R_{12}$, $R_{12'}$, z, X, V, and W are as defined in any of the embodiments herein.

According to another embodiment for compounds of formula IM-2 or formula IM-3, z is one, W is selected from:

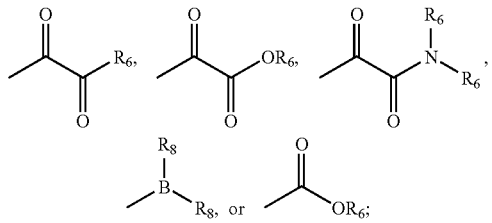

and $R_6$ and $R_8$ are as defined in any of the embodiments herein.

According to another embodiment for compounds of formula IM-2 or formula IM-3, z is 0, W is selected from:

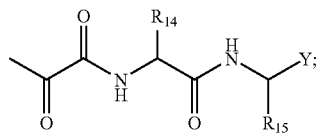

and $R_{14}$ and $R_{15}$ are as defined in any of the embodiments herein.

According to another embodiment for compounds of formula I or formula I-1, $R_1$ is:

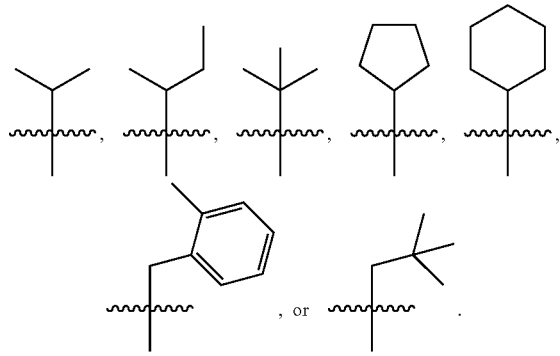

According to another embodiment for compounds of formula I or formula I-1, $R_1$ is:

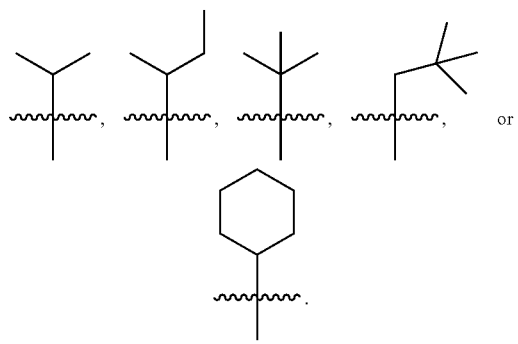

In yet another embodiment for compounds of formula I or formula I-1, $R_1$ is cyclohexyl.

According to another embodiment, the present invention provides a compound of formula IN:

IN

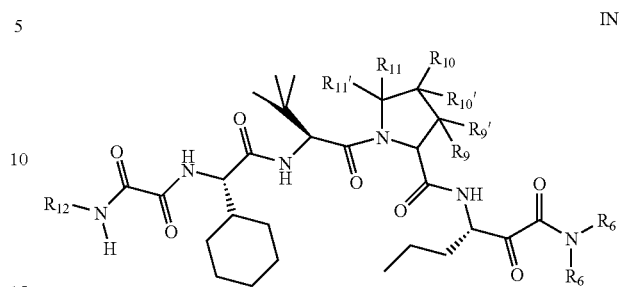

wherein:
$R_6, R_9, R_{9'}, R_{10}, R_{10'}, R_{11}, R_{11'}$ and $R_{12}$ are as defined in any of the embodiments herein.

According to another embodiment, the present invention provides a compound of formula IN-1:

IN-1

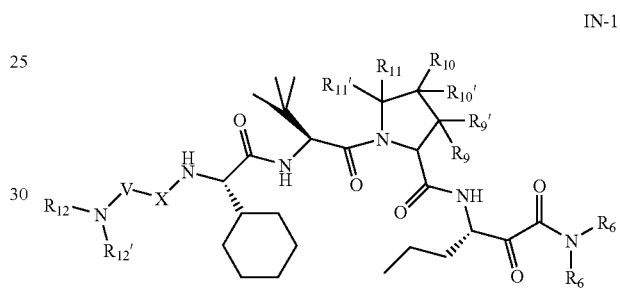

wherein:
$R_6, R_9, R_{9'}, R_{10}, R_{10'}, R_{11}, R_{11'}, R_{12'}, R_{12}, X$ and V are as defined in any of the embodiments herein.

According to another embodiment for compounds of formula IN, and formula IN-1, $R_6, R_9, R_{9'}, R_{10}, R_{10'}, R_{11}, R_{11'}, R_{12'}, R_{12}, X$ and V are as defined in any of the embodiments herein, and $NR_6R_6$ is:

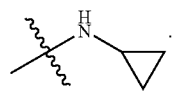

According to another embodiment, the present invention provides a compound of formula IN-2:

IN-2

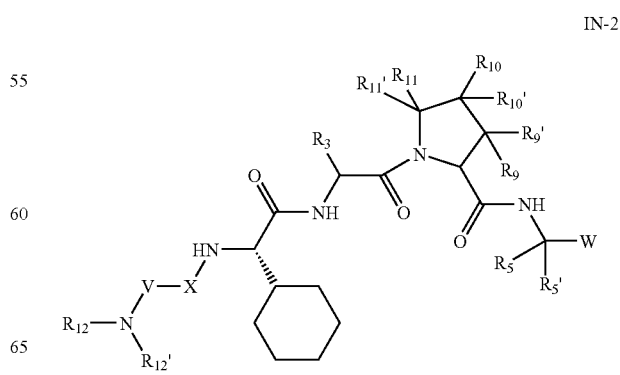

wherein:
$R_3$, $R_5$, $R_{5'}$, $R_6$, $R_9$, $R_{9'}$, $R_{10}$, $R_{10'}$, $R_{11}$, $R_{11'}$, $R_{12'}$, $R_{12}$, X V, and W are as defined in any of the embodiments herein.

According to another embodiment, the present invention provides a compound of formula IN-3:

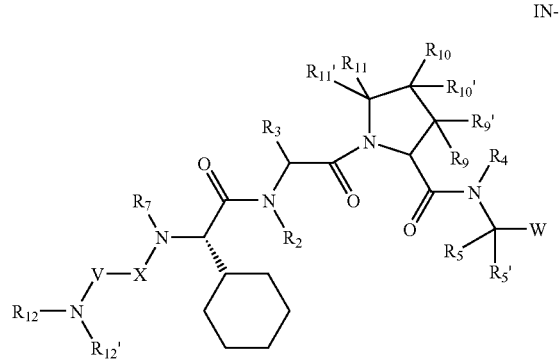

wherein:
$R_2$, $R_3$, $R_4$, $R_5$, $R_{5'}$, $R_6$, $R_7$, $R_9$, $R_{9'}$, $R_{10}$, $R_{10'}$, $R_{11}$, $R_{11'}$, $R_{12'}$, $R_{12}$, X, V, and W are as defined in any of the embodiments herein.

According to another embodiment for compounds of formula IN-2 or formula IN-3, z is one, W is selected from:

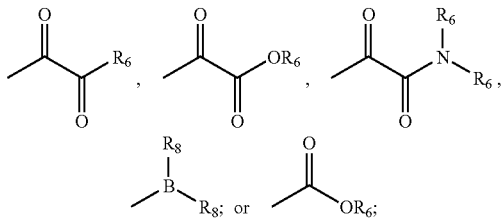

and $R_6$ and $R_8$ are as defined in any of the embodiments herein.

According to another embodiment for compounds of formula IN-2 or formula IN-3, z is 0, W is selected from:

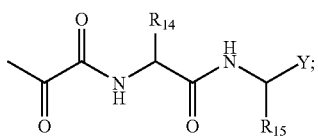

and $R_{14}$ and $R_{15}$ are as defined in any of the embodiments herein.

According to another embodiment for compounds of formula I or formula I-1, optional J substituents on any substitutable nitrogen are selected from —R', —N(R')$_2$, —N(R')SO$_2$R', —SO$_2$R', —SO$_2$N(R')$_2$, —C(O)R', —C(O)OR', —C(O)C(O)R', —C(O)C(O)N(R')$_2$, —C(O)CH$_2$C(O)R', —C(=NH)N(R')$_2$, or —C(O)N(R')$_2$.

According to another embodiment for compounds of formula I or I-1, no carbon atoms of $R_1$, $R_3$, $R_5$, and $R_{5'}$ are replaced with N, NH, O, or S. In other embodiments of compounds of formula I or I-1, these $R_1$, $R_3$, $R_5$, and $R_{5'}$ groups have no J substituents.

According to another embodiment for compounds of formula I, the compound is:

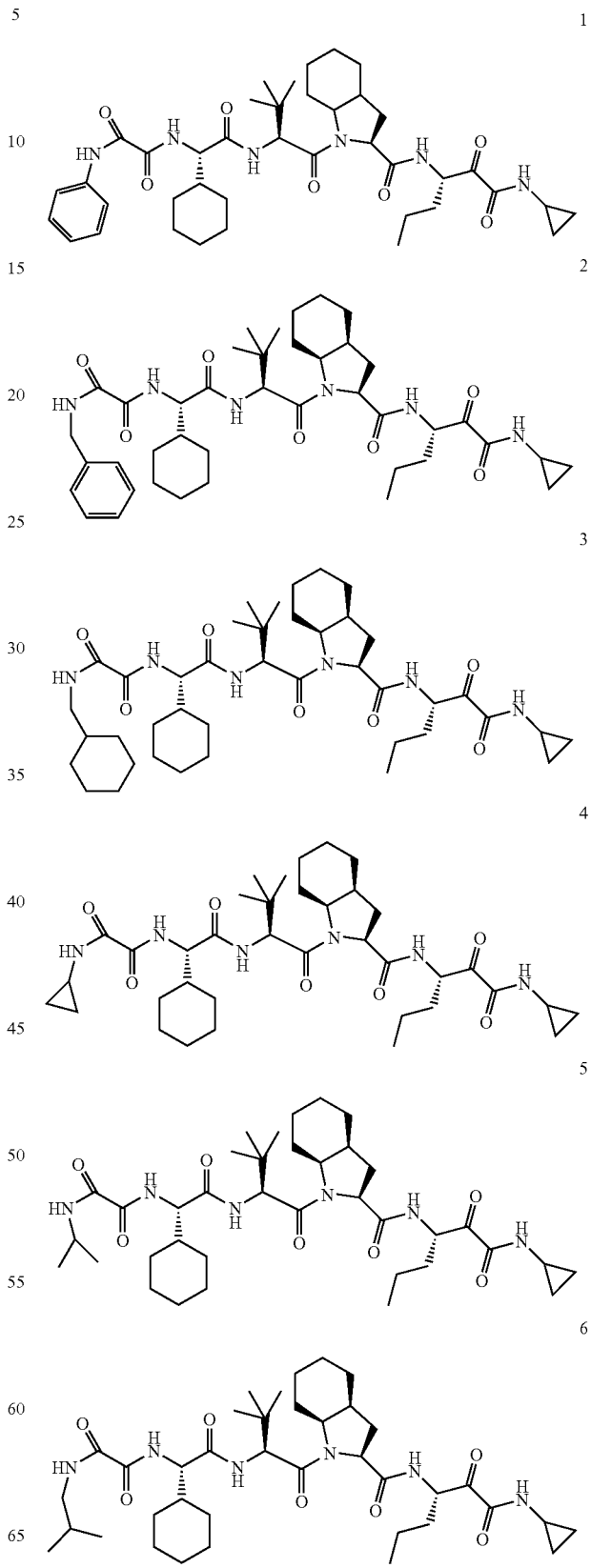

7

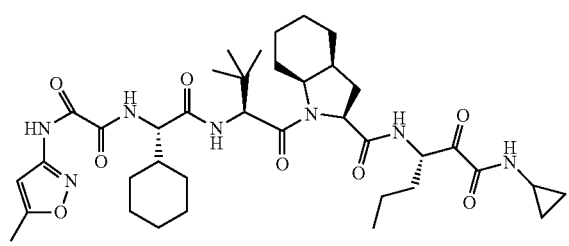

8

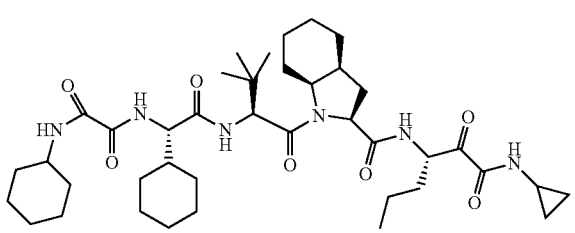

9

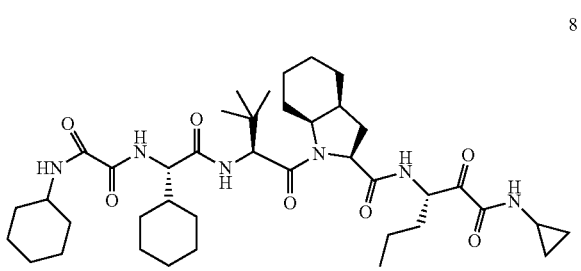

10

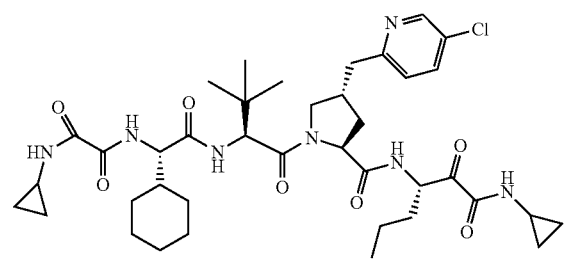

11

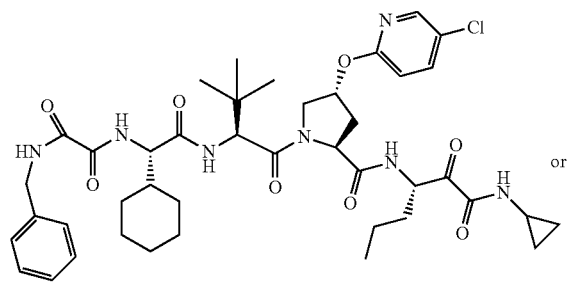

or

12

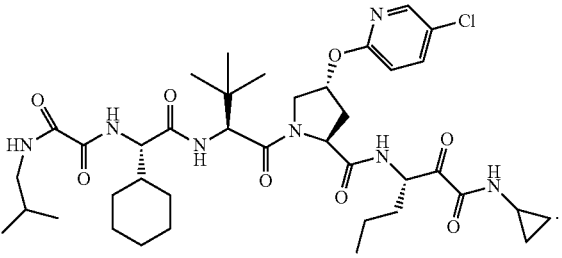

The compounds of this invention may contain one or more asymmetric carbon atoms and thus may occur as racemates and racemic mixtures, single enantiomers, diastereomeric mixtures and individual diastereomers. All such isomeric forms of these compounds are expressly included in the present invention. Each stereogenic carbon may be of the R or S configuration.

In one embodiment, the compounds of this invention have the structure and stereochemistry depicted in compounds 1-12.

Any of the embodiments recited herein, including those embodiments in the above species, may define formula I or formula I-1 individually or be combined to produce an embodiment of this invention.

Abbreviations which are used in the schemes, preparations and the examples that follow are:
THF: tetrahydrofuran
DMF: N,N,-dimethylformamide
EtOAc: ethyl acetate
AcOH: acetic acid
NMM: N-methylmorpholine
NMP: N-methylpyyrolidinone
EtOH: ethanol
t-BuOH: tert-butanol
Et$_2$O: diethyl ether
DMSO: dimethyl sulfoxide
DCCA: dichloroacetic acid
DIEA: diisopropylethylamine
MeCN: acetonitrile
TFA: trifluoroacetic acid
DBU: 1,8-diazabicyclo[5.4.0]undec-7-ene
DEAD: diethyl azodicarboxylate
HOBt: 1-hydroxybenzotriazole hydrate
HOAt: 1-hydroxy-7-azabenzotriazole
EDC: 1-(3-dimethylaminopropyl)-3-ethylcarbodiimide hydrochloride
Boc: tert-butyloxycarbonyl
Boc$_2$O: di-tert-butyldicarbonate
Cbz: benzyloxycarbonyl
Cbz-Cl: benzyl chloroformate
Fmoc: 9-fluorenyl methyloxycarbonyl
Chg: cyclohexylglycine
t-BG: tert-butylglycine
mCBPA: 3-chloroperoxybenzoic acid
DAST: (diethylamino)sulfur trifluoride
TEMPO: 2,2,6,6-tetramethyl-1-piperidinyloxy, free radical
PyBOP: tris(pyrrolidino)bromophosphonium hexafluorophosphate
TBTU or HATU: 2-(1H-benzotriazole-1-yl)-1,1,3,3-tetramethyluronium tetrafluoroborate
DMAP: 4-dimethylaminopyridine
AIBN: 2,2'-azobisisobutyronitrile
DMEM: Dulbecco's minimal essential media PBS: phosphate-buffered saline
rt or RT: room temperature
ON: overnight
ND: not determined
MS: mass spectrometry
LC: liquid chromatography
General Synthetic Methodology:

The compounds of this invention may be prepared in general by methods known to those skilled in the art. Schemes 1-16 below illustrate synthetic routes to the compounds of the present invention. Other equivalent schemes, which will be readily apparent to the ordinary skilled organic chemist, may alternatively be used to synthesize various portions of the molecule as illustrated by the general schemes below, and the preparative examples that follow.

Scheme 1:

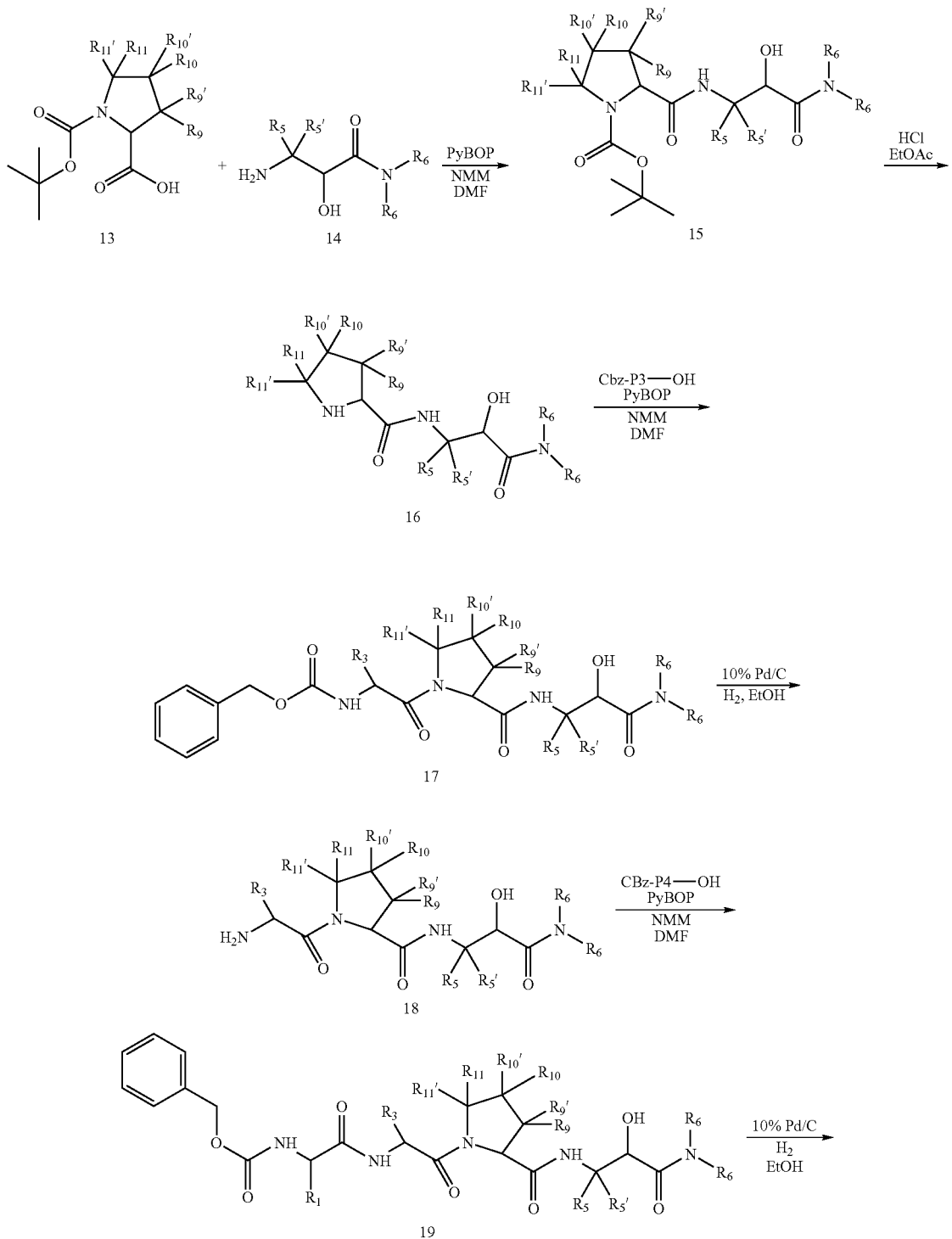

-continued

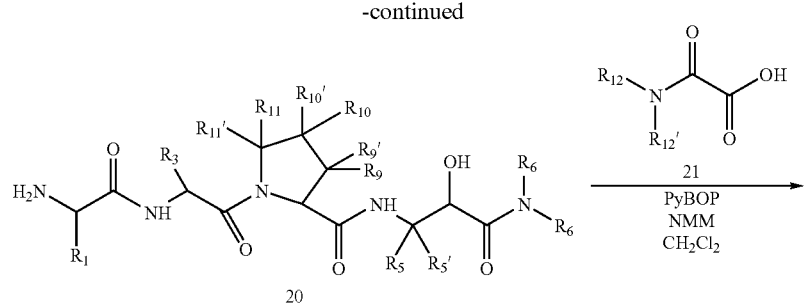

20

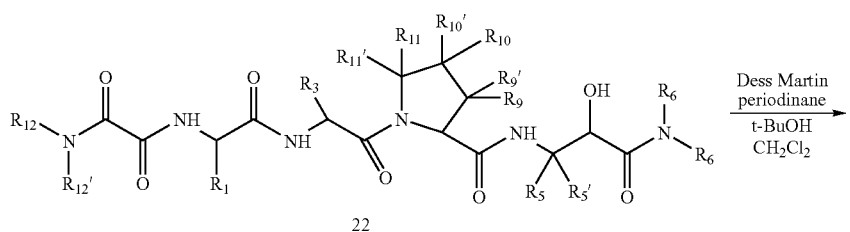

22

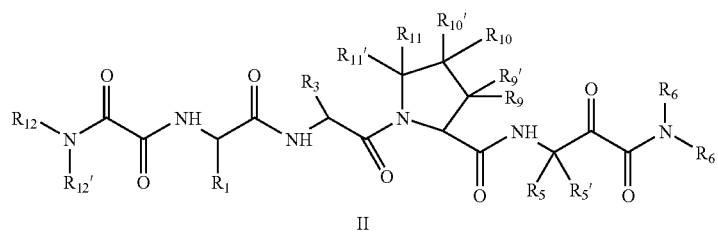

II

Scheme 1 above provides a general route for the preparation of compounds of formula I, II, IA, IB, IC, ID, IE, IF, IG, IH, IJ, IK, IL, IM, and IN wherein X-V is —C(O)C(O), w is —C(O)C(O)—N($R_6$)$_2$, $R^2$, $R^4$, and $R^7$ are H, and $R^1$, $R^3$, $R^5$, $R^{5'}$, $R^9$, $R^{9'}$, $R^{10}$, $R^{10'}$, $R^{11}$, $R^{11'}$, $R^{12}$, and $R^{12'}$ are as described in any of the embodiments herein. As would be recognized by skilled practitioners, other suitable and commercially available coupling reagents may be used to prepare intermediates 15, 17, 19, and 22. Additionally, it will be recognized that the commercially available Cbz protected amino acids represented by, for instance, Cbz-P3-OH, may alternatively be substituted with the commercial t-Boc protected amino acids. Suitable deprotection conditions to remove the Boc protecting groups are known to those skilled in the art. Likewise the oxidation of intermediate 22 to compounds of formula II may be accomplished using other suitable conditions known to the skilled artisan.

Scheme 2:

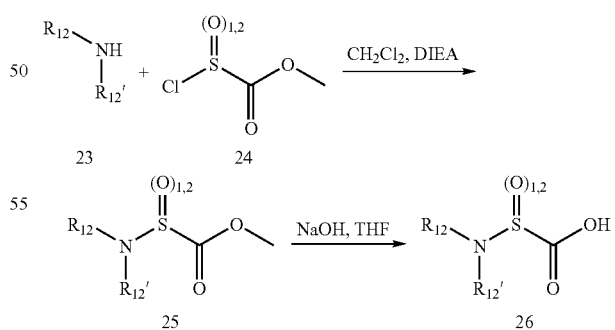

Scheme 2 above provides a general route for the preparation of compounds of formula 26. Therein, commercially available amine 23 and sulfonyl chloride 24 are condensed and then hydrolyzed under basic conditions to provide intermediate acid 26. Alternatively, the skilled practitioner will recognize that other suitable reagents may be used to prepare intermediate 26.

Scheme 3:

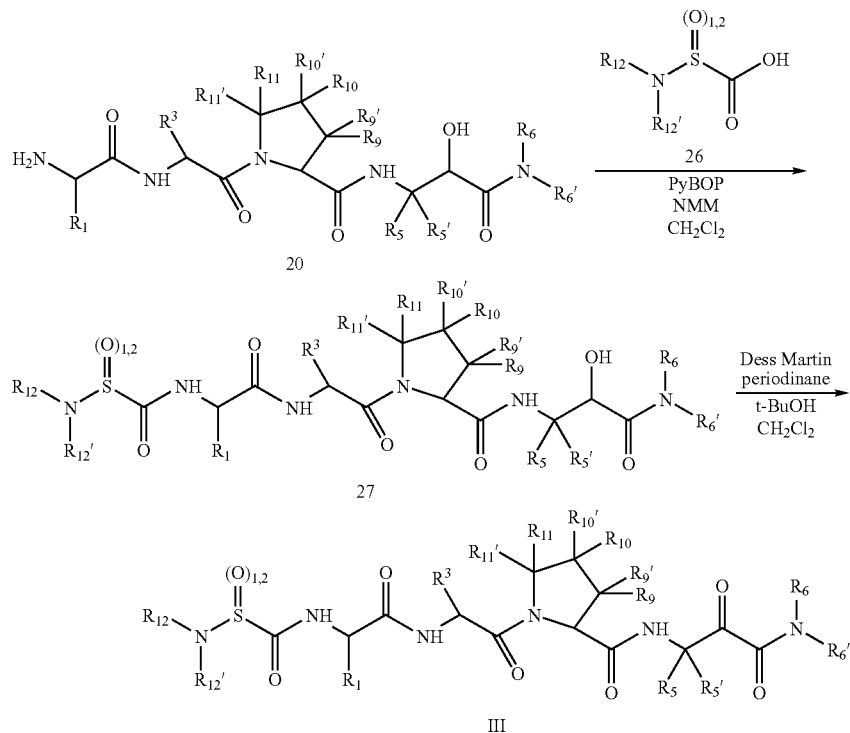

Scheme 3 above provides a general route for the preparation of compounds of formula III and formula I. Therein, coupling of the acid 26 and amine 20 to give amide intermediate 27 may be accomplished using the conditions indicated or coupling reagents known to one of skill in the art. Subsequent oxidation of keto alcohol 27 with Dess Martin periodinane, or other oxidation conditions known to those skilled in the art, affords compounds of formula III or formula I, wherein X-V is $-C(O)S(O)_{1-2}$, W is $-C(O)C(O)-N(R_6)_2$, $R^2$, $R^4$, and $R^7$ are H, and $R^1$, $R^3$, $R^5$, $R^{5'}$, $R^9$, $R^{9'}$, $R^{10}$, $R^{10'}$, $R^{11}$, $R^{11'}$, $R^{12}$, and $R^{12'}$ are as described in any of the embodiments herein.

Scheme 4:

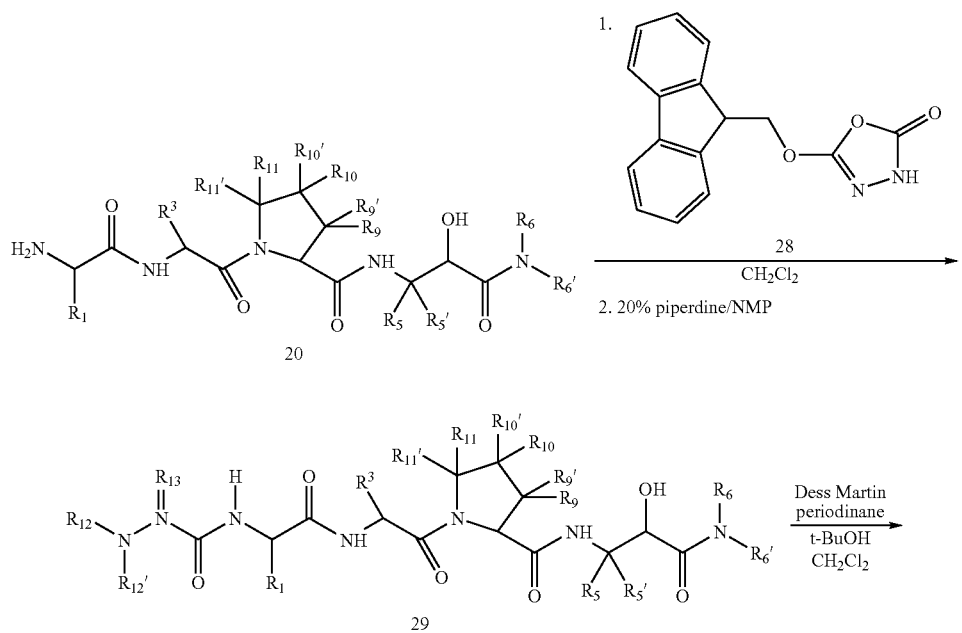

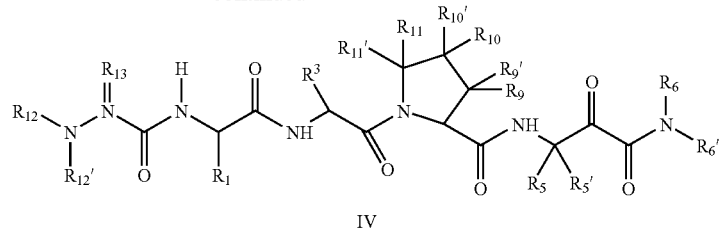

IV

Scheme 4 above provides a general route for the preparation of compounds of formula VI and formula I. Therein, compound 28 is prepared according to the methods described in Kessler et al., J. Med. Chem., pp. 1918-1930 (2003). Addition of the Fmoc-oxadiazolone in an appropriate solvent gives semi-carbazide 29. Deprotection of the Fmoc group with piperidine in N-methylpyrrolidinone followed by oxidation with Dess Martin periodinane gives compounds of formula IV. It will be appreciated by those skilled in the art that other known conditions can be used to accomplish the oxidation of compounds 29 to compounds of formula I and IV.

Scheme 5:

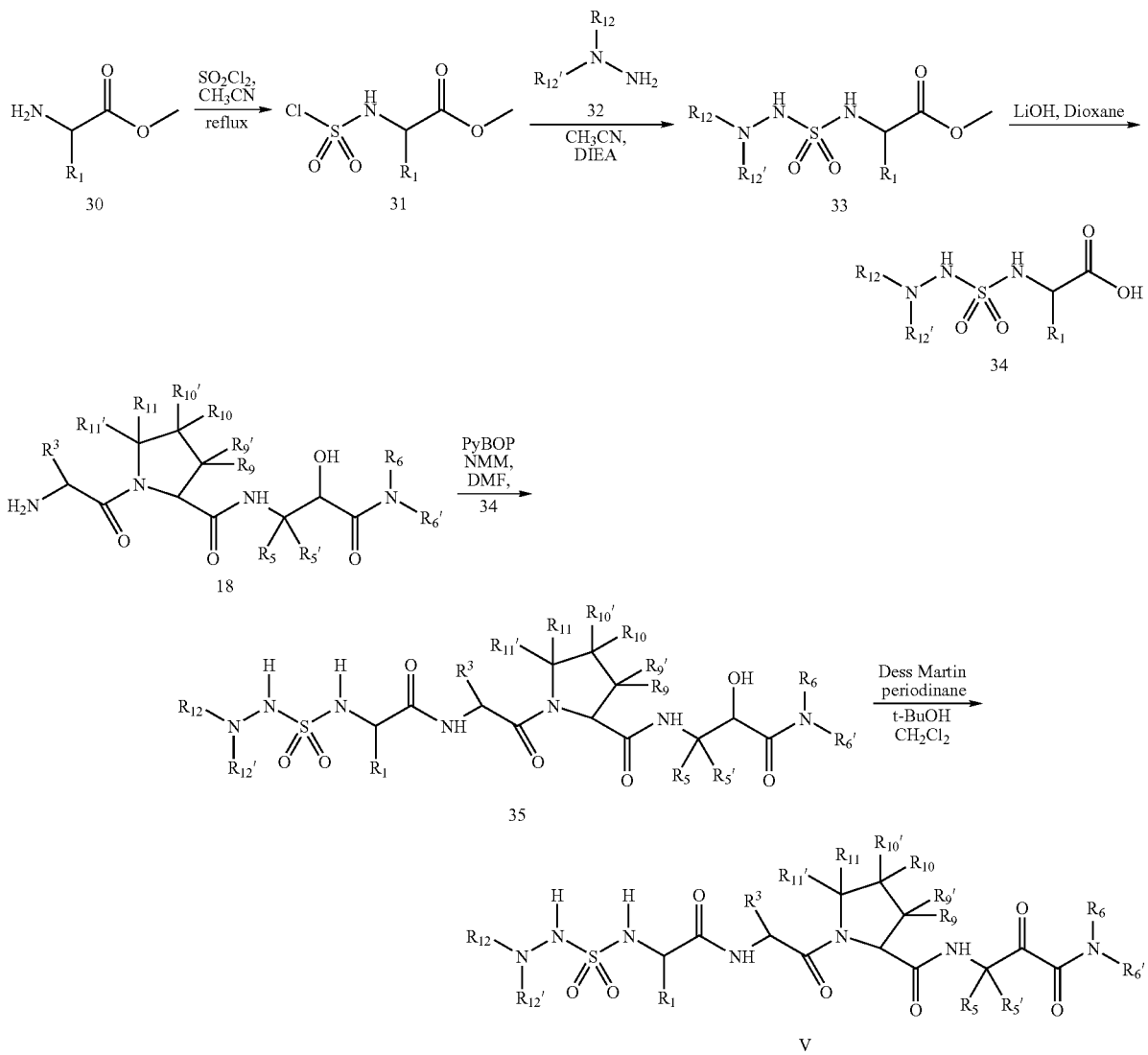

Scheme 5 above provides a general route for the preparation of compounds of formula V and formula I.

Therein, commercially available amino acid ester 30 is converted to the corresponding N-chlorosulfonyl ester 31 according to the procedure described by Kempf, D. J. et al., J.

Med. Chem., pp. 320-330 (1993). Coupling of 31 with commercially available hydrazine 32 followed by hydrolysis yields acid 34. Coupling of the acid 34 and amine 18 to give amide intermediate 35 may be accomplished using the conditions indicated or coupling reagents known to one of skill in the art. Subsequent oxidation of 35 with Dess Martin periodinane, or other suitable conditions known to those skilled in the art, affords compounds of formula V and formula I.

described in J. Org. Chem., pp. 2624-2629 (1979). Coupling of commercially available amino t-butyl ester 36 with chloride 37 gives sulfonamide 38. Basic hydrolysis of mixed ester 38 followed by coupling with commercially available amine 39 affords intermediate ester 40. Oxidation with one equivalent of mCBPA affords sulfoxide 41, wherein X is —S(O)$_1$—. Alternatively, oxidation with two equivalents of mCBPA affords sulfone 41, wherein X is —S(O)$_2$—. Acidic hydroly- Scheme 6:

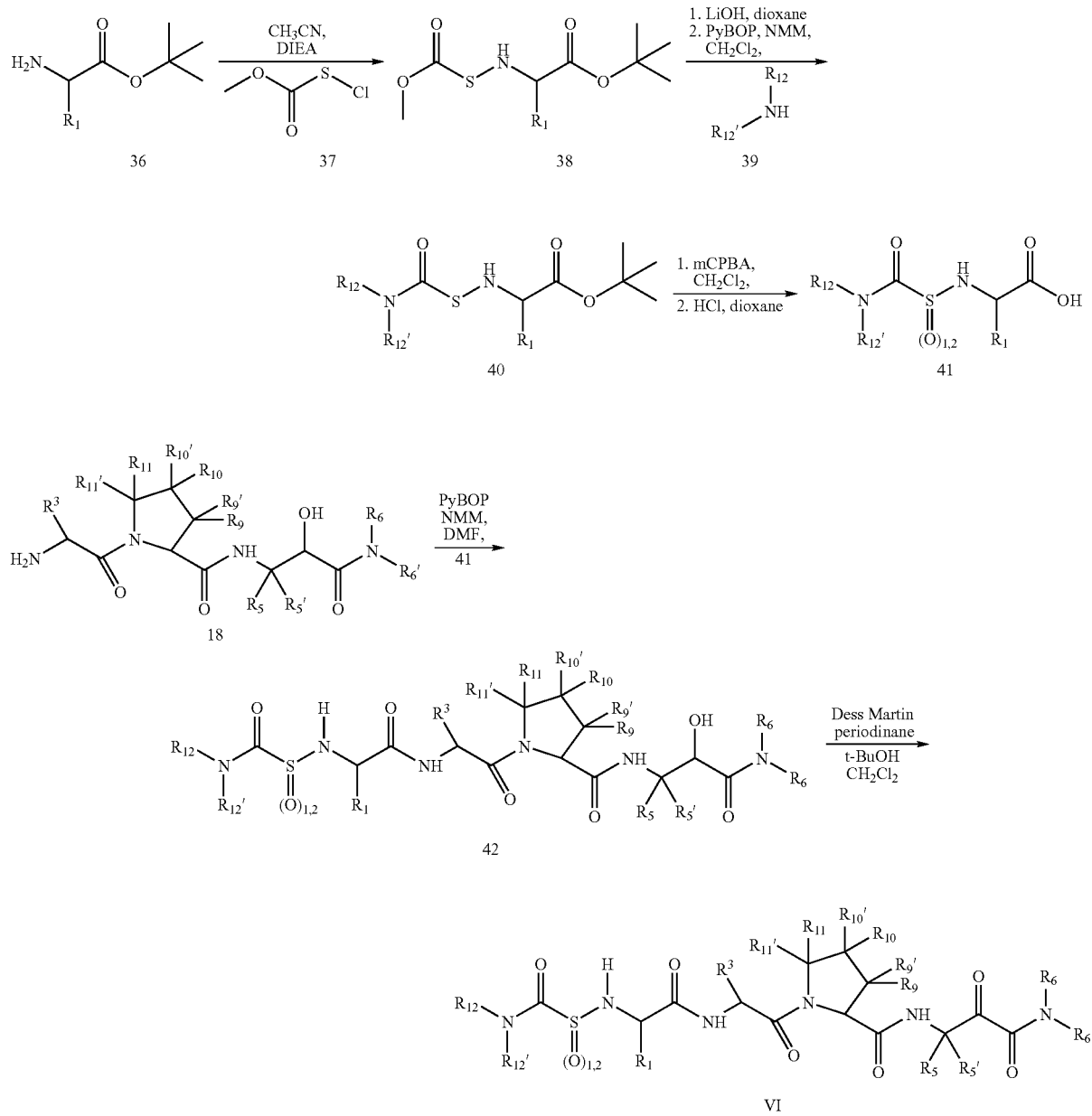

Scheme 6 above provides a general route for the preparation of compounds of formula I and formula VI, wherein X-V is —S(O)$_{1-2}$C(O)—, W is —C(O)C(O)—N(R$_6$)$_2$, R$^2$, R$^4$ and R$^7$ are H, and R$^1$, R$^3$, R$^5$, R$^{5'}$, R$^9$, R$^{9'}$, R$^{10}$, R$^{10'}$, R$^{11}$, R$^{11'}$, R$^{12}$, and R$^{12'}$ are as described in any of the embodiments herein. Chloroester 37 is prepared according to the methods sis of t-butyl ester 40 yields acid 41, which is coupled to amine 18 (described previously in Scheme 1) to give keto alcohol 42. Finally, oxidation of 42 with Dess Martin periodinane or other suitable conditions know in the art gives compounds of formula VI.

Scheme 7:
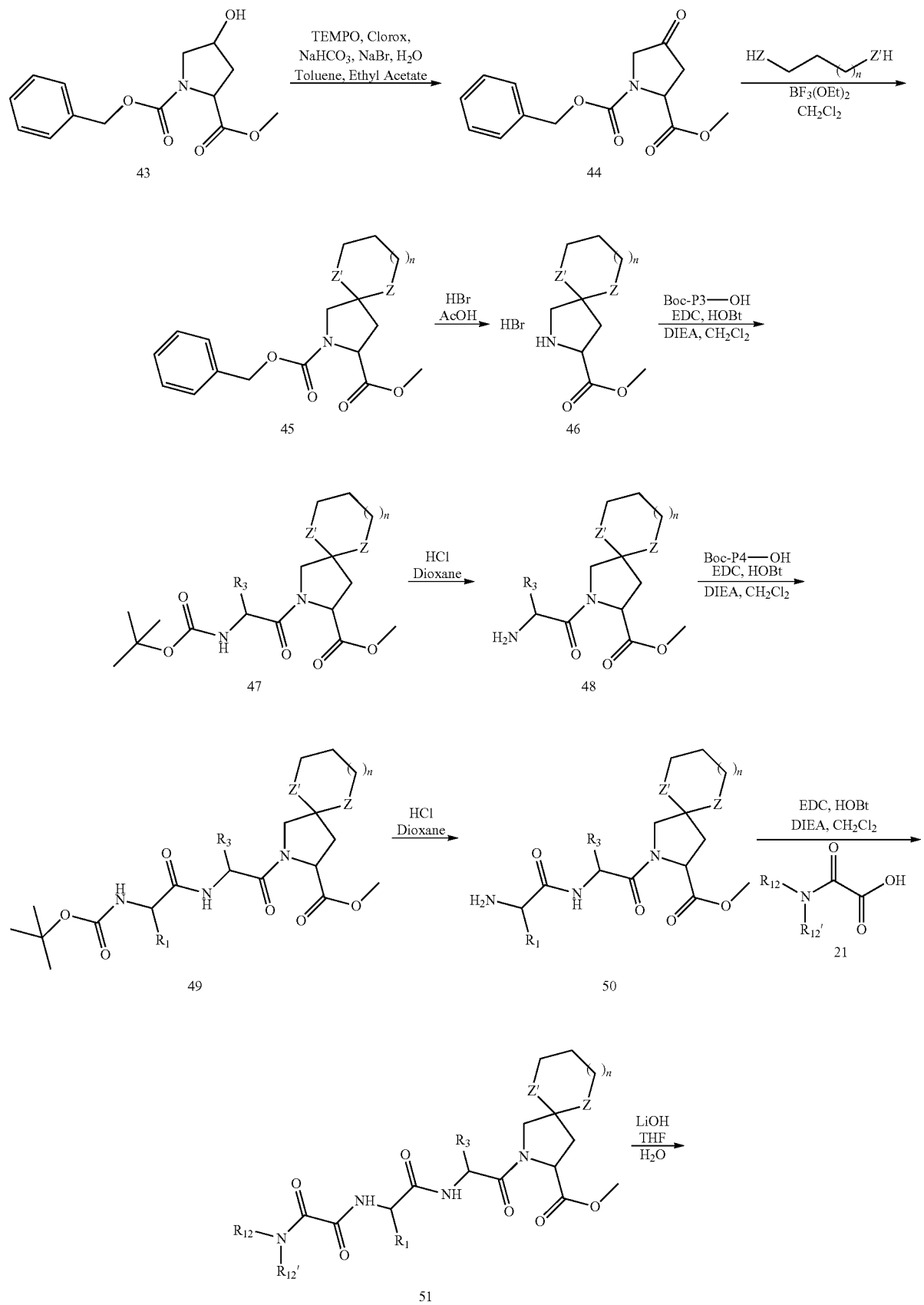

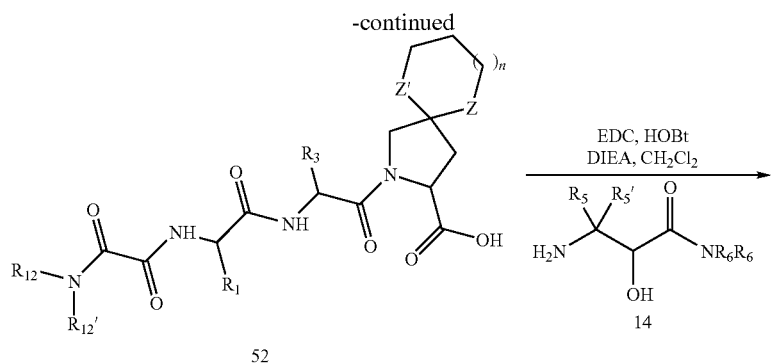

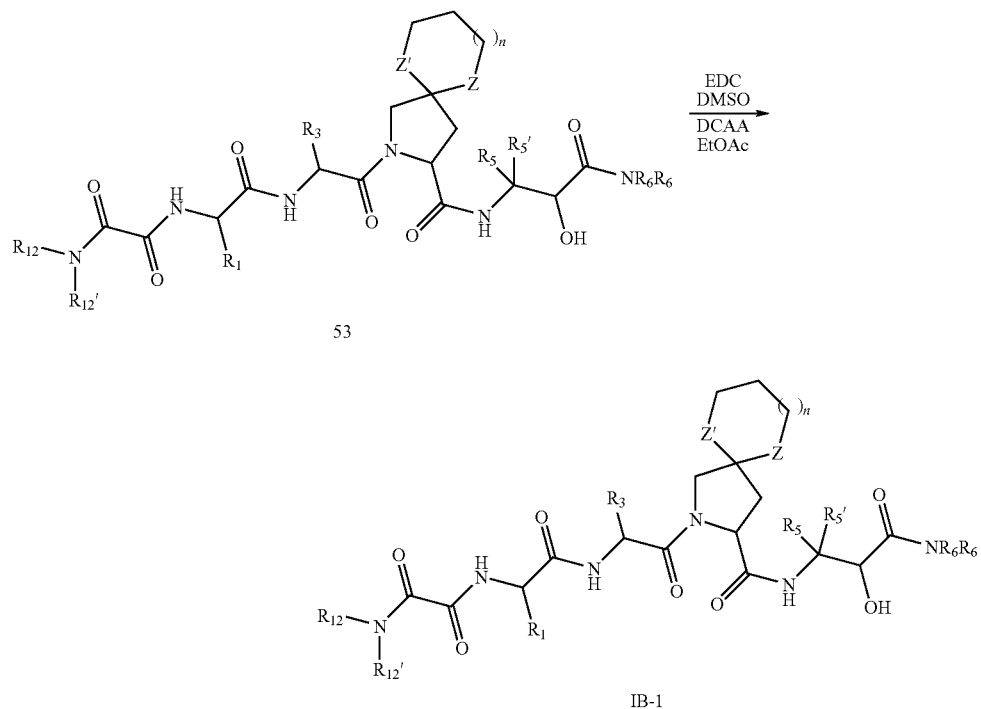

Scheme 7 above provides a general route for the preparation of compounds of formula IB-1, formula IB, and formula IC, wherein X-V is —C(O)C(O)—, W is —C(O)C(O)—N(R$_6$)$_2$, R$^2$, R$^4$, and R$^7$ are H, and n, Z, Z', R$^1$, R$^3$, R$^5$, R$^{5'}$, R$^9$, R$^{9'}$, R$^{10}$, R$^{10'}$, R$^{11}$, R$^{11'}$, R$^{12}$, and R$_{12'}$ are as described in any of the embodiments herein. As would be recognized by skilled practitioners, other suitable and commercially available coupling reagents may be used to prepare intermediates 47, 49, 51, and 53. Additionally, it will be recognized that the commercially available Boc protected amino acids represented by, for instance, Boc-P3-OH, may alternatively be substituted with the commercial CBz protected amino acids. Suitable deprotection conditions to remove the Cbz protecting groups are known to those skilled in the art. Likewise the oxidation of intermediate 53 to compounds of formula IB-1 may be accomplished using other suitable conditions known to the skilled artisan.

Scheme 8:

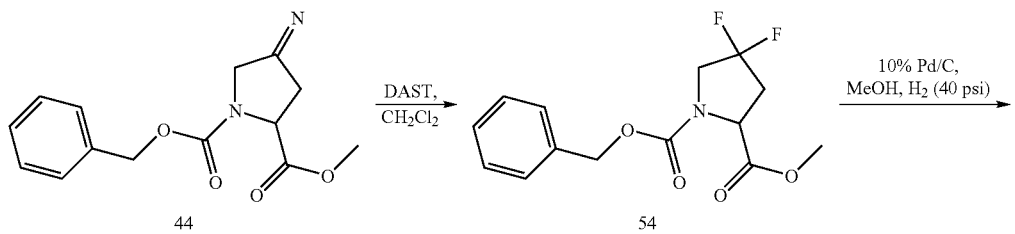

-continued
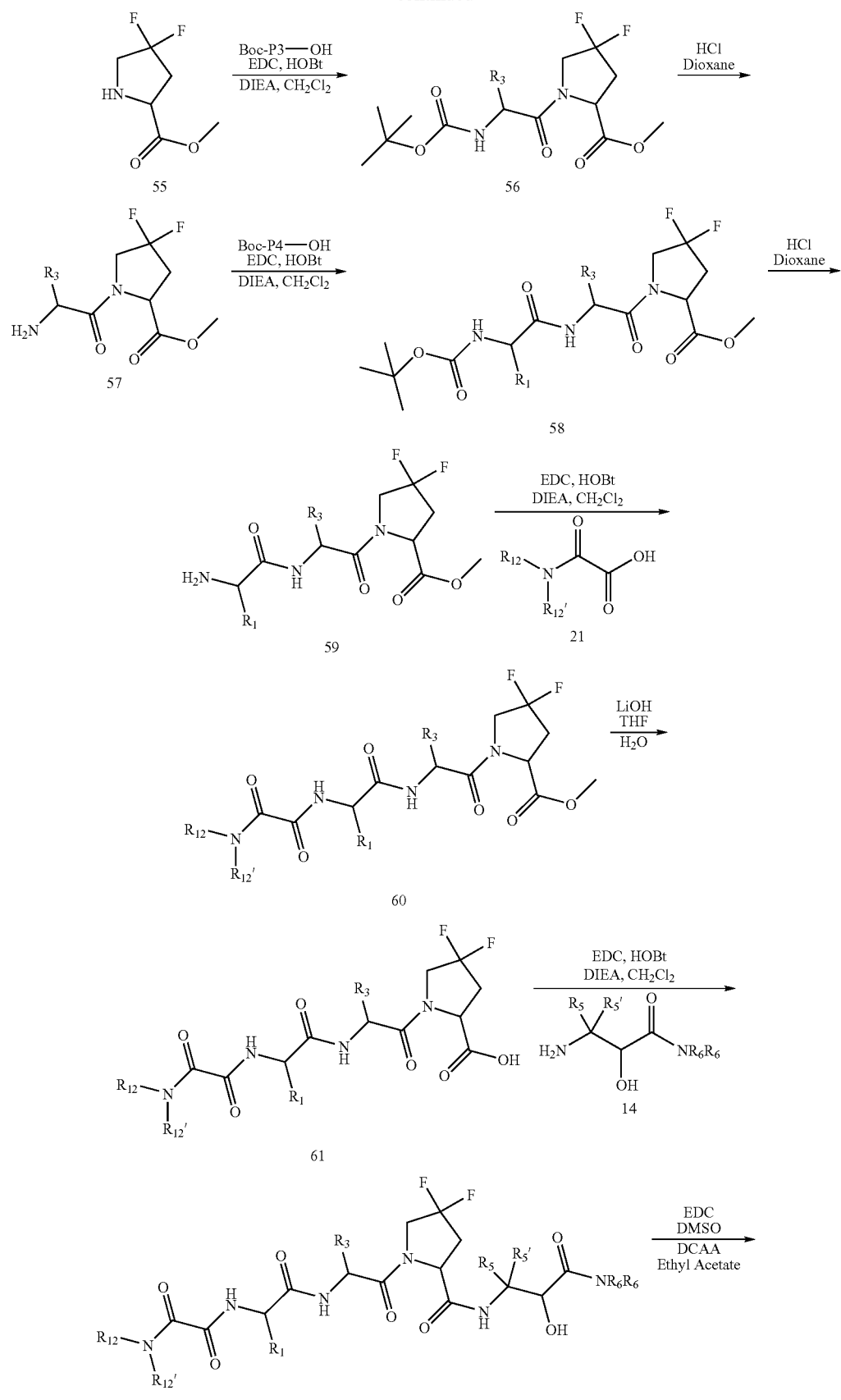

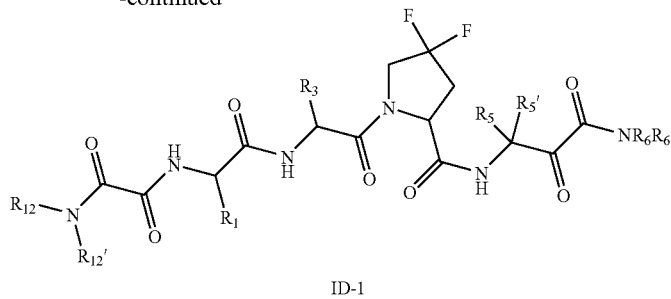

ID-1

Scheme 8 above provides a general route for the preparation of compounds of formula ID-1 and formula ID, wherein X-V is —C(O)C(O)—, W is —C(O)C(O)—N($R_6$)$_2$, $R^2$, $R^4$, and $R^7$ are H, and $R^1$, $R^3$, $R^5$, $R^{5'}$, $R^6$, $R^{12}$, and $R^{12'}$ are as described in any of the embodiments herein. As would be recognized by any skilled practitioner, other suitable and commercially available coupling reagents may be used to prepare intermediates 56, 58, 60, and 62. Additionally, it will be recognized that the commercially available Boc protected amino acids represented by, for instance, Boc-P3-OH, may alternatively be substituted with the commercial CBz protected amino acids. Suitable deprotection conditions to remove the Cbz protecting groups are known to those skilled in the art. Likewise, the oxidation of intermediate 62 to compounds of formula ID-1 may be accomplished using other suitable conditions known to the skilled artisan.

Scheme 9:

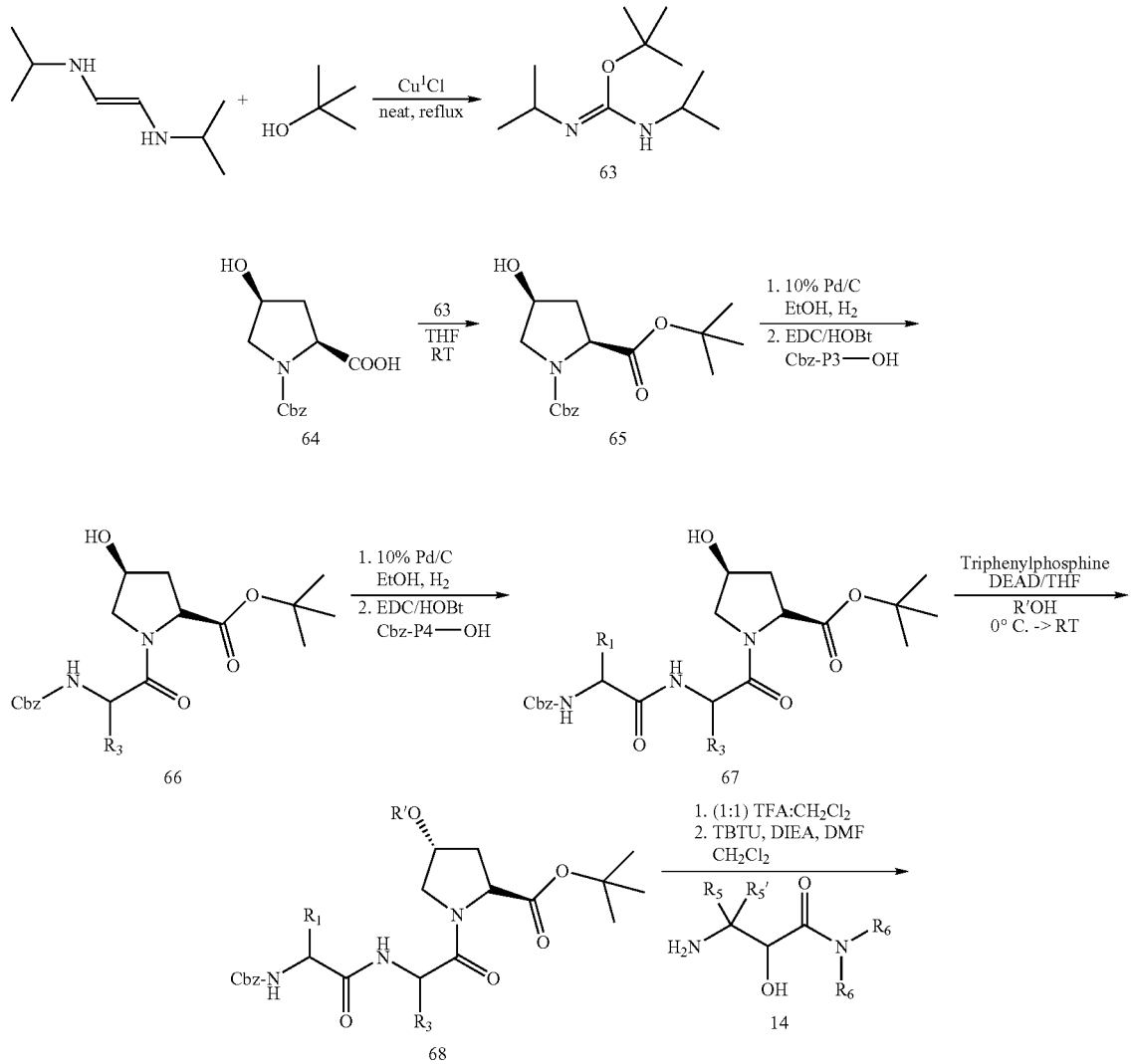

-continued

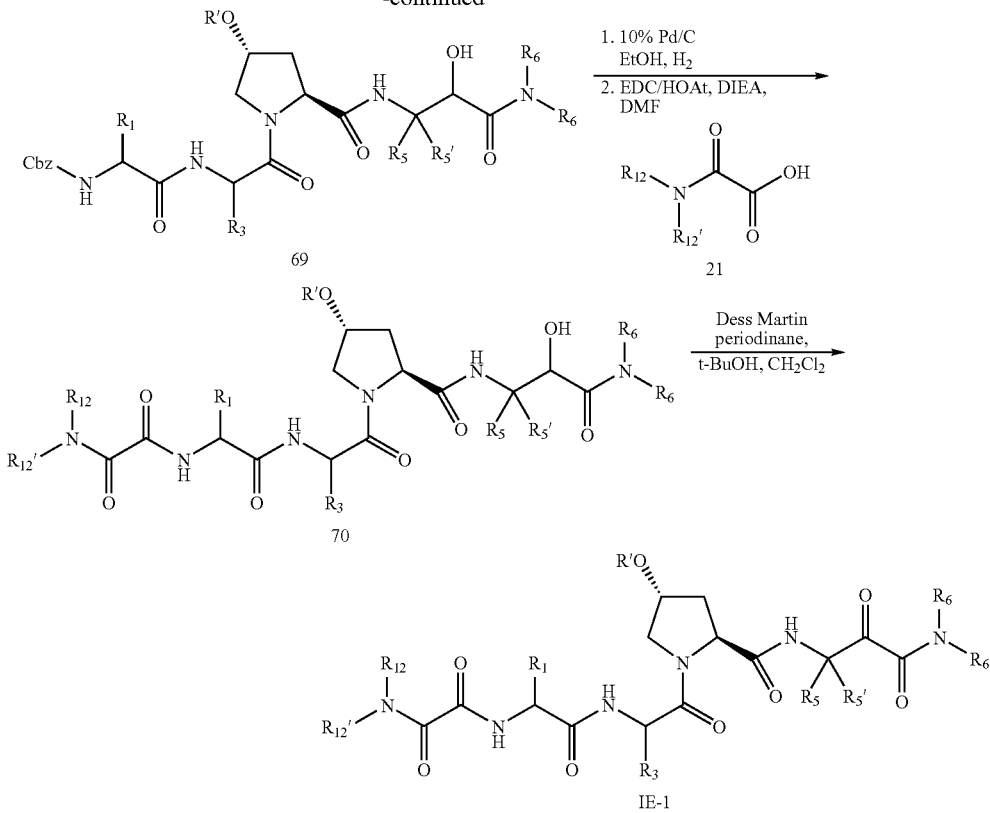

Scheme 9 above provides a general route for the preparation of compounds of formula IE-1 and formula IE, wherein X-V is —C(O)C(O)—, W is —C(O)C(O)—N($R_6$)$_2$, $R^2$, $R^4$, and $R^7$ are H, and R', $R^1$, $R^3$, $R^5$, $R^{5'}$, $R^6$, $R^{12}$, and $R^{12'}$ are as described in any of the embodiments herein. The steps used in scheme 9 could be modified by, for example, using different reagents or carrying out the reactions in a different order. As would be recognized by any skilled practitioner, other suitable and commercially available coupling reagents may be used to prepare intermediates 66, 67, 69, and 70. Additionally, it will be recognized that the commercially available Cbz protected amino acids represented by, for instance, Cbz-P3-OH, may alternatively be substituted with the commercial t-Boc protected amino acids. Suitable deprotection conditions to remove the Boc protecting groups are known to those skilled in the art. Likewise, the oxidation of intermediate 70 to compounds of formula IE-1 may be accomplished using other suitable conditions known to the skilled artisan.

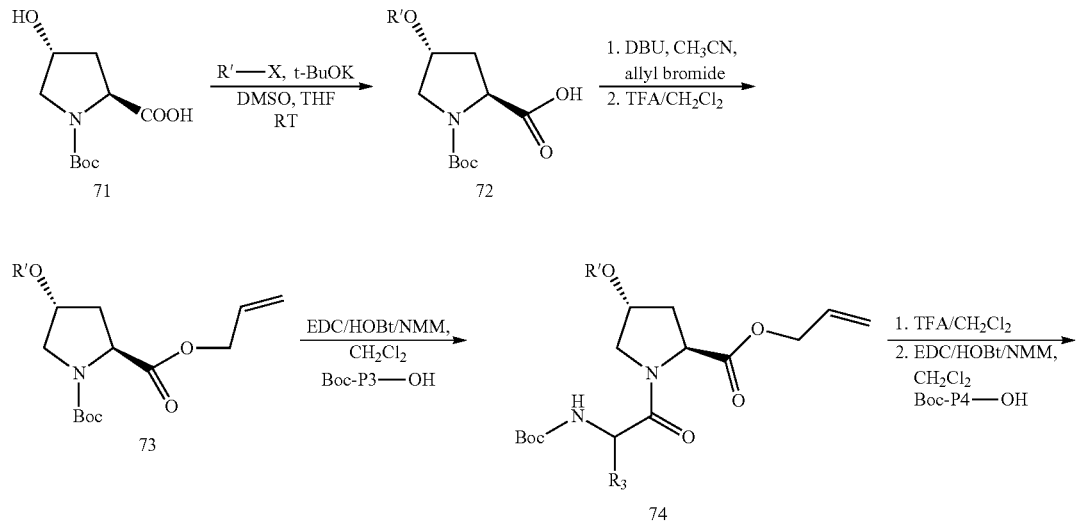

-continued

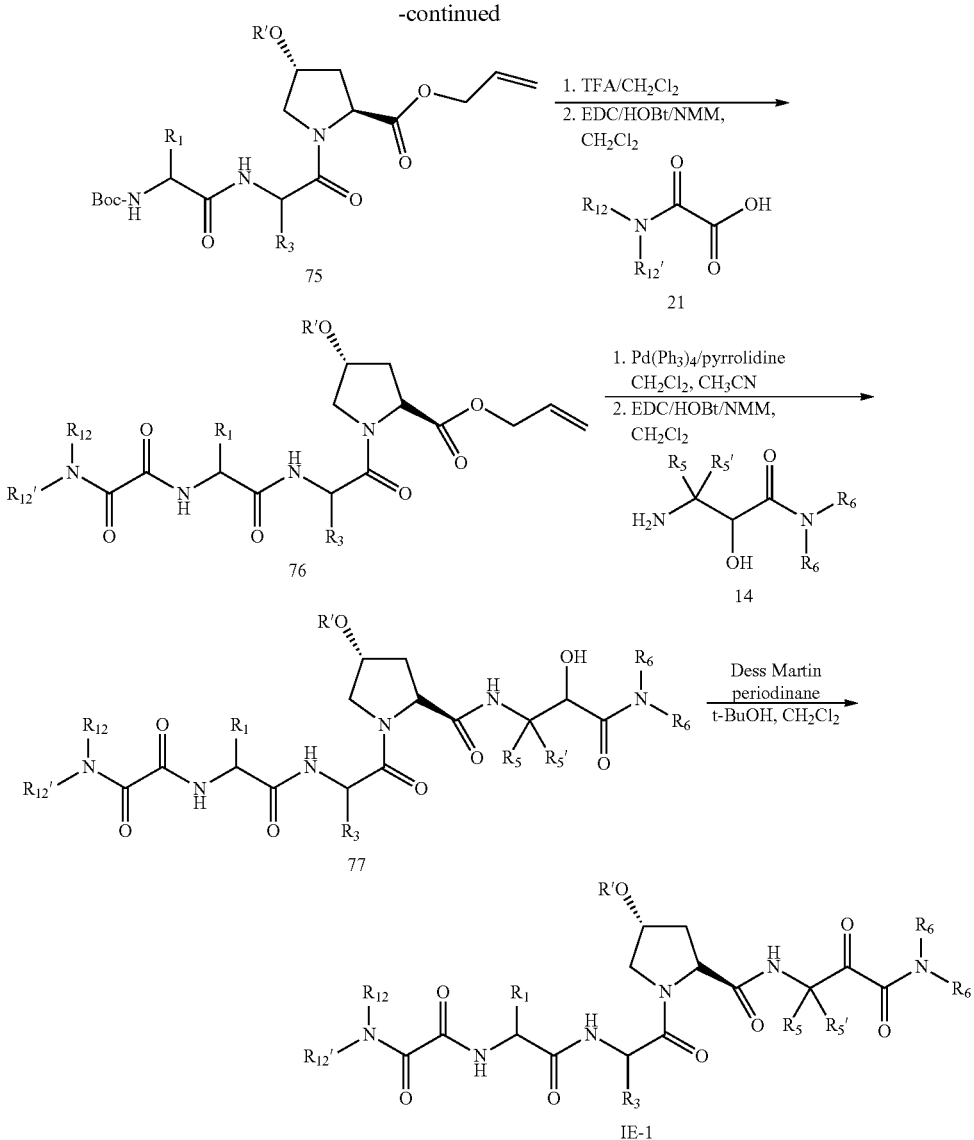

Scheme 10 above, depicts an alternative approach to preparing compounds of formulae IE-1 and IE of this invention wherein, X-V is —C(O)C(O)—, W is —C(O)C(O)—N($R_6$)$_2$; $R^2$, $R^4$, and $R^7$ are H, and R', $R^1$, $R^3$, $R^5$, $R^{5'}$, $R^6$, $R^{12}$, and $R^{12'}$ are as described in any of the embodiments herein. In this approach, a 4-hydroxyproline derivative 71 is reacted with a commercially available R'-halide (such an aryl chloride), represented by R'-X, in the presence of a suitable base (such as potassium t-butoxide) to provide a compound 72. As would be appreciated by any skilled practitioner, the compound 72 then may be carried on to compounds of formula IE-1 by routine methods. Additionally, other suitable and commercially available coupling reagents may be used to prepare intermediates 74, 75, 76, and 77. Furthermore, it will be recognized that the commercially available Boc protected amino acids represented by, for instance, Boc-P3-OH, may alternatively be substituted with the commercial CBz protected amino acids. Suitable deprotection conditions to remove the Cbz protecting groups are known to those skilled in the art. Likewise, the oxidation of intermediate 77 to compounds of formula IE-1 may be accomplished using other suitable conditions known to the skilled artisan.

Scheme 11:

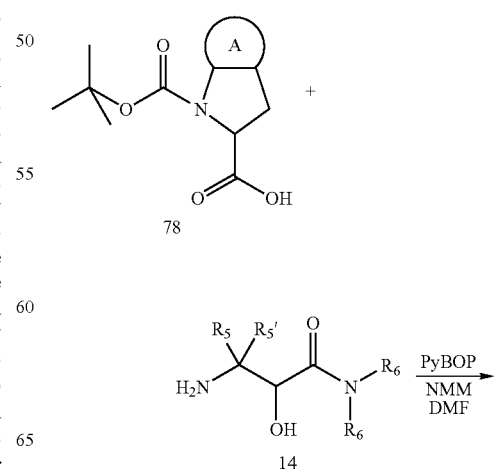

-continued

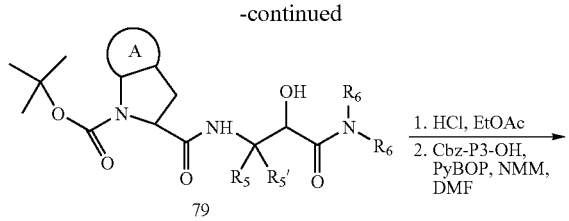
79

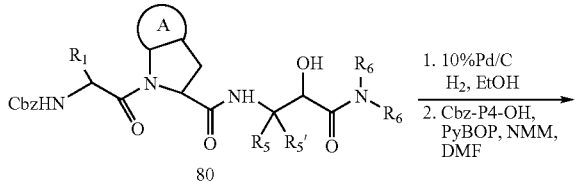
80

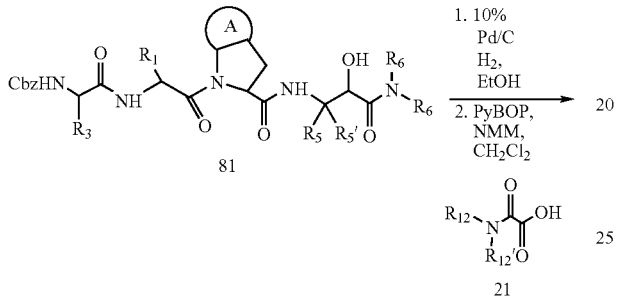
81

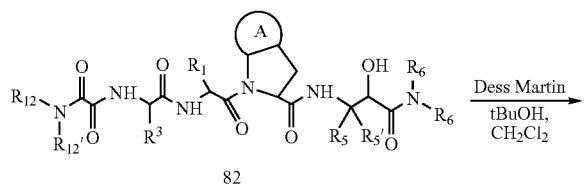
82

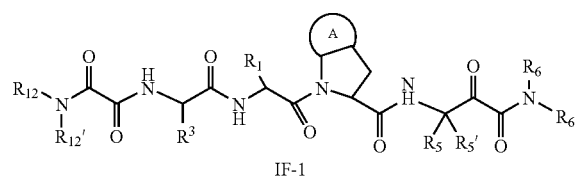
IF-1

Scheme 11 above provides a general route for the preparation of compounds of formula IF-1 and formula IF, wherein X-V is —C(O)C(O)—, W is —C(O)C(O)—N(R$_6$)$_2$, R$^2$, R$^4$, and R$^7$ are H, and ring A, R$^1$, R$^3$, R$^5$, R$^{5'}$, R$^6$, R$^{12}$, and R$^{12'}$ are as described in any of the embodiments herein. The steps used in scheme 11 could be modified by, for example, using different reagents or carrying out the reactions in a different order. As would be recognized by any skilled practitioner, other suitable and commercially available coupling reagents may be used to prepare intermediates 79, 80, 81, and 82. Additionally, it will be recognized that the commercially available Cbz protected amino acids represented by, for instance, Cbz-P3-OH, may alternatively be substituted with the commercial t-Boc protected amino acids. Suitable deprotection conditions to remove the Boc protecting groups are known to those skilled in the art. Likewise, the oxidation of intermediate 82 to compounds of formula IF-1 may be accomplished using other suitable conditions known to the skilled artisan.

Scheme 12:

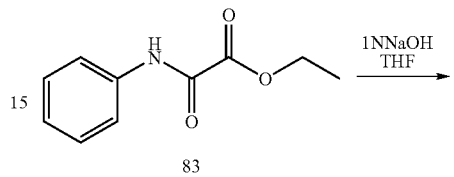
83

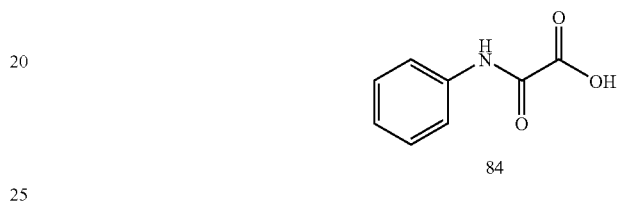
84

Scheme 12 above provides a synthetic route for the preparation of compound 84. Scheme 12 could be modified using techniques known to skilled practitioners to arrive at compound 84. Additionally, other commercially available oxalamide esters may be converted into the corresponding acids by a route analogous to that described above.

Scheme 13:

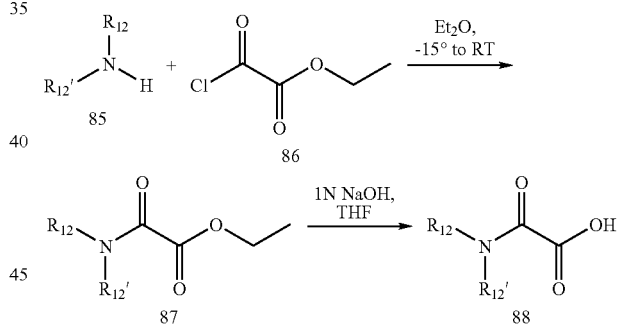

Scheme 13 provides a synthetic route for the preparation of non-commercially available oxalamide esters or oxalamide acids of interest. Scheme 13 may be modified using techniques known to skilled practitioners to arrive at compounds represented by formula 88.

Scheme 14:

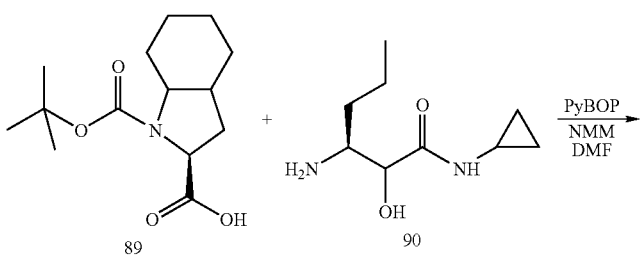

-continued
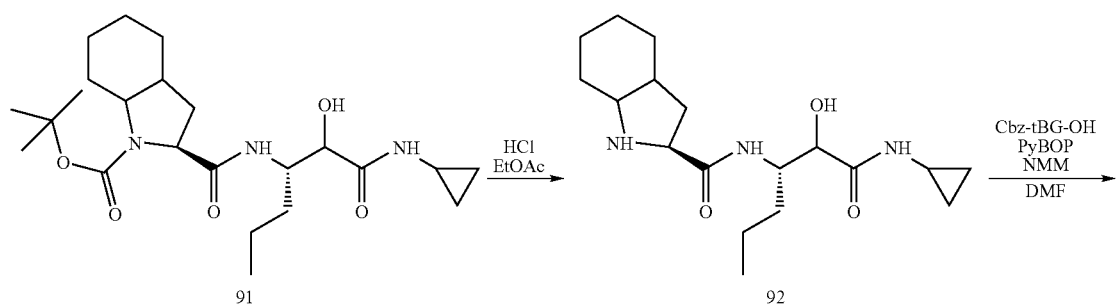
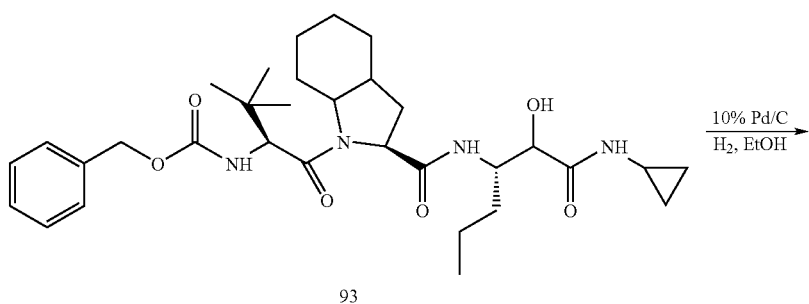
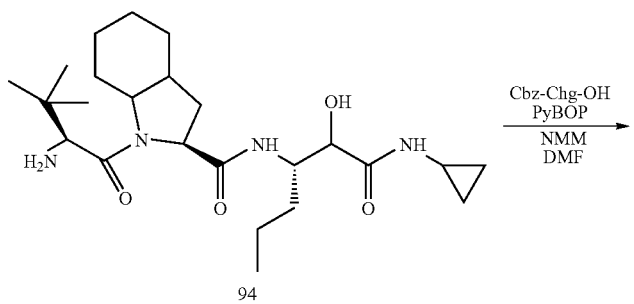
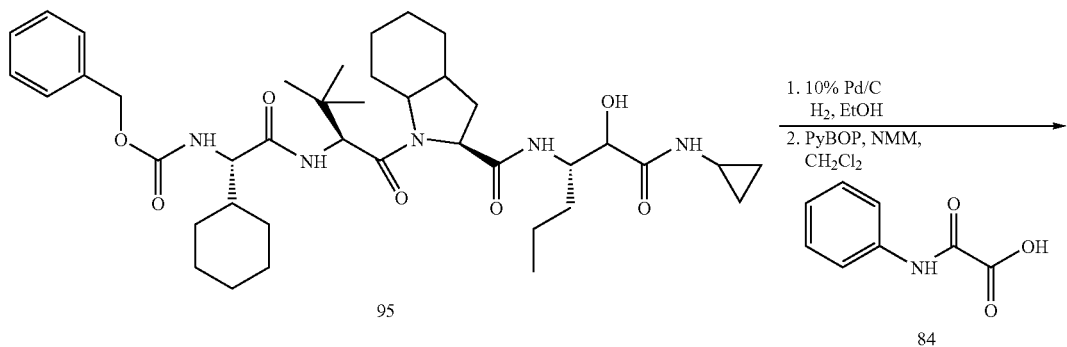
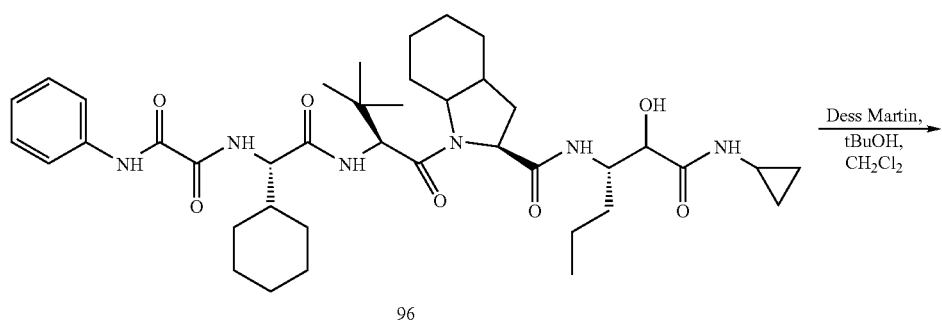

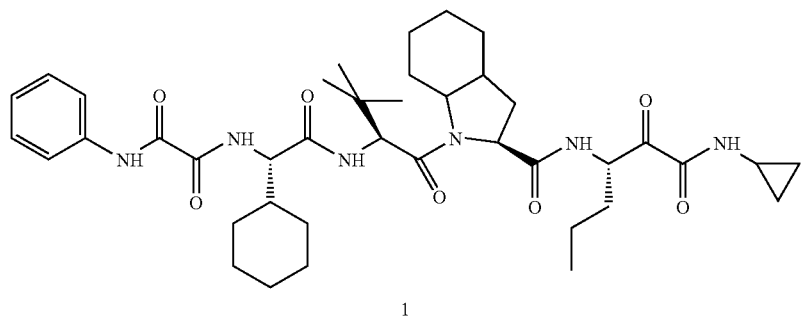

Scheme 14 above provides a synthetic route for the preparation of compound 1 from 89 (BOC-protected octahydro-indole-2-carboxylic acid). Intermediate 89 may be prepared from commercially available octahydro-indole-2-carboxylic acid (Bachem) according to the procedure described in PCT publication No. WO 03/087092 (the entire of contents of which is hereby incorporated by reference) and references cited therein. Scheme 14 could be modified using techniques known to skilled practitioners to arrive at compound 1. The experimental procedures to prepare compound 1 are further exemplified below in Example 2.

Scheme 15:

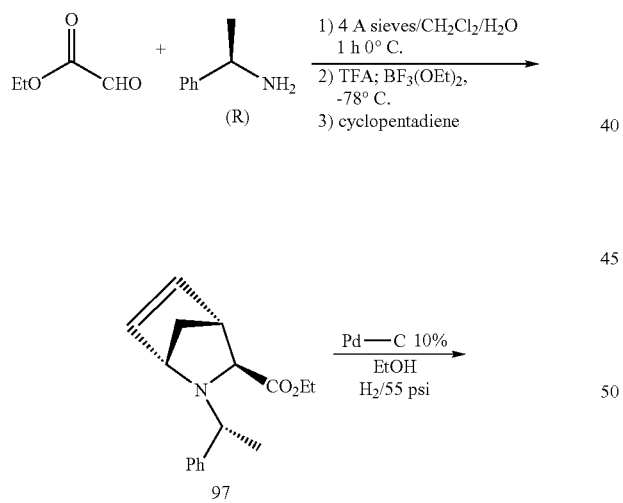

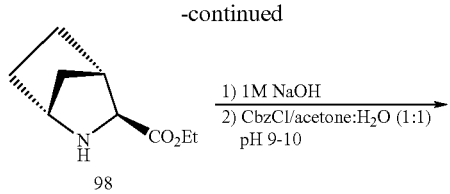

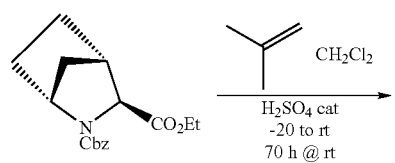

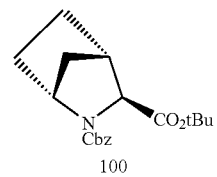

Scheme 15 above provides a synthetic route for the preparation of Cbz-protected azabicyclo[2.2.1]heptane-3-carboxylic acid, compound 99 and the corresponding t-butyl ester, compound 100. The free acid 99 may be further elaborated by the route defined in scheme 1 above to prepare compounds of formulae I and IH. Alternatively, the t-butyl ester 100 may be further elaborated by a modification of schemes 9 or 10 above to give compounds of formulae I and IH.

Scheme 16:

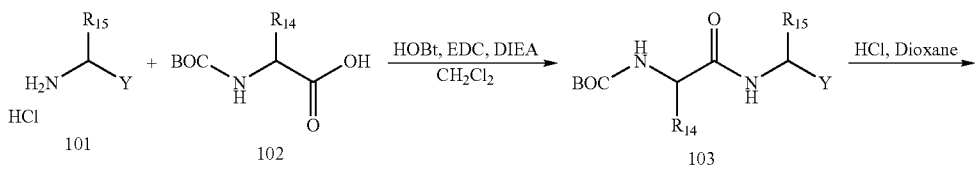

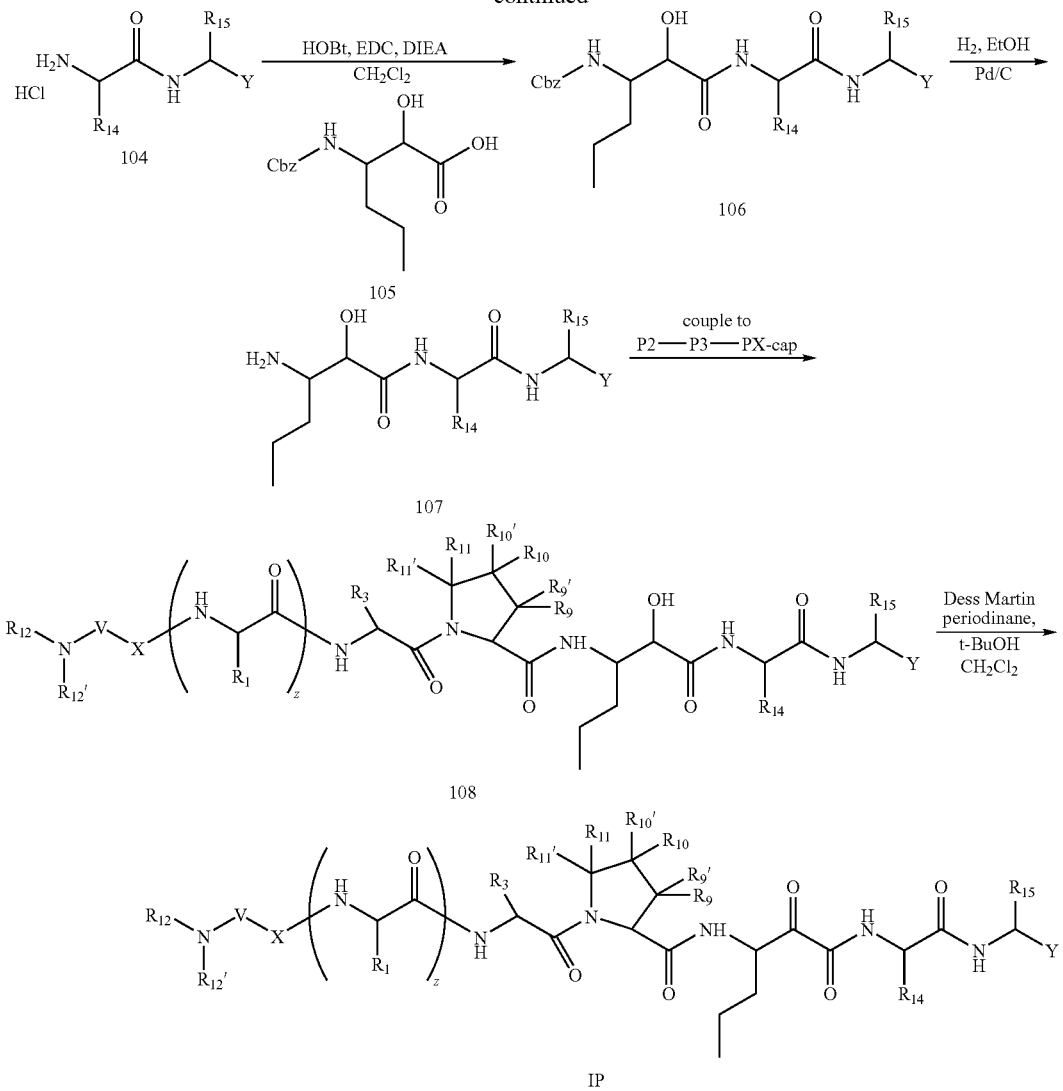

Scheme 16 above provides a general route for the preparation of compounds of formula IP and formula I-1, wherein $R^5$ is H, $R^{5'}$ is n-propyl, W is —C(O)C(O)—NH—C($R_{14}$)—C(O)—NH—C($R_{15}$)—Y, $R^2$, $R^4$, and $R^7$ are H, and ring A, X, V, $R^1$, $R^3$, $R^5$, $R^{5'}$, $R^6$, $R^9$, $R^{9'}$, $R^{10}$, $R^{10'}$, $R^{11}$, $R^{11'}$, $R^{14}$, $R^{15}$, Y, z, $R^{12}$, and $R^{12'}$ are as described in any of the embodiments herein. The steps used in scheme 16 could be modified by, for example, using different reagents or carrying out the reactions in a different order. As would be recognized by any skilled practitioner, other suitable and commercially available coupling reagents may be used to prepare intermediates 103, 106, and 108. Additionally, it will be recognized that the commercially available Cbz protected amino acids represented by, for instance, Cbz-$R_{14}$—COOH, may alternatively be substituted with the commercial t-Boc protected amino acids. Suitable deprotection conditions to remove the Boc protecting groups are known to those skilled in the art. Likewise, the oxidation of intermediate 108 to compounds of formula IP may be accomplished using other suitable conditions known to the skilled artisan. Intermediate acid 105 was prepared according to the procedure described by Harbeson, S. et al., J. Med. Chem., Vol. 37, No. 18, pp. 2918-2929 (1994).

The preparation of various other optionally substituted multicyclic azaheterocyclyl intermediates to prepare compounds of formulae I and IG via schemes 1, 9 or 10 above, may be accomplished by the methods described in PCT publication No. WO 02/18369 (the entire of contents of which is hereby incorporated by reference) and references cited therein.

Various 3, 4, and 5-substituted proline analogues may either be purchased commercially or prepared according to known literature procedures. For instance, for compounds of formula I wherein $R_{9'}$, is (C1-C12)-aliphatic-, the starting 3-substituted proline analogues may be prepared according to the method of Holladay, M. W. et al., J. Med. Chem., 34, pp. 457-461 (1991). For compounds of formula I wherein either $R_{9'}$, $R_{10'}$, or $R_{11'}$ are cyclohexyl and $R_9$, $R_{10}$, or $R_{11}$, are hydrogen, the cyclohexyl proline intermediates may be prepared by platinum oxide reduction of the commercially available phenyl substituted proline analogues. Such reduction conditions are well known to those skilled in the art.

For compounds of formula I wherein $R_{9'}$ is (C1-C12)-aliphatic- and Ro, is (C1-C12)-aliphatic-, the starting 3,4-disubstituted proline analogues may be prepared according to the method of Kanamasa, S. et al., J. Org. Chem., 56, pp. 2875-2883 (1991). In each of the syntheses involving 3, 4, or 5-substituted prolines or 3,4-disubstituted prolines, the intermediates may be further elaborated by the routes defined above in schemes 1, 9, or 10 to prepare compounds of formula I.

Accordingly, one embodiment of this invention provides a process for preparing a compound of formula I, as defined in any of the embodiments herein, comprising the step of: reacting a compound of formula VII in the presence of a compound of formula VIII to provide a compound of formula IX:

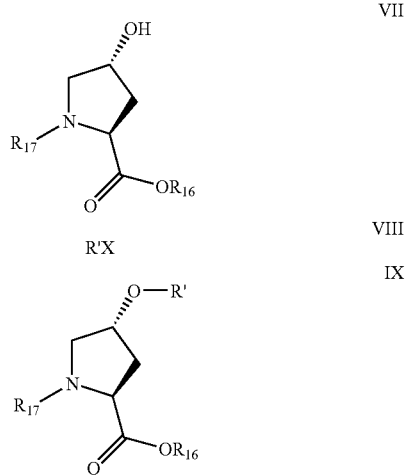

wherein:
$R_{17}$ is an amine protecting group, a P3-residue of an HCV protease inhibitor described herein, or a P4-P3-residue of an HCV protease inhibitor as described herein, and wherein the P3 and the P4-P3 residues are optionally substituted with an amino-terminal capping group;
$R_{16}$ is a carboxy protecting group or a P1 residue of an HCV protease inhibitor described herein, wherein the P1 residue is optionally substituted with a carboxy terminal protecting group or with W. R' is as defined in any of the embodiments herein. X is an appropriate leaving group. As would be appreciated by skilled practitioners, an appropriate leaving group may be generated in situ.

In an alternative embodiment, the 4-hydroxy group in formula VII may be converted to a leaving group. In such an embodiment, X is a nucleophilic oxygen which reacts with VII to provide IX.

As used herein, P1, P3, P4 refer to the residues of an HCV protease inhibitor as defined in the art and as are well known to skilled practitioners.

The compound of formula IX may be carried on to a compound of formula I according to the methods described herein.

Although certain embodiments are depicted and described below, it will be appreciated that compounds of this invention can be prepared according to the methods described generally above using appropriate starting materials generally available to one of ordinary skill in the art.

Another embodiment of this invention provides a pharmaceutical composition comprising a compound of formula I or formula I-1 or pharmaceutically acceptable salts thereof. According to another embodiment, the compound of formula I or formula I-1 is present in an amount effective to decrease the viral load in a sample or in a patient, wherein said virus encodes a serine protease necessary for the viral life cycle, and a pharmaceutically acceptable carrier.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentane-propionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to another embodiment, the compositions of this invention are formulated for pharmaceutical administration to a mammal. In one embodiment said mammal is a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In another embodiment, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In one embodiment, dosage levels of between about 0.01 and about 100 mg/kg body weight per day of the protease inhibitor compounds described herein are useful in a monotherapy for the prevention and treatment of antiviral, particularly anti-HCV mediated disease. In another embodiment, dosage levels of between about 0.5 and about 75 mg/kg body weight per day of the protease inhibitor compounds described herein are useful in a monotherapy for the prevention and treatment of antiviral, particularly anti-HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). In one embodiment, such preparations contain from about 20% to about 80% active compound.

When the compositions of this invention comprise a combination of a compound of formula I or formula I-1 and one or more additional therapeutic or prophylactic agents, both the compound and the additional agent should be present at dosage levels of between about 10 to 100% of the dosage normally administered in a monotherapy regimen. In another embodiment, the additional agent should be present at dosage levels of between about 10 to 80% of the dosage normally administered in a monotherapy regimen.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In one embodiment, the pharmaceutical compositions are formulated for oral administration.

In another embodiment, the compositions of this invention additionally comprise another anti-viral agent, preferably an anti-HCV agent. Such anti-viral agents include, but are not limited to, immunomodulatory agents, such as α-, β-, and γ-interferons, pegylated derivatized interferon-α compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including helicase and polymerase inhibitors; inhibitors of internal ribosome entry; broad-spectrum viral inhibitors, such as IMPDH inhibitors (e.g., compounds of U.S. Pat. Nos. 5,807, 876, 6,498,178, 6,344,465, 6,054,472, WO 97/40028, Wo 98/40381, WO 00/56331, and mycophenolic acid and derivatives thereof, and including, but not limited to VX-497, VX-148, and/or VX-944); or combinations of any of the above. See also W. Markland et al., Antimicrobial & Antiviral Chemotherapy, 44, p. 859 (2000) and U.S. Pat. No. 6,541, 496.

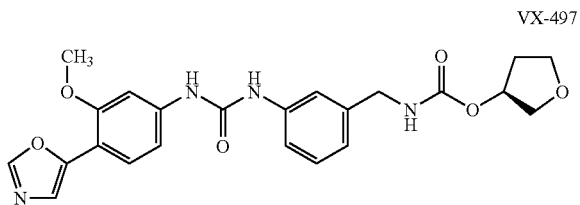 [SMILES: COc1cc(NC(=O)Nc2cccc(CNC(=O)O[C@H]3CCOC3)c2)ccc1-c1cnco1]

VX-497

The following definitions are used herein (with trademarks referring to products available as of this application's filing date).

"Peg-Intron" means PEG-Intron®, peginteferon alfa-2b, available from Schering Corporation, Kenilworth, N.J.;

"Intron" means Intron-A®, interferon alfa-2b available from Schering Corporation, Kenilworth, N.J.;

"ribavirin" means ribavirin (1-beta-D-ribofuranosyl-1H-1, 2,4-triazole-3-carboxamide, available from ICN Pharmaceuticals, Inc., Costa Mesa, Calif.; described in the Merck Index, entry 8365, Twelfth Edition; also available as Rebetol® from Schering Corporation, Kenilworth, N.J., or as Copegus® from Hoffmann-La Roche, Nutley, N.J.;

"Pagasys" means Pegasys®, peginterferon alfa-2a available Hoffmann-La Roche, Nutley, N.J.;

"Roferon" mean Roferon®, recombinant interferon alfa-2a available from Hoffmann-La Roche, Nutley, N.J.;

"Berefor" means Berefor®, interferon alfa 2 available from Boehringer Ingelheim Pharmaceutical, Inc., Ridgefield, Conn.;

Sumiferon®, a purified blend of natural alpha interferons such as Sumiferon available from Sumitomo, Japan;

Wellferon®, interferon alpha n1 available from Glaxo_Wellcome LTd., Great Britain;

Alferon®, a mixture of natural alpha interferons made by Interferon Sciences, and available from Purdue Frederick Co., CT;

The term "interferon" as used herein means a member of a family of highly homologous species-specific proteins that inhibit viral replication and cellular proliferation, and modulate immune response, such as interferon alpha, interferon beta, or interferon gamma. The Merck Index, entry 5015, Twelfth Edition.

According to one embodiment of the present invention, the interferon is α-interferon. According to another embodiment, a therapeutic combination of the present invention utilizes natural alpha interferon 2a. Or, the therapeutic combination of the present invention utilizes natural alpha interferon 2b. In another embodiment, the therapeutic combination of the present invention utilizes recombinant alpha interferon 2a or 2b. In yet another embodiment, the interferon is pegylated alpha interferon 2a or 2b. Interferons suitable for the present invention include:

(a) Intron (interferon-alpha 2B, Schering Plough),
(b) Peg-Intron,
(c) Pegasys,
(d) Roferon,
(e) Berofor,
(f) Sumiferon,
(g) Wellferon,
(h) consensus alpha interferon available from Amgen, Inc., Newbury Park, Calif.,
(i) Alferon;
(j) Viraferon®;
(k) Infergen®.

As is recognized by skilled practitioners, a protease inhibitor would be preferably administered orally. Interferon is not typically administered orally. Nevertheless, nothing herein limits the methods or combinations of this invention to any specific dosage forms or regime. Thus, each component of a combination according to this invention may be administered separately, together, or in any combination thereof.

In one embodiment, the protease inhibitor and interferon are administered in separate dosage forms. In one embodiment, any additional agent is administered as part of a single dosage form with the protease inhibitor or as a separate dosage form. As this invention involves a combination of compounds, the specific amounts of each compound may be dependent on the specific amounts of each other compound in the combination. As recognized by skilled practitioners, dosages of interferon are typically measured in IU (e.g., about 4 million IU to about 12 million IU).

Accordingly, agents (whether acting as an immunomodulatory agent or otherwise) that may be used in combination with a compound of this invention include, but are not limited to, interferon-alph 2B (Intron A, Schering Plough); Rebatron (Schering Plough, Inteferon-alpha 2B+Ribavirin); pegylated interferon alpha (Reddy, K. R. et al. "Efficacy and Safety of Pegylated (40-kd) interferon alpha-2a compared with interferon alpha-2a in noncirrhotic patients with chronic hepatitis C (*Hepatology*, 33, pp. 433-438 (2001); consensus interferon (Kao, J. H., et al., "Efficacy of Consensus Interferon in the Treatement of Chronic Hepatitis" J. Gastroenterol. Hepatol. 15, pp. 1418-1423 (2000), interferon-alpha 2A (Roferon A; Roche), lymphoblastoid or "natural" interferon; interferon tau (Clayette, P. et al., "IFN-tau, A New Interferon Type I with Antiretroviral activity" Pathol. Biol. (Paris) 47, pp. 553-559 (1999); interleukin 2 (Davis, G. L. et al., "Future Options for the Management of Hepatitis C." Seminars in Liver Disease, 19, pp. 103-112 (1999); Interleukin 6 (Davis et al. "Future Options for the Management of Hepatitis C." Seminars in Liver Disease 19, pp. 103-112 (1999); interleukin 12 (Davis, G. L. et al., "Future Options for the Management of Hepatitis C." Seminars in Liver Disease, 19, pp. 103-112 (1999); Ribavirin; and compounds that enhance the development of type 1 helper T cell response (Davis et al., "Future Options for the Management of Hepatitis C." Seminars in Liver Disease, 19, pp. 103-112 (1999). Interferons may ameliorate viral infections by exerting direct antiviral effects and/or by modifying the immune response to infection. The antiviral effects of interferons are often mediated through inhibition of viral penetration or uncoating, synthesis of viral RNA, translation of viral proteins, and/or viral assembly and release.

Compounds that stimulate the synthesis of interferon in cells (Tazulakhova, E. B. et al., "Russian Experience in Screening, analysis, and Clinical Application of Novel Interferon Inducers" J. Interferon Cytokine Res., 21 pp. 65-73) include, but are not limited to, double stranded RNA, alone or in combination with tobramycin, and Imiquimod (3M Pharmaceuticals; Sauder, D. N. "Immunomodulatory and Pharmacologic Properties of Imiquimod" J. Am. Acad. Dermatol., 43 pp. S6-11 (2000).

Other non-immunomodulatory or immunomodulatory compounds may be used in combination with a compound of this invention including, but not limited to, those specified in WO 02/18369, which is incorporated herein by reference (see, e.g., page 273, lines 9-22 and page 274, line 4 to page 276, line 11).

This invention may also involve administering a cytochrome P450 monooxygenase inhibitor. CYP inhibitors may be useful in increasing liver concentrations and/or increasing blood levels of compounds that are inhibited by CYP.

If an embodiment of this invention involves a CYP inhibitor, any CYP inhibitor that improves the pharmacokinetics of the relevant NS3/4A protease may be used in a method of this invention. These CYP inhibitors include, but are not limited to, ritonavir (WO 94/14436), ketoconazole, troleandomycin, 4-methylpyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methylpyrazole, cyclosporin, and clomethiazole. For preferred dosage forms of ritonavir, see U.S. Pat. No. 6,037,157, and the documents cited therein: U.S. Pat. No. 5,484,801, U.S. application Ser. No. 08/402,690, and International Applications Wo 95/07696 and WO 95/09614).

Methods for measuring the ability of a compound to inhibit cytochrome P50 monooxygenase activity are known (see U.S. Pat. No. 6,037,157 and Yun, et al. Drug Metabolism & Disposition, vol. 21, pp. 403-407 (1993).

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular described compound and the presence or absence and the nature of the additional anti-viral agent in the composition.

According to another embodiment, the invention provides a method for treating a patient infected with a virus characterized by a virally encoded serine protease that is necessary for the life cycle of the virus by administering to said patient a pharmaceutically acceptable composition of this invention. In another embodiment the methods of this invention are used to treat a patient suffering from a HCV infection. Such treatment may completely eradicate the viral infection or reduce the severity thereof. In one embodiment, the patient is a human being.

In an alternate embodiment, the methods of this invention additionally comprise the step of administering to said patient an anti-viral agent preferably an anti-HCV agent. Such antiviral agents include, but are not limited to, immunomodulatory agents, such as $\alpha$-, $\beta$-, and $\gamma$-interferons, pegylated derivatized interferon-$\alpha$ compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including helicase and polymerase inhibitors; inhibitors of internal ribosome entry; broad-spectrum viral inhibitors, such as IMPDH inhibitors (e.g., VX-497 and other IMPDH inhibitors disclosed in U.S. Pat. Nos. 5,807,876 and 6,498,178, mycophenolic acid and derivatives thereof); inhibitors of cytochrome P-450, such as ritonavir, or combinations of any of the above.

Such additional agent may be administered to said patient as part of a single dosage form comprising both a compound of this invention and an additional anti-viral agent. Alternatively the additional agent may be administered separately from the compound of this invention, as part of a multiple dosage form, wherein said additional agent is administered prior to, together with or following a composition comprising a compound of this invention.

In yet another embodiment the present invention provides a method of pre-treating a biological substance intended for administration to a patient comprising the step of contacting said biological substance with a pharmaceutically acceptable composition comprising a compound of this invention. Such biological substances include, but are not limited to, blood and components thereof such as plasma, platelets, subpopulations of blood cells and the like; organs such as kidney, liver, heart, lung, etc; sperm and ova; bone marrow and components thereof, and other fluids to be infused into a patient such as saline, dextrose, etc.

According to another embodiment the invention provides methods of treating materials that may potentially come into contact with a virus characterized by a virally encoded serine protease necessary for its life cycle. This method comprises the step of contacting said material with a compound according to the invention. Such materials include, but are not limited to, surgical instruments and garments (e.g. clothes, gloves, aprons, gowns, masks, eyeglasses, footwear, etc.); laboratory instruments and garments (e.g. clothes, gloves, aprons, gowns, masks, eyeglasses, footwear, etc.); blood collection apparatuses and materials; and invasive devices, such as shunts, stents, etc.

In another embodiment, the compounds of this invention may be used as laboratory tools to aid in the isolation of a virally encoded serine protease. This method comprises the steps of providing a compound of this invention attached to a solid support; contacting said solid support with a sample containing a viral serine protease under conditions that cause said protease to bind to said solid support; and eluting said serine protease from said solid support. Preferably, the viral serine protease isolated by this method is HCV NS3-NS4A protease.

In order that this invention be more fully understood, the following preparative and testing examples are set forth. These examples are for the purpose of illustration only and are not to be construed as limiting the scope of the invention in any way.

EXAMPLES $^1$H-NMR spectra were recorded at 500 MHz using a Bruker AMX 500 instrument. Mass spec. samples were analyzed on a MicroMass ZQ or Quattro II mass spectrometer operated in single MS mode with electrospray ionization. Samples were introduced into the mass spectrometer using flow injection (FIA) or chromatography. Mobile phase for all mass spec. analysis consisted of acetonitrile-water mixtures with 0.2% formic acid as a modifier.

As used herein, the term "$R_t$ (min)" refers to the HPLC retention time, in minutes, associated with the compound. The HPLC retention times listed were either obtained from the mass spec. data or using the following method:
Instrument: Hewlett Packard HP-1050;
Column: YMC $C_{18}$ (Cat. No. 326289C46);
Gradient/Gradient Time: 10-90% $CH_3CN/H_2O$ over 9 minutes, then 100% $CH_3CN$ for 2 minutes;
Flow Rate: 0.8 ml/min;
Detector Wavelength: 215 nM and 245 nM.

Chemical naming for selected compounds herein was accomplished using the naming program provided by CambridgeSoft Corporations ChemDraw Ultra®, version 7.0.1.

Example 1

N-Phenyl Oxalamic Acid (84)

Ethyl oxanilate 83 (Aldrich, 1.0 g, 1.0 eq) in 12 mL of THF was treated dropwise with a 1N NaOH solution (5.70 mL, 1.1 eq) resulting in a white precipitate. After stirring for 3 hours at RT, 0.5N HCl and ethyl acetate were added, the organic layer separated, washed with 0.5N HCl and brine and then dried over sodium sulfate, filtered, and concentrated to give 712 mg (68%) of N-phenyl oxalamic acid 84 as a white solid with consistent analytical data. FIA M+H=166.0, M−H=163.9; $^1$H NMR (DMSO-$d_6$) δ 10.70 (s, 1H), 7.75 (m, 2H), 7.35 (m, 2H), 7.15 (m, 1H) ppm.

Example 2

N-(Cyclohexyl-{1-[2-(1-cyclopropylaminooxalyl-butylcarbamoyl)-octahydro-indole-1-carbonyl]-2,2-dimethyl-propylcarbamoyl}-N'-phenyl-oxalamide
(1)

Octahydro-indole-1,2-dicarboxylic acid 1-tert-butyl ester 89 (Bachem, 1.6 g, 1.0 eq) in DMF (20 mL) was treated with PyBOP (3.41 g, 1.1 eq) and NMM (1.97 mL, 3.0 eq). To this was added 3-amino-2-hydroxy-hexanoic acid cyclopropylamide 90 (1.22 g, 1.1 eq, prepared according to the procedure of U. Schoellkogf et al., Justus Liebigs Ann. Chem. GE, pp. 183-202 (1976) and J. Semple et al., Org. Letters, 2, pp. 2769-2772 (2000) and NMM (1.97 mL, 3.0 eq) in DMF (3 mL) and the mixture stirred at rt overnight. The mixture was evaporated in vacuo, diluted with ethyl acetate, the organic phase washed with 0.5N HCl, sodium bicarbonate and brine, then dried over sodium sulfate, filtered and concentrated in vacuo to give 2-[1-cyclopropylcarbamoyl-hydroxy-methyl)-butylcarbamoyl]-octahydro-indole-1-carboxylic acid tert-butyl ester 91 which was used without further purification. $^1$H NMR (CDCl$_3$) δ 6.92 (bs, 1H), 6.80 (bs, 1H), 3.80-4.20 (m, 3H), 2.75 (m, 1H), 2.25 (m, 1H), 2.10 (m, 1H), 1.90-2.00 (m, 2H), 1.5-1.75 (m, 7H), 1.45 (s, 9H), 1.10-1.40 (m, 5H), 0.90 (m, 3H), 0.75 (m, 2H), 0.50 (m, 2H) ppm.

Crude Boc amide 91 was stirred in ethyl acetate (0.5N), treated with anhydrous 2N HCl in EtOAc and the mixture stirred for 2 hours. The mixture was concentrated in vacuo to give octahydro-indole-2-carboxylic acid [1-(cyclopropylcarbamoyl-hydroxy-methyl)butyl]-amide 92 which was used without further purification. $^1$H NMR (CDCl$_3$) δ 7.10 (bs, 1H), 6.95 (bs, 1H), 4.60 (m, 1H), 4.30 (m, 1H), 3.85 (m, 1H), 2.75 (m, 1H), 2.50 (m, 2H), 2.05 (m, 2H), 1.30-1.80 (m, 12H), 0.90 (m, 3H), 0.80 (m, 2H), 0.60 (m, 2H) ppm.

CBz tert-butyl glycine (1.74 g, 1.1 eq), and crude amine 92 (2.01 g, 1.0 eq) in DMF (20 mL) were treated with PyBOP (3.41 g, 1.1 eq) and NMM (3.93 mL, 6.0 eq) and the mixture stirred overnight at room temperature. The reaction mixture was concentrated in vacuo, diluted with EtOAc and the organic layer washed with 0.5N HCl, brine, sodium bicarbonate solution and brine, then dried over sodium sulfate, filtered, and concentrated in vacuo. Purification on Merck silica gel eluting with a gradient (20% EtOAc/Hexanes to 100% EtOAc) afforded 2.295 g (66%) of (1-{2-[1-(cyclopropylcarbamoyl-hydroxy-methyl)-butylcarbamoyl]-octahydro-indole-1-carbonyl}-2,2-dimethyl-propyl)-carbamic acid benzyl ester 93 as an oil with consistent analytical data. LCMS ret time=4.09 min, M+H=585.28, M−H=583.25; $^1$H NMR (CDCl$_3$) δ 7.32 (m, 5H), 6.99 (d, 1H), 6.85 (m, 1H), 5.42 (d, 1H), 5.02-5.12 (m, 2H), 4.50 (t, 1H), 4.25 (d, 1H), 4.09 (m, 1H), 3.95 (m, 1H), 2.72 (m, 1H), 2.12-2.30 (m, 2H), 1.95 (m, 2H), 1.59-1.81 (m, 6H), 1.50 (m, 2H), 1.22-1.42 (m, 4H), 1.00 (s, 9H), 0.90 (m, 3H), 0.75 (m, 2H), 0.55 (m, 2H) ppm.

Amide 93 (10.10 g, 1.0 eq) in EtOH (10 mL) was treated with 10% Pd/C (100 mg) and hydrogen gas was bubbled into the black suspension until starting material was consumed (monitored by TLC). Catalyst was removed by filtration and the filtrate concentrated in vacuo to give 852 mg (100% yield) of 1-(2-amino-3,3-dimethyl-butyryl)-octahydro-indole-2-carboxylic acid [1-(cyclopropylcarbamoyl-hydroxy-methyl)-butyl]-amide 94 as a white solid with consistent NMR data. $^1$H NMR (CDCl$_3$) δ 4.40 (m, 1H), 4.20 (m, 1H), 4.10 (d, 1H), 3.95 (m, 1H), 2.70 (m, 1H), 2.40 (m, 2H), 2.0 (m, 2H), 1.60-1.80 (m, 6H), 1.50 (m, 2H), 1.30 (m, 3H), 1.20 (m, 1H), 1.00 (s, 9H), 0.90 (m, 3H), 0.75 (m, 2H), 0.55 (m, 2H) ppm.

CBz-cyclohexylglycine (Bachem, 747 mg, 1.05 eq) in DMF (5 mL) was treated with PyBOP (1.33 g, 1.05 eq) and NMM (0.8 ml, 3.0 eq). To this was added a solution of amine 94 (1.1 g, 1.0 eq) and NMM (0.8 mL, 3.0 eq) in DMF (20 mL) and the mixture stirred at room temperature for 3 hours. The reaction mixture was concentrated in vacuo, diluted with ethyl acetate, the organic phase washed with 0.5N HCl, brine, saturated sodium bicarbonate solution, and brine, then dried over sodium sulfate, filtered, and concentrated in vacuo. Purification via Merck silica gel eluting with 75% EtOAc/Hexanes afforded 1.18 g (67%) of [cyclohexyl-(1-{2-[1-cyclopropylcarbamoyl-hydroxy-methyl)-butylcarbamoyl]-octahydro-indole-1-carbonyl}-2,2-dimethyl-propylcarbamoyl)methyl]-carbamic acid benzyl ester 95 as a white solid with consistent analytical data. LCMS ret time=3.65, M+H=724.22, M−H=722.20;

$^1$H NMR (CDCl$_3$) δ 7.35 (m, 5H), 7.05 (m, 1H), 6.90 (m, 1H), 6.55 (m, 1H), 5.35 (dd, 1), 5.10 (m, 2H), 4.35-4.55 (m, 1H), 3.95-4.25 (3H), 2.75 (m, 1H), 2.20 (m, 1H), 2.00 (m, 1H), 1.65-1.80 (m, 7H), 1.55 (m, 2H), 1.05-1.45 (m, 7H), 1.00 (s, 9H), 0.85-1.00 (m, 7H), 0.80 (m, 2H), 0.55 (m, 2H) ppm.

CBz carbamate 95 (1.76 g, 1.0 eq) in EtOH (12 mL). was treated with 10% Pd/C (175 mg) and hydrogen gas was bubbled through the suspension until starting material was consumed (monitored by TLC). Catalyst was removed by filtration and the filtrate concentrated in vacuo to give 1.43 g (100%) of intermediate oxalamide as a white solid which was used without further purification.

Acid 84 (20 mg, 1.4 eq) in CH$_2$Cl$_2$ (1 mL) was treated with PyBOP (53 mg, 1.2 eq) and NMM (0.028 mL, 3.0 eq) and stirred for 5 minutes. To this was added a solution of oxalamide (50 mg, 1.0 eq) and NMM (0.028 mL, 3.0 eq) in CH$_2$Cl$_2$ (1 mL) and the mixture stirred at room temperature overnight. The mixture was diluted with ethyl acetate, the organic phase washed with 0.5N HCl, brine, saturated bicarbonate solution, and brine, then dried over sodium sulfate, filtered and concentrated in vacuo. Purification by preparative HPLC yielded 24 mg (38%) of N-[cyclohexyl-(1-{2-[1-cyclopropylcarbamoyl-hydroxy-methyl)-butylcarbamoyl]-octahydro-indole-1-carbonyl}-2,2-dimethyl-propylcarbamoyl)methyl]-N'-phenyl-oxalamide 96 as a white solid with consistent analytical data. LCMS ret time=4.07, M+H=737.26, M−H=735.22.

Oxalamide 96 (24 mg, 1.0 eq) in CH$_2$Cl$_2$ (1 mL) and t-BuOH (41 uL) was treated with Dess Martin periodinane (41 mg, 3.0 eq) and the suspension stirred at room temp. for 3 hours. Sodium thiosulfate was added and the mixture stirred for 15 minutes, then diluted with ethyl acetate, the organic phase washed with sodium bicarbonate solution and brine, then dried over anhydrous sodium sulfate and concentrated in vacuo. Purification by preparative HPLC yielded 5.5 mg (23%) of N-(cyclohexyl-{1-[2-(1-cyclopropylaminooxalyl-butylcarbamoyl)-octahydro-indole-1-carbonyl]-2,2-dimethyl-propylcarbamoyl}-N'-phenyl-oxalamide 1 as a white solid with consistent analytical data. LCMS ret time=4.51, M+H=735.23, M−H=733.39.

Example 3

HCV Replicon Cell Assay Protocol:

Cells containing hepatitis C virus (HCV) replicon were maintained in DMEM containing 10% fetal bovine serum (FBS), 0.25 mg per ml of G418, with appropriate supplements (media A).

On day 1, replicon cell monolayer was treated with a trypsin: EDTA mixture, removed, and then media A was diluted into a final concentration of 100,000 cells per ml wit. 10,000 cells in 100 ul were plated into each well of a 96-well tissue culture plate, and cultured overnight in a tissue culture incubator at 37° C.

On day 2, compounds (in 100% DMSO) were serially diluted into DMEM containing 2% FBS, 0.5% DMSO, with appropriate supplements (media B). The final concentration of DMSO was maintained at 0.5% throughout the dilution series.

Media on the replicon cell monolayer was removed, and then media B containing various concentrations of compounds was added. Media B without any compound was added to other wells as no compound controls.

Cells were incubated with compound or 0.5% DMSO in media B for 48 hours in a tissue culture incubator at 37° C. At the end of the 48-hour incubation, the media was removed, and the replicon cell monolayer was washed once with PBS and stored at −80° C. prior to RNA extraction.

Culture plates with treated replicon cell monolayers were thawed, and a fixed amount of another RNA virus, such as Bovine Viral Diarrhea Virus (BVDV) was added to cells in each well. RNA extraction reagents (such as reagents from RNeasy kits) were added to the cells immediately to avoid degradation of RNA. Total RNA was extracted according the instruction of manufacturer with modification to improve extraction efficiency and consistency. Finally, total cellular RNA, including HCV replicon RNA, was eluted and stored at −80° C. until further processing.

A Taqman real-time RT-PCR quantification assay was set up with two sets of specific primers and probe. One was for HCV and the other was for BVDV. Total RNA extractants from treated HCV replicon cells was added to the PCR reactions for quantification of both HCV and BVDV RNA in the same PCR well. Experimental failure was flagged and rejected based on the level of BVDV RNA in each well. The level of HCV RNA in each well was calculated according to a standard curve run in the same PCR plate. The percentage of inhibition or decrease of HCV RNA level due to compound treatment was calculated using the DMSO or no compound control as 0% of inhibition. The $IC_{50}$ (concentration at which 50% inhibition of HCV RNA level is observed) was calculated from the titration curve of any given compound.

Example 4

HCV Enzyme Assay Protocol
HPLC Microbore Method for Separation of 5AB Substrate and Products
Substrate:
NH$_2$-Glu-Asp-Val-Val-(alpha)Abu-Cys-Ser-Met-Ser-Tyr-COOH A stock solution of 20 mM 5AB (or concentration of your choice) was made in DMSO w/0.2M DTT. This was stored in aliquots at −20 C.

Buffer: 50 mM HEPES, pH 7.8; 20% glycerol; 100 mM NaCl

Total assay volume was 100 μL

| Reagent | X1 (μL) | conc. in assay |
|---|---|---|
| Buffer | 86.5 | see above |
| 5 mM KK4A | 0.5 | 25 μM |
| 1 M DTT | 0.5 | 5 mM |
| DMSO or inhibitor | 2.5 | 2.5% v/v |
| 50 μM tNS3 | 0.05 | 25 nM |
| 250 μM 5AB (initiate) | 20 | 25 μM |

The buffer, KK4A, DTT, and tNS3 were combined; distributed 78 μL each into wells of 96 well plate. This was incubated at 30 C for ~5-10 min.

2.5 μL of appropriate concentration of test compound was dissolved in DMSO (DMSO only for control) and added to each well. This was incubated at room temperature for 15 min.

Initiated reaction by addition of 20 μL of 250 μM 5AB substrate (25 μM concentration is equivalent or slightly lower than the Km for 5AB).

Incubated for 20 min at 30 C.
Terminated reaction by addition of 25 μL of 10% TFA
Transferred 120 μL aliquots to HPLC vials
Separated SMSY product from substrate and KK4A by the following method:
Microbore Separation Method:
Instrumentation: Agilent 1100
Degasser G1322A
Binary pump G1312A
Autosampler G1313A
Column thermostated chamber G1316A
Diode array detector G1315A
Column:
Phenomenex Jupiter; 5 micron C18; 300 angstroms; 150×2 mm; P/O 00F-4053-B0
Column thermostat: 40 C
Injection volume: 100 μL
Solvent A=HPLC grade water+0.1% TFA
Solvent B=HPLC grade acetonitrile+0.1% TFA

| Time (min) | % B | Flow (ml/min) | Max press. |
|---|---|---|---|
| 0 | 5 | 0.2 | 400 |
| 12 | 60 | 0.2 | 400 |
| 13 | 100 | 0.2 | 400 |
| 16 | 100 | 0.2 | 400 |
| 17 | 5 | 0.2 | 400 |

Stop time: 17 min
Post-run time: 10 min.

Table 1 below depicts Mass Spec., HPLC, Ki and $IC_{50}$ data for certain compounds of the invention. Compounds with Ki's ranging from 0.25 μM to 1 μM are designated A. Compounds with Ki's ranging from 0.1 μM to 0.25 μM are designated B. Compounds with Ki's below 0.1 μM are designated C. Compounds with $IC_{50}$'s ranging from 0.25 μM to 1 μM are designated A. Compounds with $IC_{50}$'s ranging from 0.1 μM to 0.25 μM are designated B. Compounds with $IC_{50}$'s below 0.1 μM are designated C.

TABLE 1

| Compound | MS+ | HPLC, $R_t$ (min) | Ki | $IC_{50}$ |
|---|---|---|---|---|
| 1 | 735.2 | 4.51 | B | A |
| 2 | 749.3 | 4.54 | B | A |
| 3 | 755.4 | 4.92 | B | A |
| 4 | 699.3 | 4.04 | B | A |
| 5 | 701.3 | 4.15 | B | A |
| 6 | 715.2 | 4.34 | B | A |
| 7 | 740.2 | 4.19 | B | A |
| 8 | 741.4 | 4.88 | B | A |
| 9 | 727.4 | 4.69 | A | A |
| 10 | 772.3 | 4.30 | B | C |
| 11 | 822.1 | 4.80 | B | C |
| 12 | 788.0 | 4.70 | B | C |

Table 2 below depicts proton NMR data for certain compounds of the invention. $^1$H-NMR spectra were recorded at 500 MHz using a Bruker AMX 500 instrument.

TABLE 2

| Compound | $^1$H-NMR (500 MHz) |
|---|---|
| 1 | ND |
| 2 | (CDCl$_3$) δ 8.67 (bs, 1H), 7.96 (d, 1H), 7.2-7.3 (m, 5H), 7.90 (m, 1H), 5.30 (m, 1H), 4.70 (m, 1H), 4.65 (d, 1H), 4.60 (t, 1H), 4.45 (d, 0.5H), 4.40 (d, 0.5H), 4.28 (m, 1H), 4.13 (m, 1H), 2.75 (m, 1H), 2.35 (m, 1H), 2.05 (m, 1H), 1.6-1.9 (m, 12H), 1.4-1.5 (m, 4H), 1.12-1.39 (m, 7H), 1.05 (m, 1H), 0.96 (s, 9H), 0.85 (m, 5H), 0.55 (m, 2H) ppm. |
| 3 | (CDCl$_3$) δ 8.10 (bs, 1H), 7.99 (d, 1H), 7.87 (bs, 1H), 7.52 (d, 1H), 7.09 (bs, 1H), 5.35 (m, 1H), 4.70 (m, 2H), 4.60 (t, 1H), 4.20 (m, 1H), 3.25 (m, 1H), 3.10 (m, 1H), 2.80 (m, 1H), 2.4 (m, 1H), 2.10 (m, 1H), 1.90 (m, 3H), 1.10-1.80 (m, 26H), 0.97 (s, 9H), 0.70-0.80 (m, 11H), 0.6 (m, 2H) ppm. |
| 4 | (CDCl$_3$) δ 8.12 (bs, 1H), 7.97 (d, 1H), 7.71 (bs, 1H), 7.22 (d, 1H), 6.99 (d, 1H), 5.33 (m, 1H), 4.67 (d, 1H), 4.60 (t, 1H), 4.50 (t, 1H), 4.20 (m, 1H), 2.83 (m, 1H), 2.79 (m, 1H), 2.40 (m, 1H), 2.11 (m, 1H), 1.82-2.00 (m, 5H), 1.00-1.80 (m, 19H), 0.97 (s, 9H), 0.62-0.96 (m, 10H), 0.6 (m, 2H) ppm. |
| 5 | (CDCl$_3$) δ 7.92 (d, 1H), 7.60 (d, 1H), 7.39 (d, 1H), 7.10 (bs, 1H), 7.00 (d, 1H), 5.35 (m, 1H), 4.65 (d, 1H), 4.60 (t, 1H), 4.40 (t, 1H), 4.20 (m, 1H), 4.08 (m, 1H), 2.80 (m, 1H), 2.45 (m, 1H), 2.15 (m, 1H), 1.90 (m, 3H), 1.65-1.83 (m, 7H), 1.48-1.60 (m, 4H), 1.40 (m, 3H), 1.23 (d, 3H), 1.20 (d, 3H), 1.18-1.30 (m, 4H), 1.10 (m, 2H), 0.97 (s, 9H), 0.90 (m, 4H), 0.85 (m, 2H), 0.62 (m, 2H) ppm. |
| 6 | (CDCl$_3$) δ 8.15 (bs, 1H), 8.00 (d, 1H), 7.90 (bs, 1H), 7.44 (d, 1H), 7.03 (bs, 1H), 5.35 (m, 1H), 4.70 (d, 1H), 4.65 (t, 1H), 4.60 (t, 1H), 4.20 (m, 1H), 3.25 (m, 1H), 3.10 (m, 1H), 2.80 (m, 1H), 2.40 (m, 1H), 2.10 (m, 1H), 1.90 (m, 4H), 1.00-1.80 (m, 21H), 0.97 (s, 9H), 0.94 (d, 3H), 0.93 (m, 3H), 0.92 (d, 3H), 0.88 (d, 2H), 0.62 (m, 2H) ppm. |
| 7 | (CDCl$_3$) δ 8.07 (bs, 1H), 7.97 (d, 1H), 6.92 (d, 1H), 6.79 (s, 1H), 5.22 (m, 1H), 4.75 (t, 1H), 4.62 (d, 1H), 4.58 (m, 1H), 4.05 (m, 1H), 2.78 (m, 1H), 2.57 (m, 1H), 2.42 (s, 3H), 2.40 (m, 1H), 1.6-1.92 (m, 12H), 1.15-1.50 (m, 9H), 0.97-1.10 (m, 4H), 0.96 (s, 9H), 0.82 (d, 2H), 0.80 (t, 3H), 0.61 (m, 2H) ppm. |
| 8 | (CDCl$_3$) δ 7.92 (d, 1H), 7.59 (d, 1H), 7.50 (d, 1H), 7.18 (d, 1H), 7.08 (bs, 1H), 5.37 (m, 1H), 4.67 (d, 1H), 4.66 (m, 1H), 4.41 (t, 1H), 4.20 (m, 1H), 3.77 (m, 1H), 2.78 (m, 1H), 2.4 (m, 1H), 2.12 (m, 1H), 1.90 (m, 5H), 1.01-1.88 (m, 27H), 0.99 (s, 9H), 0.92 (m, 5H), 0.85 (d, 2H), 0.62 (m, 2H) ppm. |
| 9 | (CDCl$_3$) δ 7.90 (d, 1H), 7.45 (d, 1H), 6.95 (d, 1H), 6.67 (d, 1H), 5.31 (m, 1H), 4.60 (m, 2H), 4.30 (t, 1H), 4.20 (m, 1H), 2.80 (m, 1H), 2.50 (m, 1H), 2.15 (m, 1H), 2.04 (m, 2H), 1.80-1.95 (m, 4H), 1.02-1.78 (m, 26H), 0.97 (s, 9H), 0.92 (m, 4H), 0.92 (d, 2H), 0.60 (m, 2H) ppm. |
| 10 | (CDCl$_3$) δ 8.08 (d, 1H), 7.87 (d, 2H), 7.58 (bs, 1H), 7.50 (dd, 1H), 7.48 (bs, 1H), 7.10 (bs, 1H), 6.51 (d, 1H), 5.60 (m, 1H), 5.39 (m, 1H), 4.93 (m, 1H), 4.77 (m, 1H), 4.52 (t, 1H), 4.11 (m, 1H), 4.03 (m, 1H), 2.80 (m, 2H), 2.53 (m, 1H), 2.30 (m, 1H), 1.90 (m, 1H), 1.67 (m, 5H), 1.57 (m, 1H), 1.49 (m, 1H), 1.40 (m, 2H), 1.20 (m, 2H), 1.07 (m, 1H), 0.95 (s, 9H), 0.8-0.95 (m, 9H), 0.65 (m, 4H) ppm. |
| 11 | (CDCl$_3$) δ 8.10 (d, 1H), 7.83 (d, 1H), 7.50 (d, 1H), 7.36 (d, 1H), 7.30 (m, 7H), 7.00 (bs, 1H), 6.53 (d, 1H), 5.59 (m, 1H), 5.32 (m, 1H), 4.78 (m, 1H), 4.72 (d, 1H), 4.58 (d, 0.6H), 4.57 (d, 0.4H), 4.48 (m, 1H), 4.41 (m, 1H), 4.09 (m, 1H), 3.97 (d, 0.6H), 3.96 (d, 0.4H), 2.79 (m, 1H), 2.56 (m, 1H), 2.25 (m, 1H), 1.90 (m, 1H), 1.70 (m, 5H), 1.50 (m, 2H), 1.36 (m, 2H), 1.20 (m, 2H), 1.08 (m, 1H), 0.97 (s, 9H), 0.8-0.91 (m, 7H), 0.6 (m, 2H) ppm. |
| 12 | (CDCl$_3$) δ 8.09 (d, 1H), 7.83 (d, 1H), 7.70 (bs, 1H), 7.50 (m, 2H), 7.10 (bs, 1H), 6.50 (d, 1H), 5.60 (m, 1H), 5.39 (m, 1H), 4.90 (m, 1H), 4.70 (d, 1H), 4.42 (t, 1H), 4.10 (m, 1H), 3.98 (m, 1H), 3.17 (m, 2H), 2.80 (m, 1H), 2.59 (m, 1H), 2.27 (m, 1H), 1.91 (m, 1H), 1.83 (m, 1H), 1.68 (m, 4H), 1.58 (m, 1H), 1.50 (m, 1H), 1.40 (m, 2H), 1.20 (m, 2H), 1.10 (m, 1H), 0.9-1.0 (m, 21H), 0.84 (d, 2H), 0.60 (m, 2H) ppm. |

We claim:

1. A compound selected from:

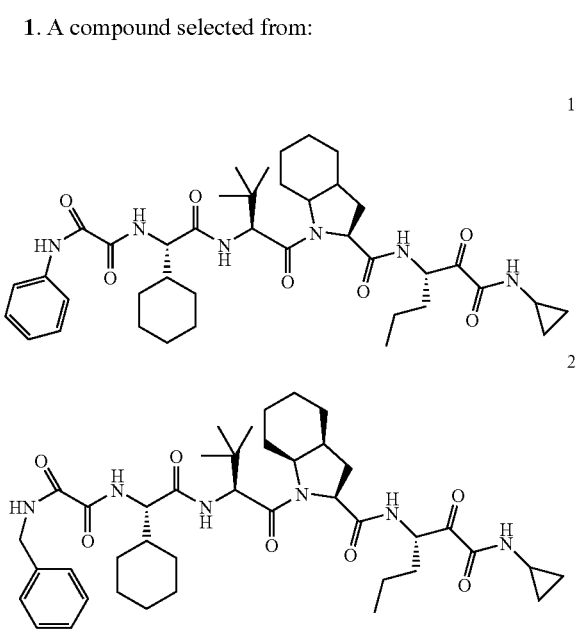

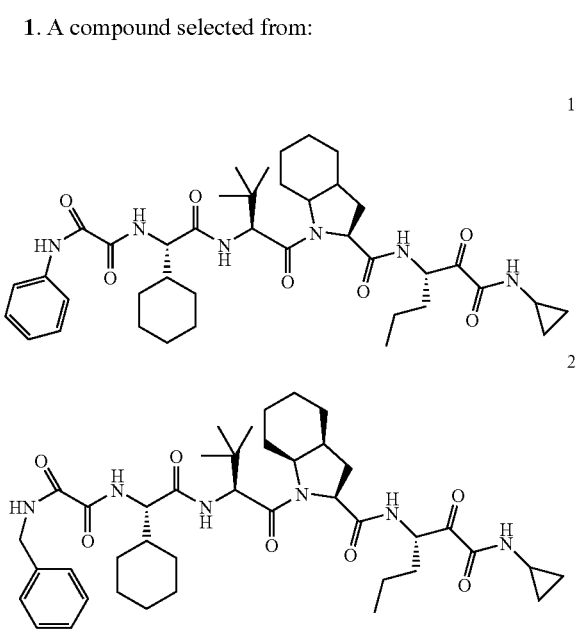

113
-continued

3
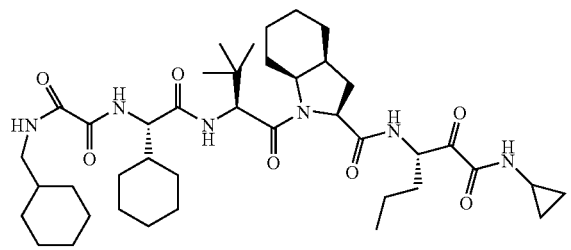

4
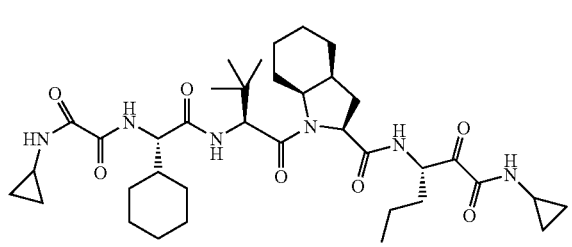

5
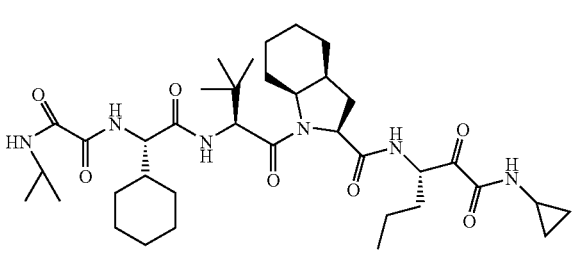

6
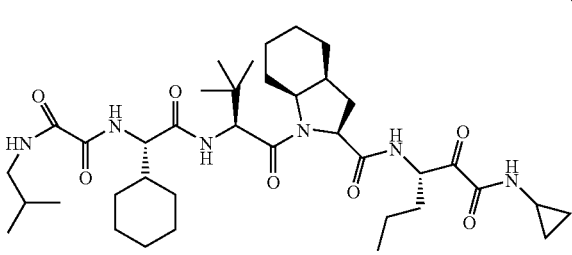

7
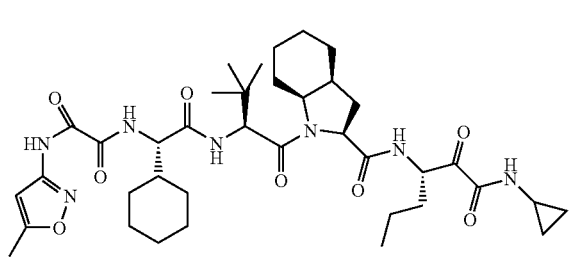

8
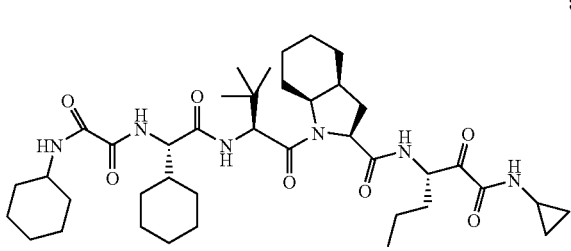

114
-continued

9
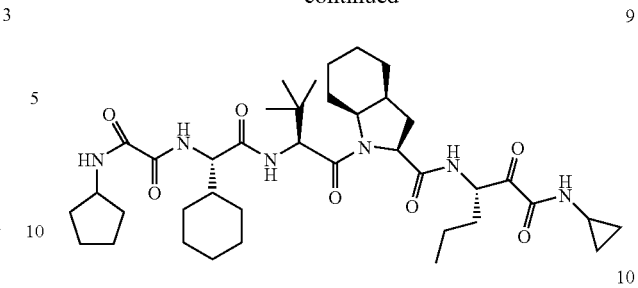

10
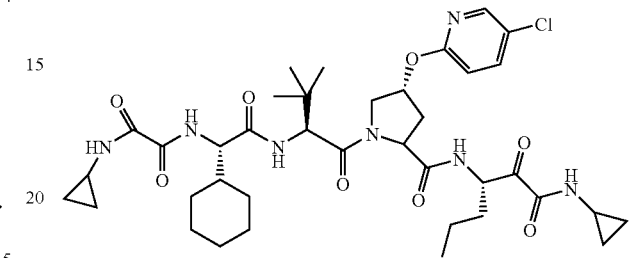

11
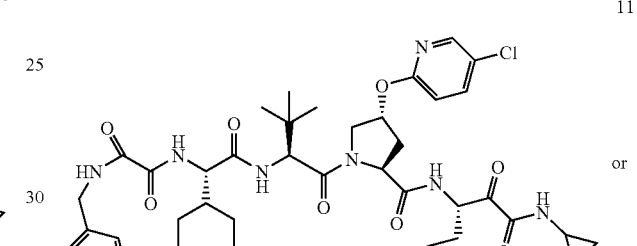

or

12
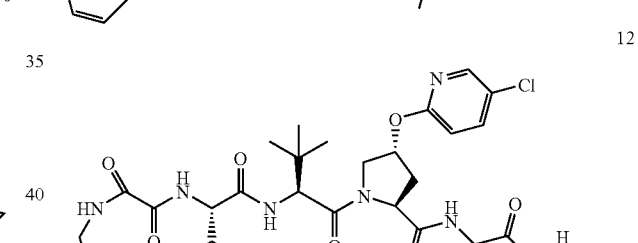

.

2. A pharmaceutical composition comprising a compound according to claim 1, or a pharmaceutically acceptable salt thereof in an amount effective to inhibit a serine protease; and a acceptable carrier, adjuvant or vehicle.

3. The composition according to claim 2, wherein said composition is formulated for administration to a patient.

4. A method of inhibiting the activity of a serine protease comprising the step of contacting said serine protease with a compound according to claim 1.

5. The method according to claim 4, wherein said protease is an HCV NS3 protease.

6. A method of treating an HCV infection in a patient comprising the step of administering to said patient a composition according to claim 3.

* * * * *